United States Patent
Oshida et al.

(10) Patent No.: US 8,361,784 B2
(45) Date of Patent: Jan. 29, 2013

(54) METHOD OF INSPECTING A DNA CHIP AND APPARATUS THEREOF

(75) Inventors: Yoshitada Oshida, Chigasaki (JP); Toshihiko Nakata, Hiratsuka (JP); Tomoaki Sakata, Hiratsuka (JP); Kenji Yasuda, Tokyo (JP); Satoshi Takahashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 1472 days.

(21) Appl. No.: 11/709,120

(22) Filed: Feb. 22, 2007

(65) Prior Publication Data

US 2007/0154938 A1 Jul. 5, 2007

Related U.S. Application Data

(62) Division of application No. 09/678,652, filed on Oct. 4, 2000, now Pat. No. 7,217,573.

(30) Foreign Application Priority Data

| Oct. 5, 1999 | (JP) | 11-283826 |
| Jan. 25, 2000 | (JP) | 2000-018002 |
| Jun. 16, 2000 | (JP) | 2000-181847 |
| Aug. 9, 2000 | (JP) | 2000-247896 |

(51) Int. Cl.
*C12M 1/34* (2006.01)
*G01N 21/64* (2006.01)

(52) U.S. Cl. ............... 435/288.7; 435/287.2; 422/82.08; 250/461.2; 382/129

(58) Field of Classification Search ............... 435/288.7
See application file for complete search history.

(56) References Cited

U.S. PATENT DOCUMENTS

| 4,538,613 A | 9/1985 | Rosenberg |
| 5,516,409 A | 5/1996 | Kambara |
| 5,783,397 A | 7/1998 | Hughes et al. |
| 5,830,645 A | 11/1998 | Pinkel et al. |
| 5,874,219 A | 2/1999 | Rava et al. |
| 5,981,956 A | 11/1999 | Stern |
| 6,262,423 B1 * | 7/2001 | Hell et al. ............ 250/458.1 |
| 6,455,861 B1 * | 9/2002 | Hoyt ................ 250/458.1 |
| 6,603,537 B1 * | 8/2003 | Dietz et al. ............. 356/39 |
| 6,686,582 B1 | 2/2004 | Volcker et al. |

FOREIGN PATENT DOCUMENTS

| JP | 07-147982 | 6/1995 |
| JP | 11-094747 | 4/1999 |
| JP | 11-118446 | 4/1999 |
| JP | 11-315095 | 11/1999 |
| WO | WO 99/23474 | 5/1999 |

* cited by examiner

*Primary Examiner* — William H Beisner
(74) *Attorney, Agent, or Firm* — Antonelli, Terry, Stout & Kraus, LLP.

(57) ABSTRACT

A DNA inspecting apparatus including driving means for relatively changing positions of the multi-spot lights and a position of the DNA chip so as to detect the fluorescent lights in such a manner that a desired area on the DNA chip is irradiated with the multi-spot lights, and a control system for determining and inspecting DNA information about the to-be-inspected DNA chip from fluorescent light intensities and fluorescent light positions of the desired area on the DNA chip, the fluorescent light intensities and the fluorescent light positions being detected by the driving means and the fluorescent light detecting means.

4 Claims, 56 Drawing Sheets

FIG. 6A
FIG. 6B
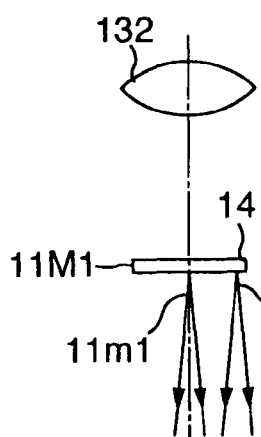
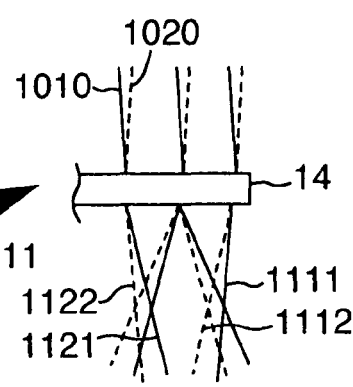
FIG. 6D
(320)
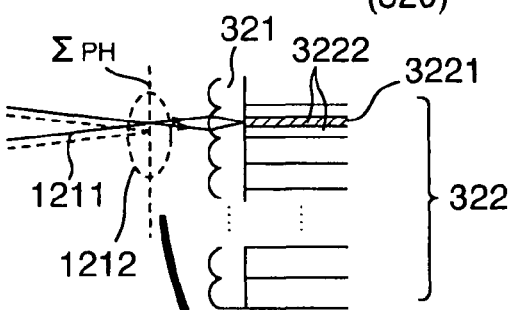
FIG. 6C
FIG. 6E
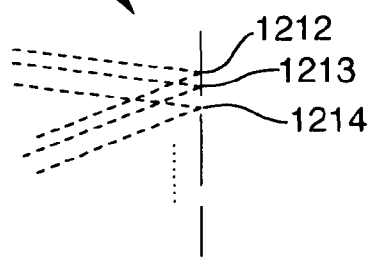

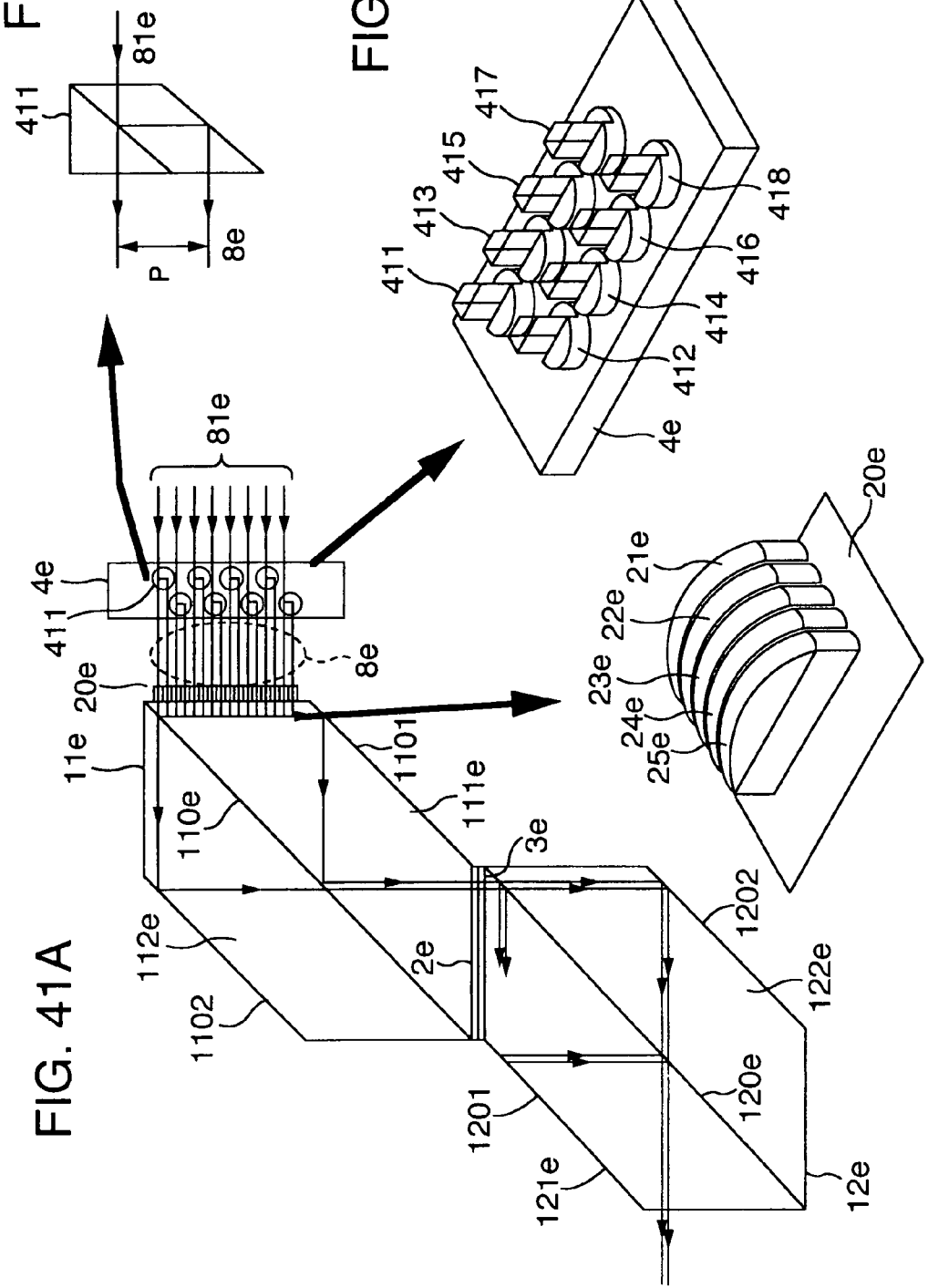
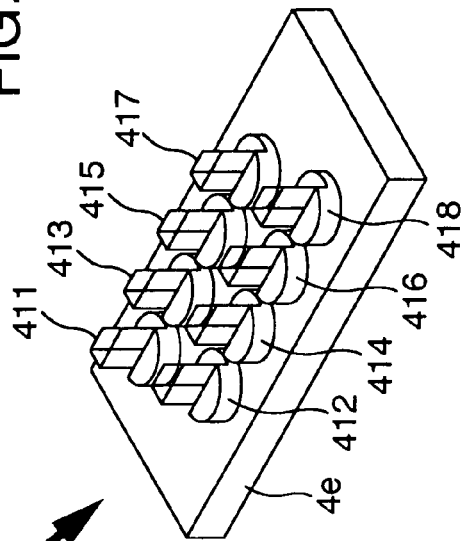
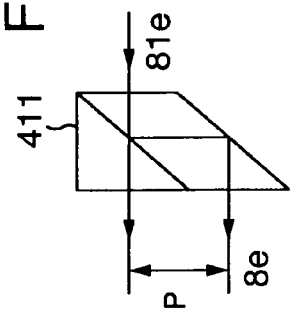
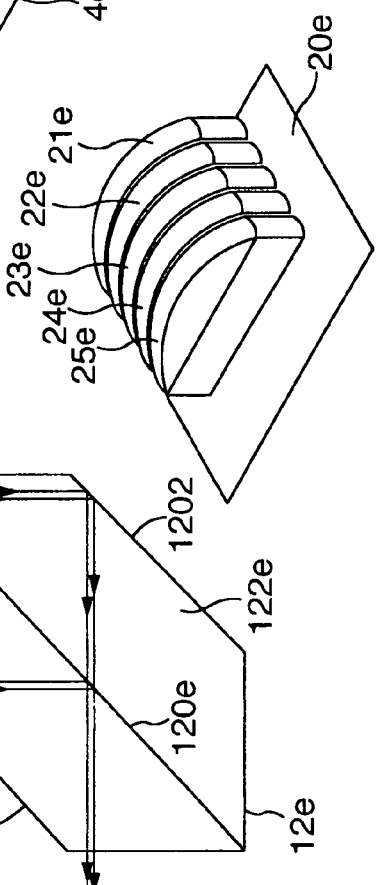
FIG. 41A
FIG. 41B
FIG. 41C
FIG. 41D

METHOD OF INSPECTING A DNA CHIP AND APPARATUS THEREOF

CROSS REFERENCE TO RELATED APPLICATION

This is a divisional of U.S. application Ser. No. 09/678,652, filed Oct. 4, 2000, now U.S. Pat. No. 7,217,573. This application relates to and claims priority from Japanese Patent Application Nos. 11-283826, filed on Oct. 5, 1999; 2000-018002, filed on Jan. 25, 2000; 2000-181847, filed on Jun. 16, 2000 and 2000-247896, filed on Aug. 9, 2000. The entirety of the contents and subject matter of all of the above is incorporated herein by reference.

BACKGROUND OF THE INVENTION

The present invention relates to an apparatus for reading and analyzing an emitted light (fluorescent light) pattern emitted from a sample located on a plane. More particularly, it relates to a method and an apparatus by which living body samples, such as a DNA, a RNA and an oligonucleotide marked by a fluorescent material, are trapped at a plurality of positions on a substrate so as to read an emitted light pattern from the fluorescent marker with a high-resolution, at a high-speed and with a high-sensitivity.

Analysis technologies for analyzing the DNA and proteins are important in fields of medicine and biology including gene analysis and gene diagnosis. In particular, in recent years, attention has been focused on a method and an apparatus by which, using a DNA probe array (which is called in other way by various names such as oligochip, DNA chip or biochip, but hereinafter the DNA probe array is employed as the generic name), a variety types of DNA sequence information and gene information are inspected and analyzed simultaneously from one specimen to be inspected. The DNA probe array is implemented in the following way: A substrate such as a glass is used and separated into a plurality of (millions to tens of millions) areas, and target (usually, different types of) DNA probes are fixed onto the respective areas so as to form the respective areas into microscopic reaction areas, thus implementing the array. The reaction of the specimen with the array allows a target DNA in the specimen to be trapped in a state of being hybridized with the fixed DNA probes. Moreover, the target DNA is coupled with a probe such as a fluorescent probe, thereby making it possible to measure the coupled state (the position, i.e., the hybridized sequence) and its quantity with the use of the fluorescence intensity and so on. This permits the array to be utilized in the gene diagnosis and the sequence.

A microscope-like apparatus (confocal fluorescent microscope), which is usually called a scanner, is used in order to read the fluorescence intensity emitted from the fluorescent marker on the target DNA trapped in the respective reaction areas of the DNA probe array (for example, refer to JP-A-11-315095). In this apparatus, the array is irradiated with a excitation light such as a laser light which has been modified into one microscopic spot-shaped configuration, and fluorescent lights generated are separated from the excitation light using a spectroscopic device such as an interference filter, then detecting the fluorescence intensity using a photo detector such as a photomultiplier tube. At that time, the excitation light is waved using a galvanometer mirror so as to scan, in a 2-dimensional manner, the microscopic spot formed on the array. Otherwise, the position of the microscopic spot is fixed, then scanning the array in the 2-dimensional manner. These scans make it possible to recognize the fluorescence intensity distribution of the entire array, i.e., the degree of the coupling toward each DNA probe.

When trying to apply the DNA inspection to a living body inspection such as a conventional blood inspection, it becomes absolutely required to execute the inspection toward a large number of living specimens at a high-speed. In the conventional technologies, however, it takes so much inspection time to irradiate one point with the excitation light spot, which is equivalent to a necessary inspecting resolution of the DNA chip, and to detect the obtained fluorescent lights one after another. This is concerned with the fact that it is impossible to shorten unlimitedly a time needed to detect this one point. Namely, this is attributed to the fact that the time $\Delta t_L$, which is needed up to the finishing of the fluorescent light generation after the irradiation with the excitation light, is equal to substantially 10 ns. Transferring the detection to the next detection point without waiting for the finishing of the fluorescent light generation makes the detection itself impossible.

Also, it is required to perform the detection with a high-sensitivity that corresponds up to a state where there exist several fluorescent molecules within the spot light size equivalent to the above-described necessary detecting resolution. However, all of the generated fluorescent lights are not detected. Namely, a light utilization efficiency of the detecting optical system and a quantum efficiency of the photomultiplier tube used for the optical detection are not equal to 100%. Moreover, the following values are small: An efficiency with which the excitation light is absorbed in the fluorescent material and a probability with which the absorbed excitation light is converted into the fluorescent light. This requires that the detection be executed by spending a time that is at least tens to hundreds times longer than $\Delta t_L$. Furthermore, the more this time is lengthened, the higher the accuracy of a weak light detection becomes which is almost the same as the photon counting.

Also, in order to accomplish such a high-speed characteristic at a practical level, the following conditions are required: Eliminating or reducing influences of foreign substances that are composed of various types of proteins mixed into the DNA chip, or maintaining all the time a focal point of the detecting system onto the inspection plane on which the fluorescent material-added target has been hybridized. Also, in some cases, it becomes necessary to perform the detection with reference to a plurality of fluorescent lights at a high-speed.

When forming multi-spot lights from a bean emitted from a laser light-source, if the emitted light is wished to be modified into the multi-spot lights without being wasted, i.e., for example, when trying to form 50 multi-spot lights that are 0.04 mm in diameter and are arranged in a line with a pitch of 0.4 mm, the emitted laser beam is formed so that the beam becomes an ellipse-shaped configuration the longitudinal-to-transverse ratio of which is equal to 1 to 50. Irradiating, with the ellipse-shaped beam, a microlens array where microlenses are arranged with a pitch of 0.4 mm makes it possible to obtain the 50 multi-spot lights about 0.04 mm in diameter and having the pitch of 0.4 mm, if a focal length of the microlenses is equal to 60 mm, for example. Since the intensity distribution of the laser beam is Gaussian distribution, in the arrangement of the 50 multi-spot lights formed in the method as described above, spots situated in proximity to the center of the arrangement become lighter and spots situated in proximity to the periphery thereof become darker. Trying to equate as much as possible the intensities of the spots at the center with those of the spots on the periphery requires the following: A spread area of the incoming ellipse-shaped beam should be made large enough as compared with the width of the 50 microlenses. As a result, half or more of the laser beam energy emitted from the laser light-source turns out to be wasted.

In the DNA probe array, the number of the types of the fixed probes is increased and thus its density is becoming more and more heightened. On account of this, an apparatus for measuring the fluorescent marker distribution of the DNA probe array is expected to operate at the high-speed and with the high-sensitivity in addition to implementing the high-resolution characteristic. In the above-described apparatus, however, no sufficient consideration has been given to this point. Namely, it is required to make the spot diameter of the excitation light more microscopic in order to implement the high-resolution characteristic, whereas the scanning time is increased at that case (when an exposure time for each spot is identical). Moreover, making the spot diameter smaller lessens the number of the fluorescent molecules existing within the spot diameter, thereby lowering the detection sensitivity. Also, in order to implement the high-speed characteristic, it is required to increase the scanning rate or to make larger the spot diameter of the excitation light. Increasing the scanning rate, however, shortens the excitation time for the fluorescent material, thereby lessening the fluorescence intensity or increasing a circuit noise to lower the detection sensitivity. Also, in order to implement the high-sensitivity characteristic, it is required to make the spot diameter larger and to delay the scanning rate. Namely, implementing the high-resolution characteristic, implementing the high-speed characteristic and implementing the high-sensitivity characteristic are contradicted to each other, and accordingly it was difficult to accomplish them.

Also, there has been proposed an apparatus by which a plurality of microscopic spots are formed on a sample surface and lights from the plurality of microscopic spots are detected simultaneously (for example, refer to JP-A-11-118446). In this configuration, a light-flux from an excitation light-source is enlarged and a 2-dimensional microlens array is located in the enlarged light-flux so as to form the plurality of irradiation spots, then projecting the spots onto the sample surface. In this case, however, especially when a laser light is used as the excitation light, because of the Gaussian distribution characteristic of the laser beam, the light intensities of spots in proximity to the center are intense and the light intensities of the spots become lower as their positions come nearer to the periphery. Accordingly, it is difficult to equate all the light intensities of the plurality of irradiation spots. This problem is partly solved by enlarging the excitation light up to a light-flux the diameter of which is large enough as compared with the width of the 2-dimensional microlens array. In this case, however, the light utilization efficiency is no good and the light intensities are decreased, thus resulting in such a problem that the detection sensitivity is deteriorated.

In a method of focusing a one-beam laser light onto a target to be inspected, the detection is executed on a one-pixel by one-pixel basis in a time-sequence manner. As a result, when the fluorescent light is extremely weak, it takes a time to execute the detection equivalent to the one-pixel. Consequently, it takes a considerable amount of time to detect the entire 2-dimensional image. Even if an excitation light of the one-beam laser is strengthened in order to detect the weak fluorescent light emitting target at a high-speed, when trying to detect, for example, 6000×6000 pixels in 1 minute, the detecting time per pixel turns out to become 1 to 2 μsec (microseconds). Executing the detection in such a short time makes it difficult to detect the fluorescent light detection intensity in a broad dynamic range (for example, $2^{16}$). Also, since a normal fluorescent material emits the fluorescent light with a delay of $10^{-9}$ to $10^{-5}$ sec after receiving the excitation light, the above-described per-pixel fluorescent light detecting time of 1 to 2 μsec prevents the fluorescent light detection from being fully accomplished. Meanwhile, in a method using Nippou disk, the light is utilized effectively only by the amount of a ratio of a microscopic aperture in a uniform light. This condition requires a considerable amount of time to be spent to detect the weak fluorescent light.

SUMMARY OF THE INVENTION

In order to solve the above-described problems, the present invention provides methods and units described hereinafter.

The inspection of a DNA chip to be inspected is executed in the following steps: Irradiating mutually different positions with a plurality of M excitation lights simultaneously with the use of an objective lens for a time $\Delta t$ that is longer than a fluorescent light attenuation time, the excitation lights including a spot diameter d that is smaller than a dimension D of each cell, guiding obtained fluorescent lights to a fluorescent light detecting optical path, detecting the fluorescent lights on an image-forming plane that is in a conjugation relationship with irradiation spots onto the DNA chip, and executing the inspection of the DNA chip from positions and intensities of the fluorescent lights. At this time, the spot diameter is set to be substantially 1/N of an integer N indicating the cell dimension. Moreover, relative positions between the irradiation spots and the DNA chip are caused to differ j times in sequence so as to inspect the entire inspection target positions $LN^2=Mj$. Here, L denotes the cell number within the chip. Also, N is made equal to 2 or more and each cell is divided into a plurality of portions so as to select and process only significant data out of $N^2$ data existing within one call, thereby executing the precise inspection. Executing the inspection in this way allows the fluorescent lights to be detected in a time less than $LN^2/(6\times10^5)$ sec with reference to the entire inspection target sample-point number $LN^2$ of the DNA chip.

There are provided M light-receiving apertures that have an effective diameter on the image-forming plane that is in the conjugation relationship with the plurality of M irradiation spots onto the DNA chip, the effective diameter being of substantially the same order as an effective diameter of the irradiation spot images. Moreover, an area other than the light-receiving apertures is light-shielded so as to detect the respective lights that have passed through the light-receiving apertures, thereby eliminating noise lights from the irradiation spots or from an area other than the irradiation spot plane so as to perform the inspection having a high signal-to-noise ratio. Also, the M light-receiving apertures that have the effective diameter are optical fiber light-receiving ends, the effective diameter being of substantially the same order as the effective diameter of the irradiation spot images. At the optical fiber light-receiving ends, the lights emitted from optical fiber light-emitting ends are detected, thereby performing the inspection having an even higher signal-to-noise ratio.

The plurality of M irradiation spots onto the DNA chip are arranged on a straight line with a spacing of substantially kd with reference to the spot diameter d and an integer k. After the irradiation with this spot array during the time $\Delta t$ has been performed, the spot array is displaced in an array direction by a distance of substantially d, and then the irradiation during the time $\Delta t$ is performed. This operation is repeated k times in sequence, thereby performing the inspection concerning kM spot positions in the array direction. At the same time, the DNA chip and an inspecting apparatus are relatively displaced at least in a direction perpendicular to the array direction, thereby inspecting a desired 2-dimensional area of the DNA chip. Also, the above-described movement of the spot array is characterized by being performed using an acoustooptic deflector.

Also, it is desirable to set the integer k to be 2 or more. Furthermore, in view of the signal-to-noise ratio, it is more advantageous to set the integer k to be 5 or more.

The spot array is formed with the microlens array. The spot array can also be formed using a hologram. In synchronization with the above-described movement of the spot array in the array direction, a fluorescent light detection deflecting unit is provided within the fluorescent light detecting optical path so that the fluorescent lights generated by the excitation lights come onto substantially the same location on the above-described light-receiving apertures. At this time, a deflecting unit using a piezoelectric device is employed as the fluorescent light detection deflecting unit. Also, the fluorescent light detection deflecting unit is configured with a wavelength selection beam splitter for permitting the excitation lights to pass through and reflecting the fluorescent lights. This makes it possible to perform the detection with a higher efficiency. Also, in order to enhance the separation from the excitation lights, a filter for permitting only the fluorescent lights to pass through and light-shielding the excitation lights is used within the fluorescent light detecting optical path isolated from excitation optical paths.

The above-described M multi excitation spot lights are configured so as to pass through substantially the same position A on a pupil of the objective lens. In addition, the excitation lights reflected regularly on the DNA chip are configured so as to reach a position B' on the pupil of the objective lens. In this way, a light-shielding unit for light-shielding the reflected excitation lights is provided at the position B' on the pupil of the objective lens, or is provided at an image position of B' that exists within the fluorescent light detecting optical path and exists on a plane conjugated with the pupil of the objective lens. This allows the excitation lights becoming the noise components to be eliminated from a fluorescent light detection signal.

The above-described M multi excitation spot lights are configured so as to pass through substantially the same position A on the pupil of the objective lens. In addition, the excitation lights reflected regularly on the DNA chip are configured so as to pass through a position B that differs from the position A on the pupil of the objective lens. In this way, a light-shielding member for light-shielding the reflected excitation lights having a desired diameter with B as its center is located on the pupil of the objective lens, or is located at a position that is within the fluorescent light detecting optical path and is conjugated with the pupil of the objective lens. This configuration allows the excitation lights becoming the noise components to be eliminated from the fluorescent light detection signal.

Moreover, the reflected excitation lights to be light-shielded are employed as the regularly reflected excitation lights. The excitation lights scattered from the foreign substances within the DNA chip are extracted by being caused to pass through from outside the above-described light-shielding unit or the above-described light-shielding member. Then, the extracted scattered lights are branched off from the above-described fluorescent light detecting optical path so as to image-pickup the scattered lights at a position conjugated with the irradiation spots onto the DNA chip, thereby performing the detection. Next, using the image-pickup information on images of the detected scattered lights, the fluorescent light information detected by the above-described fluorescent light detection deflecting unit is corrected. This method precludes the influences of the scattered lights scattered from the foreign substances existing in the DNA chip, thereby making it possible to execute the precise detection.

The above-described M multi excitation spot lights are formed using a laser light-source. This allows high-intensity excitation irradiation to be accomplished on the microscopic spots. Also, the M multi-spot excitation lights are formed using a plurality of semiconductor laser light-sources, thereby accomplishing even higher excitation irradiation in a small implementation volume. At this time, the lights emitted from the plurality of semiconductor laser light-sources are configured so that the lights are guided into optical fibers and are then emitted from the optical fiber light-emitting ends that are aligned with M desired pitches. This configuration makes it possible to obtain the M multi excitation spot lights arranged in the desired pitch arrangement.

Employing, as an optical signal storage type image-pickup unit, a 2-dimensional image-pickup apparatus having an ultra-high sensitivity and including $N_x \times N_y$ pixels, and assuming that $n_x$, $n_y$ are integers, $N_x \times N_y$ spots are simultaneously irradiated with the excitation lights of the spot diameter d with a pitch of $n_x d$ in the x direction and with a pitch of $n_y d$ in the y direction. Then, $N_x \times N_y$ fluorescent light spot images obtained in this way are detected using the ultra-high sensitivity 2-dimensional image-pickup apparatus, and a relative position between the detecting apparatus and the DNA chip is displaced with a pitch of d in the x, y directions by the amount of $n_x \times n_y$ steps. This method makes it possible to detect a desired area on the DNA chip.

Also, the above-described excitation lights, which include a plurality of different wavelengths, separate and detect a plurality of fluorescent materials-added different targets. Furthermore, the plurality of fluorescent materials-added different targets are simultaneously irradiated with the excitation lights including the plurality of different wavelengths, thereby separating and simultaneously detecting the different targets. This method makes it possible to detect various types of targets at high-speed.

On the inspection plane with which a desired fluorescent material-added target on the above-described DNA chip to be inspected has been hybridized, a second light is obliquely incoming into a proximity to the above-described excitation spot lights and a position at which the second light is reflected on the inspection plane is detected, thereby detecting the focal point. A relative distance between the inspection plane and the above-described objective lens is controlled in accordance with this focal point information, thereby allowing the focusing to be achieved. Also, the obliquely launched second light is configured so as to pass through the objective lens. This permits the focal point detection and control to be executed with a simplified configuration.

The above-described obliquely launched second light is converted into an S-polarized light toward the detection plane. This enhances a reflectance on the fluorescent light detection plane, thereby making it possible to execute the correct focal point detection. In addition, as the wavelength of the obliquely launched second light, there is employed a wavelength that exerts no excitation to the above-described fluorescent material. This permits the precise detection to be executed without superimposing the noise on the fluorescent light detection signal.

It is an object of the present invention to provide a method and an apparatus therefor that obtain multi-spot lights having a substantially uniform intensity by solving a conventional problem that the light utilization efficiency in the conventional multi-spot light forming method is no good and there exist a large variation in the intensities among the multi-spot lights.

It is another object of the present invention to provide a method and an apparatus therefor that execute the confocal point detection, the fluorescent light detection and the DNA inspection with the use of the multi-spot lights having the substantially uniform intensity.

In order to solve the conventional problem and obtain multi-spot lights positioned in proximity to each other, the present invention presents the following configuration:

Namely, a plurality of N laser beams which travel in substantially the same direction and the adjacent beams of which are in comparative proximity to each other are launched into a polarization component so as to separate each laser beam into two beams of mutually orthogonal polarized components, thereby forming a plurality of 2N laser beams. After that, the plurality of 2N laser beams are formed into a plurality of 2N laser beams which travel in substantially the same direction and the adjacent beams of which are in comparative proximity to each other.

As a concrete method of obtaining such doubled proximate beams, the plurality of N proximate laser beams are launched into the above-described polarization component including a multi-spot lights-doubling prism that has a polarization beam split plane and total reflection planes. Here, the total reflection planes are parallel to the polarization beam split plane and are positioned at distances of L1 and L2 from the polarization beam split plane. This makes it possible to increase the number of the plurality of proximate laser beams up to the doubled number, i.e., 2N.

Also, the plurality of N proximate laser beams are launched into the above-described polarization component including an anisotropic optical medium. Then, in the anisotropic optical medium, each laser beam is separated into the two beams of the mutually orthogonal polarized components, thereby forming the plurality of 2N laser beams. This makes it possible to form the plurality of N proximate laser beams into the plurality of 2N laser beams which travel in substantially the same direction and the adjacent beams of which are in comparative proximity to each other.

In addition, the use of the above-described beam-doubling type polarization components in plural number M makes it possible to obtain $2^M N$ laser beams.

The plurality of N proximate laser beams, which are launched into at least one of the above-described one or more of polarization components, are formed into converging laser beams, respectively. This allows the microscopic multi-spot lights to be obtained at a convergence position of the converging laser beams. At this time, the converging laser beams are formed using lenses arranged in plural number, thereby forming the multi-spot lights.

Also, a mask, in which $2^{M'} N$ or more of apertures having a diameter substantially equal to a convergence diameter of the multi-spot lights are arranged with reference to an integer M' satisfying $1 \leq M' \leq M$, is located at the convergence position of the above-described converging laser beams so that the multi-spot lights are focused onto the apertures. This makes it possible to obtain pure microscopic multi-spot lights without the noise lights or stray lights.

The above-described plurality of N laser beams can also be doubled even when the plurality of N laser beams have a 4 d or less of adjacent spacing pitch with reference to the beam diameter d of the laser beam emitted from the laser light-source or of the semiconductor laser beam formed into a parallel beam. Also, executing the doubling makes it possible to reduce the adjacent beam spacing further down to $\frac{1}{2}^{M'}$.

Namely, without using the lens system, it is possible to form the multi-spot lights having the pitch smaller than the diameter d of the laser beam formed into the parallel light-flux.

As a method of forming the above-described plurality of N laser beams, there is provided one or more of 2nd beam-doubling prisms having a cross section of a triangle and a cross section of a parallelogram. Here, the triangle has an oblique side forming an angle of substantially 45 degrees toward the light-emitting surface, and the parallelogram is in contact with this oblique plane and has a total reflection plane that is parallel to this oblique plane. This method, through the operation of the second beam-doubling prisms, makes it possible to form, for example, N/2 laser beams into the plurality of N laser beams.

Moreover, there are used two or more types of the 2nd beam-doubling prisms having dimensions that are different from the dimension of the above-described 2nd beam-doubling prism. Then, these prisms are arranged from the largest to the smallest in sequence from the travelling directions of the beams in an n-stage cascaded manner, thereby $2^n$ times multiplying the number of the beams. Namely, assuming that the dimension of the beam-doubling prisms at the final stage is equal to D, their number is set to be N/2, and the dimension and the number of the beam-doubling prisms at a stage preceding thereto are set to be 2D and N/4, respectively, and the dimension and the number of the beam-doubling prisms at the first stage are set to be $2^{n-1}D$ and N/2', respectively. This method allows the N laser beams to be obtained from an extremely small number of $N/2^{n+1}$ laser beams.

The methods explained so far permits the multi-spot lights to be obtained from the laser beams emitted from the one laser light-source or the plurality of laser light-sources. What is more, using the polarization components or the beam-splitting prisms, one beam is doubled in any one of the beam-doubling methods. On account of this condition, an energy summation of the beams after being split into the two can be made equal to 92% or more of the original beam energy. Besides, even when taking into consideration the reflection losses on the surfaces of the lenses forming the converging laser beams or on the surfaces of the polarization components, 70% or more of the total energy resulting from summing up the respective emitting laser energies can be converted into the total energy of the multi-spot lights.

Furthermore, the reflection losses on the surfaces of the above-described optical components are prevented using an antireflection coat and the like. This method makes it possible to convert, into the total energy of the multi-spot lights, 90% or more of the total energy resulting from summing up the respective emitting laser energies of the laser beams emitted from the one or more of laser light-sources.

In comparison with the conventional method by which the multi spots are formed from the intensities at the various locations of the Gaussian distribution, the splitting of the beam can be made uniform more easily, and the variation in the respective spot energies among the multi-spot lights can be restrained within ±20%.

What is more, polarization states of the lights incoming into the above-described polarization components are adjusted to the correct states, or a film thickness of a multi-layered film type polarization beam splitter is adjusted to the correct thickness. This allows the intensities of the doubled beams to be substantially equated with each other, thereby making it possible to restrain within ±10% the variation in the respective spot energies among the multi-spot lights.

The above-explained $2^{M'}$ times multiplication of the number of the laser beams makes it possible to form the proximate multi microscopic spots. Thus, the multi-spot lights obtained in this way are used for the confocal point detection, the fluorescent light detection or the DNA detection or the like. This makes it possible to execute the conventionally impossible detection where the light utilization efficiency is high and the variation among the multi-spot lights is small, thereby eventually allowing the confocal point detection, the fluorescent light detection or the DNA detection or the like to be executed at a high-speed and with a high-accuracy.

The multi-spot lights formed using the above-described multi-spot light forming methods according to the present invention are projected onto an object to be observed. Then, the lights having been reflected at or having passed through the object to be inspected are caused to pass through multi apertures located at positions at which the above-described projected spots are image-formed. Next, the lights having passed through the respective apertures are each detected individually. Executing the confocal point detection in this way makes it possible to execute the confocal point detection where the light utilization efficiency is high and the variation among the multi-spot lights is small, thereby implementing the high-speed and high-accuracy confocal point detection.

The multi-spot lights formed using the above-described multi-spot light forming methods according to the present invention are employed as excitation lights, then being projected onto the object to be observed that includes a fluorescent material. Then, fluorescent lights generated by the excitation lights at the object to be inspected are separated from the excitation lights. Next, detectors are located at positions at which the fluorescent lights generated at the excitation light-projected spots are image-formed, thereby detecting the fluorescent lights at the positions of the respective multi-spot lights. This allows the plurality of positions to be simultaneously irradiated with the excitation lights with a high-intensity. Also, since the variation among the respective spots is small, it becomes possible to execute a high-speed and high-accuracy fluorescent light detection.

In the above-described fluorescent light detection, the fluorescent lights are caused to pass through multi apertures located at the positions at which the fluorescent lights generated at the excitation light-projected spots are image-formed. In addition, there are located the detectors for individually detecting the fluorescent lights having passed through the respective apertures. This eliminates fluorescent lights other than the fluorescent lights generated by the excitation lights at the object to be observed, thereby making it possible to execute a fluorescent light detection having a high signal-to-noise ratio.

The multi-spot lights formed using the above-described multi-spot light forming methods according to the present invention are employed as the excitation lights, then being projected onto the object to be observed that includes a fluorescent material-added DNA. The target to be observed is implemented in the following way: A known probe DNA is attached to a predetermined position on a substrate such as a glass, and a target DNA is poured onto the glass substrate so as to hybridize the target DNA corresponding to the nucleotide sequence of the probe DNA, thus implementing the object to be observed. Here, the target DNA is formed by adding the fluorescent material to an end of the DNA purified and amplified from a living body sample, i.e., a target to be inspected. The excitation lights of the multi-spot lights are irradiated with the object to be observed so as to excite the fluorescent material added to the DNA, thereby generating fluorescent lights. Then, the fluorescent lights are separated from the excitation lights, and the detectors are located at positions at which the fluorescent lights generated at the excitation light-projected spots are image-formed. This makes it possible to detect the fluorescent lights at the positions of the respective multi-spot lights, thus allowing the DNA to be inspected from the detected positions and the detected signal intensity.

In the above-described DNA inspection, the fluorescent lights are caused to pass through the multi apertures located at the positions at which the fluorescent lights generated at the excitation light-projected spots are image-formed, then individually detecting the fluorescent lights having passed through the respective apertures. This makes it possible to detect the fluorescent light intensities at the positions of the respective multi-spot lights so as to inspect the DNA, thereby being capable of executing the DNA inspection having an even higher signal-to-noise ratio.

In the fluorescent light detection and the DNA inspection, in many cases, a wavelength of the excitation lights and that of the fluorescent lights come comparatively close to each other. The use of the multi-spot lights in such a case enlarges the fields-of-view in the detection and the inspection. This condition makes insufficient the characteristics of the optical systems for separating the fluorescent lights from the excitation lights, the optical systems being inserted halfway in the course of guiding, to the detecting systems, the fluorescent lights generated by the respective multi-spot excitation lights. Namely, the incident angles of the fluorescent lights incoming into the optical systems for separating the fluorescent lights from the excitation lights become different at the respective spots. Here, examples of the optical systems are the wavelength separating beam splitter and the interference filter that are installed halfway extending from the image-forming optical system to the detectors. As a result, the excitation lights to be shielded leak away depending on the location in the multi-spot lights, which makes the accurate detection impossible.

In order to solve the above-described problem, in the method of separating the fluorescent lights from the excitation lights, in addition to still using the wavelength separating beam splitter, the image-forming optical system is replaced by a telecentric image-forming optical system. In the telecentric image-forming optical system, primary light-rays of the fluorescent lights become parallel to each other, the fluorescent lights being generated from the respective spots extending from the image-forming optical system to the image-formed positions through the excitation by the respective multi-spot lights. Moreover, the interference filter and/or the wavelength separating beam splitter are inserted between the telecentric image-forming optical system and the image-forming positions. This method causes the fluorescent light generated from whatever spot excitation light to be launched into the interference filter or the wavelength separating beam splitter at an incident angle that is common to all the fluorescent lights. As a consequence, concerning the fluorescent light from whatever spot and the excitation lights becoming the noise components as well, it becomes possible to select the fluorescent lights and to eliminate the excitation lights under the same condition, i.e., under an optimum condition. This situation allows the fluorescent light detection to be executed with an extremely small amount of the excitation light leakage, i.e., with an extremely small amount of the noise. As is seen from the above-described explanation, the use of this fluorescent light detecting method further makes it possible to perform, precisely and with a high-accuracy, the DNA inspection where it is required to detect the fluorescent lights the intensities of which are exceedingly weaker as compared with the intensities of the reflected excitation lights.

It is an object of the present invention to provide a distribution measuring apparatus for measuring the fluorescent marker distribution in the DNA probe array and the like, the distribution measuring apparatus being capable of solving the conventional problems and accomplishing the high-resolution performance and the high-speed characteristic at the same time.

The fluorescent marker distribution measuring apparatus according to the present invention and accomplishing the above-described object is an apparatus for scanning and reading a light-emission pattern from the fluorescent marker captured on a sample surface on a substrate. The fluorescent marker distribution measuring apparatus is characterized by including the following configuration components: A stage for mounting thereon the substrate of a target to be read, a unit for forming a plurality of irradiation spots on the sample surface on the substrate with a specified spacing that is larger than a diameter of the irradiation spots, a movement mechanism for moving the stage, a converging/detecting unit for converging and detecting light-emissions generated from the plurality of irradiation spots on the sample surface, a control unit for controlling the movement mechanism so that the substantially entire surface of the sample surface is irradiated in correspondence with the formation positions of the plurality of irradiation spots, and a processing unit for processing a signal from the converging/detecting unit so as to reconstruct images on the sample surface. The intensities of the plurality of irradiation spots are set to be substantially almost equal to each other.

The unit for forming the plurality of irradiation spots can be configured as follows: The unit includes at least one laser light-source as excitation light-sources. Moreover, the unit splits a light emitted from an excitation light-source so as to image-form the irradiation spots in such a manner that the irradiation spots are arranged on the sample surface and a spacing of adjacent irradiation spots becomes smaller than 1 mm. The unit for splitting the light emitted from the excitation light-source can be configured as the splitting prism, the optical anisotropic medium, the optical fiber, a polarization mirror or a combination of these devices.

The unit for forming the plurality of irradiation spots can also be configured as follows: The unit includes N (N≧1) excitation light-sources and M-stage 2-splitting units (M>2), and forms $N \times 2^M$ irradiation spots. As the 2-splitting unit, there can be employed the splitting prism, the optical anisotropic medium, the optical fiber or the polarization mirror.

The unit for forming the plurality of irradiation spots can also be configured as follows: The unit includes a plurality of laser light-sources and a plurality of optical fibers. Furthermore, light-emmitting ends of the plurality of optical fibers are located on a straight line, thereby forming the plurality of irradiation spots.

It is preferable that the plurality of irradiation spots should be positioned on a straight line with a substantially fixed spacing.

The converging/detecting unit converges and, almost simultaneously, detects a plurality of fluorescent emitted lights generated from the plurality of irradiation spot-portions. The unit includes a wavelength selecting filter so as to separate fluorescent components from excitation components out of the emitted lights generated from the plurality of irradiation spot-portions, then detecting the fluorescent components. The converging/detecting unit can also be configured as follows: The unit has pinholes at which the emitted lights generated from the plurality of irradiation spot-portions are image-formed, then detecting the lights passing through the pinholes, the pinholes the number of which being the same as that of the irradiation spot-portions.

The control unit makes it possible to measure the entire plane of the sample surface by the following method: Employing, as a unit, step-like movements on a first microscopic width basis at n times and a step-like movement on a second width basis at one time subsequent thereto, the second width being greater in comparison with the first microscopic width, the stage is displaced in a specified one-axis direction. Then, this process is repeated, thereby scanning the sample surface. More concretely, the control unit is capable of controlling the stage movement so that the following operation is implemented: Employing, as the unit, (n−1)-times step-like style movements on the basis of a width of 1/n (n: an integer) of the irradiation spot spacing and the subsequent one-time step-like style movement on the basis of (a width between both ends of the excitation spot group+the first width), the movement in the irradiation spots-arranged direction is executed, and this process is repeated thereby scanning the sample surface.

It is desirable that fetching of the signal from the converging/detecting unit should be executed while the stage is being displaced in a direction perpendicular to the plurality of irradiation spots-arranged direction.

The unit for forming the plurality of irradiation spots is required to form the plurality of irradiation spot-portions simultaneously. In order to image-form the lights onto the sample surface, there is employed a condenser lens the data of which is as follows: The numerical aperture is 0.7 or more, the effective field-of-view is 1.0 mm or more, and the difference between the sample surface and the lens tip is 0.7 mm or more.

The unit for forming the plurality of irradiation spots can also be configured as follows: The unit includes a plurality of optical anisotropic media the lengths of which in the optical axis direction differ from each other or a plurality of optical anisotropic media the crystalline-axis directions of which differ from each other, and a plurality of wavelength plates located between the adjacent optical anisotropic media.

The unit for forming the plurality of irradiation spots can also be configured as follows: The unit includes a device where the plurality of optical anisotropic media and the plurality of wavelength plates are located alternately. Moreover, a length of each optical anisotropic medium in the light-travelling direction is equal to about one-half of a length of an optical anisotropic medium located immediately preceding thereto.

The unit for forming the plurality of irradiation spots may also be configured as follows: The lights from the excitation light-sources are scanned and launched in sequence into one ends of a plurality of aligned optical fibers, and light-emitting ends of the optical fibers are located on a straight line, thereby forming the plurality of irradiation spots.

Also, it is preferable that there should be provided a function of executing an intensity correction for each detection signal of the respective irradiation spots.

It is an object of the present invention to provide a technology for detecting weak fluorescent lights at a high-speed, with a high-resolution and with a high-sensitivity with reference to a target to be detected that requires 2-dimensional large number of lines of resolution. Also, It is another object thereof to provide, using this technology, a technology for inspecting a DNA with a high-sensitivity and at a high-speed.

In order to accomplish the above-described objects, the present invention employs the following methods and units:

The target object having a fluorescent characteristic is irradiated with multi-spot excitation lights including a large number of M microscopic spots. Fluorescent lights generated by the excitation lights from the respective multi spots are separated from the excitation lights. Then, fluorescent light images emitted from the target object are detected using a plurality of weak light detecting devices allowing the photon counting to be executed. This makes it possible to detect even an extremely weak fluorescent light. Photon signals obtained from the respective detecting devices are each photon-counted individually, then individually storing the photon-counted numbers Npm detected by the respective detecting devices. In addition, positions of the multi-spot lights and a position of the target object are changed relatively using a driving system and the like, then storing in sequence the photon-counted numbers from the respective detectors. Storing and collecting in this way the photon-counted number data over a desired range on the target object makes it possible to construct the fluorescent light picture from the collected data.

Also, sheet-shaped excitation lights are used instead of the above-described multi-spot lights. Fluorescent lights, which have been generated from irradiation areas obtained by the irradiation with the sheet-shaped excitation lights and having a long and narrow configuration, are separated from the excitation lights. Then, fluorescent light images emitted from the target object are detected using the plurality of weak light detecting devices allowing the photon counting to be executed. Photon signals obtained from the respective detecting devices are each photon-counted individually, then individually storing the photon-counted numbers Npm detected by the respective detecting devices. In addition, positions of the irradiation areas resulting from the sheet-shaped excitation lights and having the long and narrow configuration and the position of the target object are changed relatively, then storing in sequence the photon-counted numbers from the respective detectors. Storing and collecting in this way the photon-counted number data over a desired range on the target object makes it possible to construct the fluorescent light picture from the collected data.

By executing the irradiation with the multi-spot lights or the sheet-shaped excitation lights and detecting the fluorescent lights from M pixels simultaneously, it becomes possible to spend a time of M to 2M μsec per pixel in the case of trying to detect the 6000×6000 pixels in 1 minute. Here, the case has been described previously in the conventional problems. For example, assuming M=50, this time becomes equal to 50 to 100 μsec. This condition makes it possible to solve the previously-described problem concerning the delay in the fluorescent light generation. Also, the following reason permits the dynamic range to be ensured and the high-sensitivity detection to be executed.

Namely, the previously-described per-pixel detecting time of the order of 1 μsec shortens a detecting time that is long enough for a photo counting measuring time needed to execute the high-sensitivity detection, thereby making it difficult to ensure the dynamic range. This is attributed to the fact that, since the pulse-width of a photon pulse signal generated when one photon is detected is equal to tens of n seconds, only a signal of, at most, tens of pulses can be detected within the time of 1 μsec. Also, even if, in such a short time, an attempt is made to detect the fluorescent light intensity in an analogue manner, frequency characteristics of the detecting circuit make it difficult to execute the detection in a state where a sufficient dynamic range has been ensured.

Employing, as the above-described target object, a sample obtained from coupling a fluorescent molecule-added DNA fragment with a DNA corresponding thereto, the inspection is executed in the following way: In the case where the target to be inspected is, as an example, a DNA chip, a target that results from adding a desired fluorescent material to a DNA fragment formed from the target to be inspected, i.e., a DNA, is hybridized with the DNA chip at first. Then, the hybridized DNA chip to be inspected is irradiated with the multi-spot excitation lights including the large number of M microscopic spots. Fluorescent lights obtained by the irradiation from the multi spots are separated from the excitation lights. Next, separated fluorescent light images emitted from the DNA chip are detected using the plurality of weak light detecting devices allowing the photon counting to be executed. Moreover, photon signals obtained from the respective detecting devices are each photon-counted individually, then individually storing the photon-counted numbers Npm detected by the respective detecting devices. In addition, positions of the multi-spot lights and a position of the DNA chip are changed relatively, then storing in sequence the photon-counted numbers from the respective detectors. In this way, the photon-counted number data is stored and collected over a desired range on the DNA chip so as to construct the fluorescent light picture from the collected data, thereby inspecting the DNA.

The use of the sheet-shaped beams instead of the multi-spot lights also makes it possible to execute the DNA inspection by detecting the fluorescent material added to the target DNA in much the same way as explained in the above-described fluorescent light detection using the sheet-shaped beams.

A multi-spot aperture or a long and narrow aperture that permits only a multi-spot image or a sheet-shaped long and narrow area image to pass through is located at a focal point achieving position of fluorescent light images from the above-described target object surface, thereby performing the confocal point detection, the focal point achieving position being situated at a position at which the diameters of the multi-spot excitation lights or the sheet-shaped excitation lights with which the target object is irradiated become minimum-focused diameters. This makes it possible to obtain the confocal point image having a high signal-to-noise ratio. Namely, it becomes possible to detect, without being subjected to the influence from a fluorescent light noise and thus with a low-noise, the fluorescent lights at the multi-spot positions to be detected or the fluorescent lights at the sheet-shaped beam positions to be detected. Here, the fluorescent light noise exists in the background of substances such as a fluorescent material existing in optical paths other than the above-described positions to be detected. If the sample toward which the fluorescent light detection is performed exists within a 2-dimensional plane, relative positions between the multi spots and the sample are changed within the plane, then performing the confocal point detection. This method allows the high signal-to-noise ratio fluorescent light detection or DNA inspection to be executed in a state of being scarcely subjected to the influence of a noise by a fluorescent material existing outside the plane.

In the above-described fluorescent image detection using the multi-spot lights, the relative positions between the multi spots and the sample are changed in at least one direction out of three directions in total, i.e., two directions within the target object surface and the remaining one direction perpendicular to the target object surface. In particular, in the case of the above-described confocal point detection, the relative position of the target is changed in the optical axis direction from the position at which the diameters of the multi spots or the sheet-shaped beams become the minimum-focused diameters, then determining the focal point achieving position from the obtained variation in the fluorescent light image intensity. Accordingly, from the fluorescent light intensity at this position and toward a target having irregularity on its surface, it becomes possible to obtain the accurate fluorescent light intensity information, surface irregularity information, or information on the 3-dimensional positions emitting the fluorescent lights.

As having been pointed out in the problem in the case of the above-described conventional one-spot excitation light, the larger the number of the multi-spot lights becomes, the more advantageous it becomes to detect the fluorescent light image at a high-speed. Setting M to be 10 or larger increases, up to hundreds, the maximum photon-counted number detectable within this time, thereby becoming effective in implementing the high-sensitivity characteristic and the broad dynamic range. Since an even higher-speed characteristic is implemented in the DNA inspection and the like, providing the plurality number of spots exhibits an outstanding effect. Making M equal to 50 or more exhibits a more outstanding effect. Namely, setting M to be 50 or larger makes it possible to detect, for example, the 6000×6000 pixels in spending tens of A seconds per pixel, thereby allowing all the pixels to be detected within 1 minute.

The above-described multi spots are arranged on a 1 or 2-dimensional straight line in order to accomplish the following purposes: Detecting the multi spots using a plurality of detecting devices, above all, a plurality of detecting devices arranged on a 1 or 2-dimensional straight line, and causing the detected plural pieces of information to correspond to the position information of the target or the DNA chip so as to output the detected information as the fluorescent light image.

The relative positions between the multi-spot excitation lights or the sheet-shaped excitation lights and the target are changed, and a period during which this movement by the amount of one pixel is executed is set to be Td. At this time, a value $\alpha Td/\Delta t_0$ is determined as follows: First, a value $Td/\Delta t_0$ is determined by dividing the period Td by $\Delta t_0$. Here, $\Delta t_0$ denotes the pulse-width of the previously-described photon counting signal at the time of detecting a single photon. Then, the value $\alpha Td/\Delta t_0$ is determined by multiplying $Td/\Delta t_0$ by a desired coefficient $\alpha$ that is larger than 0.1 and smaller than 1. Moreover, employing, as a judging criterion, a condition that this value has reached the above-described photon-counted number Npm, i.e., at the time of $\alpha Td/\Delta t_0 \geq Npm$, the detection is executed in a state of weakening the fluorescent light detection intensities so that the photon counting becomes executable. This weakening is performed using such a method as changing the intentities of the multi-spot excitation lights or the sheet-shaped excitation lights. Namely, in the point of the accuracy, it is impossible to execute the photon counting that is more than a times as large as the value obtained by dividing the per-pixel detecting time by the photon pulse time-width. Accordingly, in the following way, the photon counting value is adjusted to the value toward which the photon counting is effectively executable: Weakening the excitation lights, shortening the excitation light irradiation time to effectively lower the excitation light intensities, or lowering the gain of the detecting device sodas to weak the detected fluorescent lights.

The above-described multi-spot excitation lights or sheet-shaped excitation lights are converted into multi-color lights having 2 or more of wavelengths. This increases the information on the fluorescent light detection, thereby enhancing the fluorescent light detecting function and the DNA detecting function.

Also, a time during which the above-described photon pulse signal is being positioned at a high level is addition-measured during a time $\beta Td$ that is less than the per-pixel detecting time Td. When setting the value of this time to be Th', it is judged whether or not a condition $Th' \geq \gamma \beta Td$ is satisfied with reference to a predetermined $\gamma$ that is smaller than 1. If this inequality should be satisfied, there is employed a result obtained by integrating the output signal from the detecting device in an analogue-style integrating circuit. This makes it possible to perform the detection toward stronger fluorescent lights as well. Namely, even in the case of detecting the strong fluorescent lights the photon counting of which is impossible, executing the analogue-style integration allows the strong lights to be detected. What is more, making the analogue-style detecting time equal to Td or less allows all the pixels to be detected without changing the per-pixel detecting time. As a consequence, it becomes possible to execute the detection with a high-resolution and at a high-speed over a broad dynamic range ranging from the weak fluorescent lights necessitating the photon counting to the strong detection intensities necessitating the analogue integrating detection based on the above-described integrating circuit. Also, as a detecting method where the above-described $\alpha$ is equivalent to 1, there exists the following method: The photon counting and the analogue integrating detection are executed in parallel simultaneously so as to compare and judge both results obtained, then employing one of the detected results.

Also, a laser light-source is used as the above-described excitation light-source. A multi-spot generating hologram or a sheet-shaped beam generating hologram is located within the laser resonator, and the multi spots are generated using the strong laser light within the laser resonator. Usually, the optical energy within the laser resonator is more than 10 times as high as the emitting beam energy. In an ordinary laser resonator, the reflectance of a mirror at the emitting window is set to be substantially 90%, and the remaining substantially 10% is extracted as the emitting light. The reflectance at the emitting window is made equal to 100% so as to confine the light within the resonator, and the hologram is located in an optical path within the resonator. This method allows substantially 10% of the hologram, diffraction efficiency to be utilized as the multi-spot lights or the sheet-shaped beams. As a result, it is possible to obtain the multi-spot lights or the sheet-shaped beams the intensities of which are almost 1 times higher as compared with those in the conventional case where the hologram is located in a laser-emitting optical path. Consequently, it becomes possible to execute the high-speed and high-sensitivity fluorescent light detection and DNA inspection.

The present invention permits a laser light emitted from a laser light-source to be converted into the multi-spot lights with a exceedingly high-efficiency and without being wasted. At the same time, the present invention makes it possible to extremely lessen the variation among the respective multi-spot lights. As a consequence, using the multi-spot lights, it becomes possible to execute the high-speed and high-accuracy confocal point detection. Also, using the multi-spot lights, it becomes possible to execute the high-speed and high-accuracy fluorescent light detection and DNA inspection.

The present invention allows even the analogue integrating detection to be executed, thereby making it possible to execute the detection having a exceedingly broad dynamic range. Namely, it becomes possible to even detect the fluorescent light image of, for example, the 6000×6000 pixels in the dynamic range of $2^{16}$ in the detecting time of 1 minute. As a result, it becomes possible to detect targets to be inspected, such as the DNA chip, in the detecting time of an order of 1 minute. This eventually makes it possible to detect, in a short time and precisely, a large quantity of samples to be inspected that are collected in a widely executed group checkup.

Also, the present invention is not only applied to the DNA inspection, but is widely used for a fluorescent light detecting microscopic method. The present invention tremendously shortens the times that have been required for the conventional observations and inspections. Namely, it becomes possible to detect, in a short time, even a weak light toward which only several photons can be detected. Also, it becomes possible to execute, in a short time and with a high-accuracy, the detection over a broad range ranging from the weak light to the strong light to be detected.

BRIEF DESCRIPTION OF THE DRAWINGS

FIGS. 6A, 6B, 6C, 6D, 6E are diagrams for explaining the movement of spot fluorescent light images at the time of fixing a wavelength selection beam splitter;

FIG. 41A is a front view for illustrating the configuration of an embodiment of the multi-spot light forming unit according to the present invention;

FIGS. 41B, 41C, and 41D are partially enlarged diagrams of FIG. 41A;

DESCRIPTION OF THE EMBODIMENTS

Figure 1:
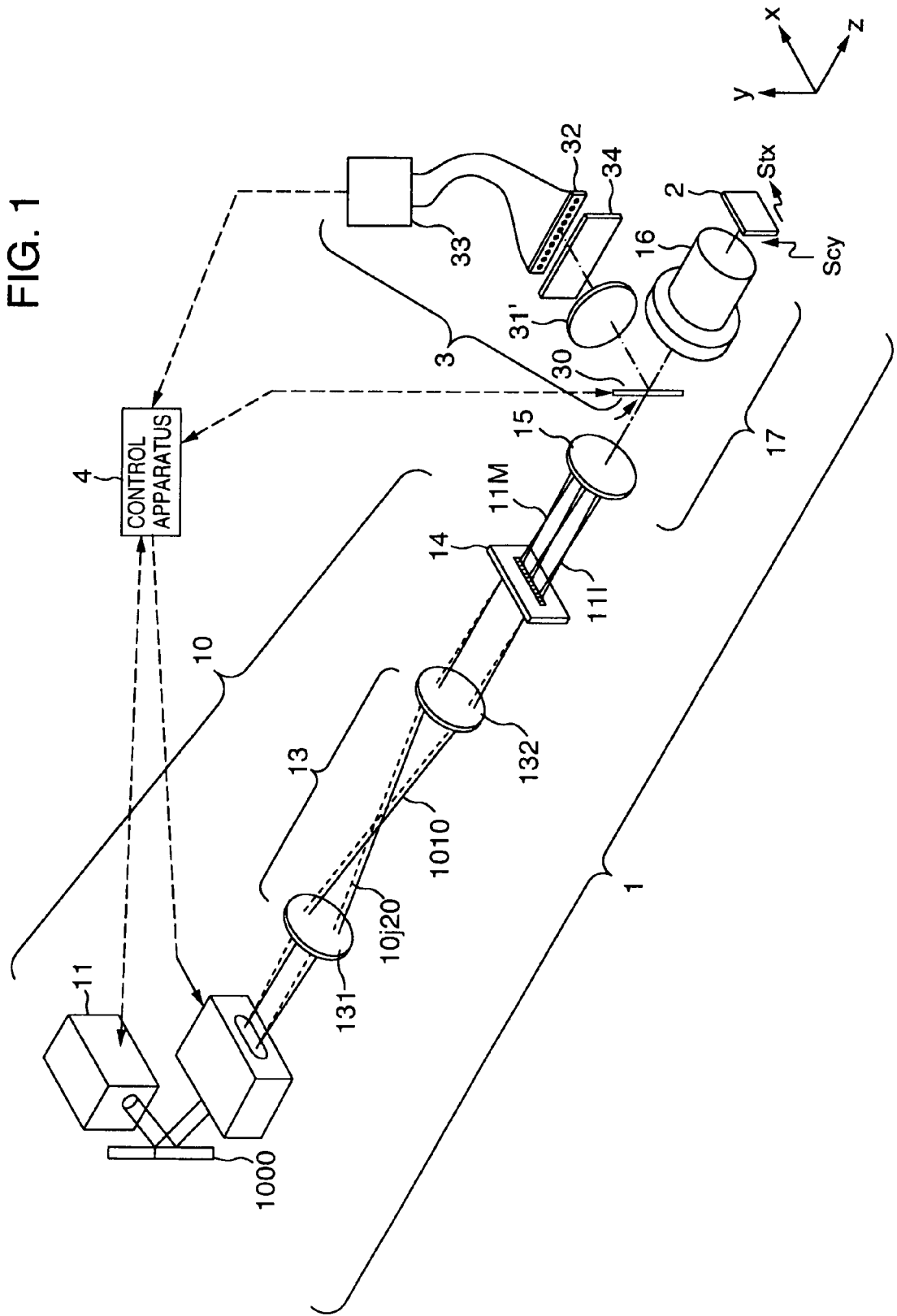
FIG. 1 is a diagram for illustrating an embodiment in the present invention.

FIG. 1 is a diagram for illustrating an embodiment in the present invention. The reference numerals denote the following configuration components: 1 A multi-spot excitation lights-irradiating system for forming multi-spot excitation lights to irradiate a DNA chip 2 with the excitation lights so that a fluorescent light detection can be executed, 3 a fluorescent light detecting system for detecting fluorescent lights generated by the multi-spot excitation lights, 11 an excitation light-source including an excitation light light-source and an excitation light beam forming optical system. A He—Ne laser light beam is formed into a desired longitudinal-to-transverse ratio of the beam diameter by two cylindrical lenses having different focal lengths, then being launched into an AO deflector 12 through a mirror 1000. The AO deflector 12 includes a terminal of a frequency-$\omega$ high-frequency voltage applied to a quartz oscillator, and an input terminal of an amplitude signal the frequency $\omega_v$ of which is lower than the frequency $\omega$.

The signal with the frequency $\omega$, which is transmitted from a control apparatus 4, has a frequency band in a range of $\omega \pm \omega_0$. Changing the frequency results in a change in the diffraction angle of the excitation light incoming into the AO deflector 12. Also, an inputting of the amplitude signal $\omega_y$ from the control apparatus 4 brings about a change in the diffraction efficiency, thereby making it possible to control the diffraction light intensity. The diffraction light having passed through the AO deflector is separated from its 0th light (not illustrated) (the 0th light is light-shielded). Then, a lens system 13 including two lenses 131, 132 of focal lengths $f_1, f_2$ irradiates a microlens array 14 with the separated diffraction light in a desired beam diameter. Changing the frequency of the AO deflector 12 changes the angle of the excitation light incoming into the microlens array 14, but causes no change in the position thereof.

Figure 4:
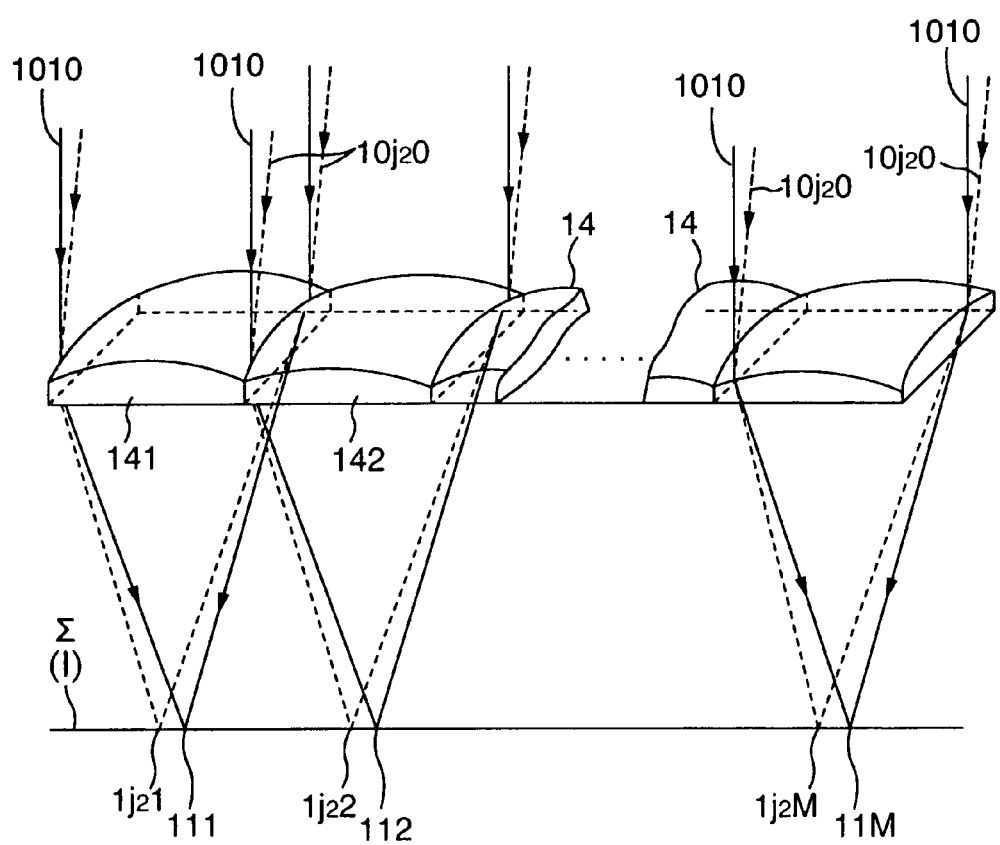
FIG. 4 is an embodiment-illustrating diagram in the present invention, which indicates multi-spot generation by a microlens array.

FIG. 4 is an enlarged detailed view of the microlens array 14. Microscopic microlenses composed of glass are arranged in a 1-dimesional configuration in a large number of 32 to 256. Let's explain the light incoming therein: For example, lights 1010 represented by solid-lines pass through the respective microlenses 141, 142, . . . , then image-forming microscopic spots 111, 112, . . . , 11M on a straight line e on a focal point plane $\Sigma$. As illustrated by dotted-lines in FIG. 4, changing the frequency of the AO deflector 12 changes the angle of the excitation light incoming into the microlenses. As a result, the positions of the microscopic spots on the straight line 1 are changed to the positions as indicated by $1j_21$, $1j_22$, . . . , $1j_2M$.

As is illustrated in FIG. 1, through the use of a lens 15 and an objective lens 16, a fluorescent material added to targets hybridized with the DNA chip 2 is irradiated and excited with the microscopic-spot array 111, 112, . . . , 11M formed on the focal point plane $\Sigma$ of the microlens array 14. The focusing of the objective lens 16 is achieved so that the minimum beam diameter is formed on a glass surface $\Sigma 1$ or $\Sigma 2$ to which the targets have been attached (Concerning the details, refer to FIG. 33).

Figure 2:
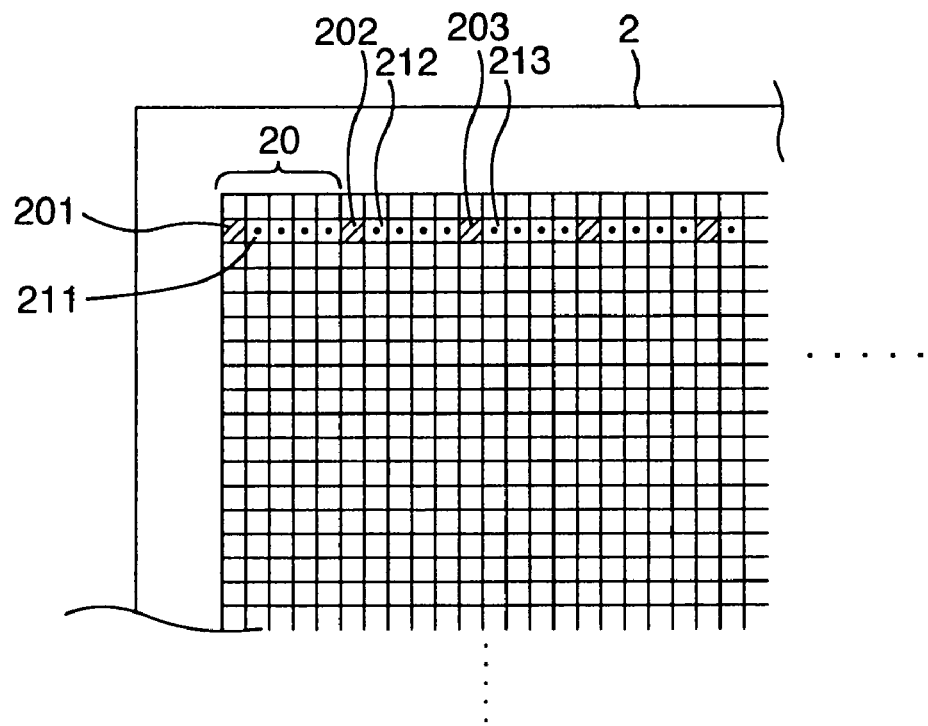
FIG. 2 is an embodiment-illustrating diagram in the present invention, which indicates multi-spot irradiation.

FIG. 2 illustrates the details of a surface structure of the DNA chip 2. Square-shaped minimum units 201, 211, 202, 212 and so on, which are indicated by longitudinal and transverse thin lines, represent detection pixels. In the drawing, a cell 20 is equivalent to 5×5 pixels (indicated by a bold line). A fragment of the same DNA information is planted in one cell. Consequently, a target having the same DNA fragment structure is hybridized with this cell.

The reason why one cell is divided into a plurality of pixels is as follows: When a foreign substance such as a protein is mixed in one cell, in some cases, an excitation light incoming into this protein generates a large-intensity fluorescent light. The dimension of such a foreign substance is usually equal to, at most, several μm. Accordingly, if the pixel dimension is equal to several $\Delta m$ and the cell dimension is equal to 10 μm for example, and if a method as described later allows the foreign substance position to be detected and be separated within the cell of 10 μm, it becomes possible to precisely determine the magnitude of the fluorescent light in accordance with the information on a portion other than the foreign substance portion.

Figure 3:
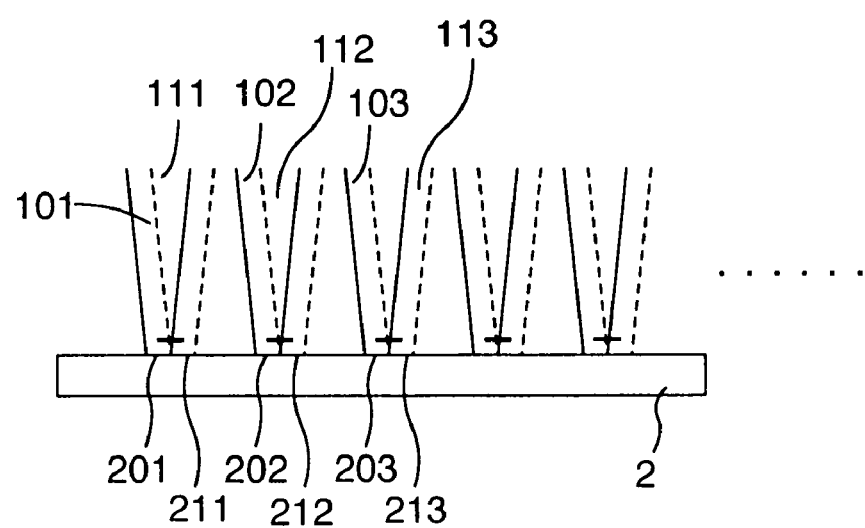
FIG. 3 is an embodiment-illustrating diagram in the present invention, which indicates the movement of the multi-spot irradiation.

FIG. 3 illustrates a side view of the DNA chip. The configuration given in this drawing is that the hybridized targets are mounted in a state of being naked on a glass substrate. This state is presented in some cases, and there are other cases where, as will be described later, the hybridized targets are sandwiched between glass substrates. In any case, the microscopic excitation light spots are converged onto the plane on which the targets exist. The light-converged diameter is substantially equal to the dimension of the pixel to be detected, i.e., the square-shaped minimum unit illustrated in FIG. 2.

At the initial frequency of the AO deflector 12, there has been obtained the diffraction light represented by solid-lines in FIG. 1. At this time, as illustrated in FIG. 3, the pixels 201, 202, 203, . . . , 20M on the DNA chip are irradiated with the excitation light spot array as indicated by 101, 102, 103, . . . , 10M. This irradiation, as will be explained later, allows fluorescent lights to be detected from the respective pixels. The irradiating time of the excitation light spots is equal to a time Δt (several to hundreds of μseconds) that is larger than the fluorescent light attenuation time. In the present embodiment, the irradiating time is equal to 60 μs.

Moreover, after the lapse of 60 μs, changing the frequency of the AO deflector 12 gives rise to the change in the diffraction angle of the excitation light. Then, as illustrated in FIG. 1 and FIG. 4, lights $10j_20$ denoted by dotted-lines are launched into the microlens array 14. As a result, as illustrated in FIG. 3, the DNA chip is irradiated with the excitation light spot array as indicated by 111, 112, 113, . . . , 11M. This irradiation allows fluorescent lights to be detected from pixels 211, 212, 213, . . . , 21M. In this way, the irradiation with the M multi spots is executed in sequence with a shift on a pixel-pitch basis. When the shifts by the amount of j pixels have been finished, it turns out that the fluorescent lights by the amount of jM pixels have been detected all.

Next, referring to FIG. 1, the explanation will be given below concerning the embodiment of the fluorescent light detection. A beam splitter 30 located between the lens 15 and the objective lens 16 is a wavelength separating beam splitter. In the present embodiment, the wavelength of the He—Ne laser light from the excitation light-source is equal to 633 nm. The fluorescent material added to the targets on the DNA chip is Cy5, and the wavelength of the fluorescent lights to be detected lies in proximity to 670 nm.

The wavelength separating beam splitter 30 permits the 45°-incident excitation light at the wavelength of 633 nm to pass through by substantially 100%, and causes the 45°-incident fluorescent lights at the wavelength of 670 nm to be reflected by substantially 100%. The beam splitter, however, reflects the 633 nm excitation light as well by a exceedingly slight amount. The exceedingly slight amount of reflection becomes a problem since the fluorescent lights are extremely weak. Accordingly, in the embodiment in FIG. 1, an interference filter 34, which has its central wavelength characteristic at 670 nm and the half-value width of which is equal to about 15 nm, is inserted into the fluorescent light detecting system 3 so as to cause the interference filter to light-shield the excitation light leakage. Incidentally, the component 34 is not limited to the interference filter. Thus, it is allowable to use so-called a color filer for permitting a certain value or more of wavelength light to pass through and causing a certain value or less of wavelength light to be light-shielded. Also, the combined use of the color filer and the interference filter is allowable. Hereinafter, the explanation will be given concerning the embodiments, using the interference filter alone for the simplicity of the explanation.

Figure 5:
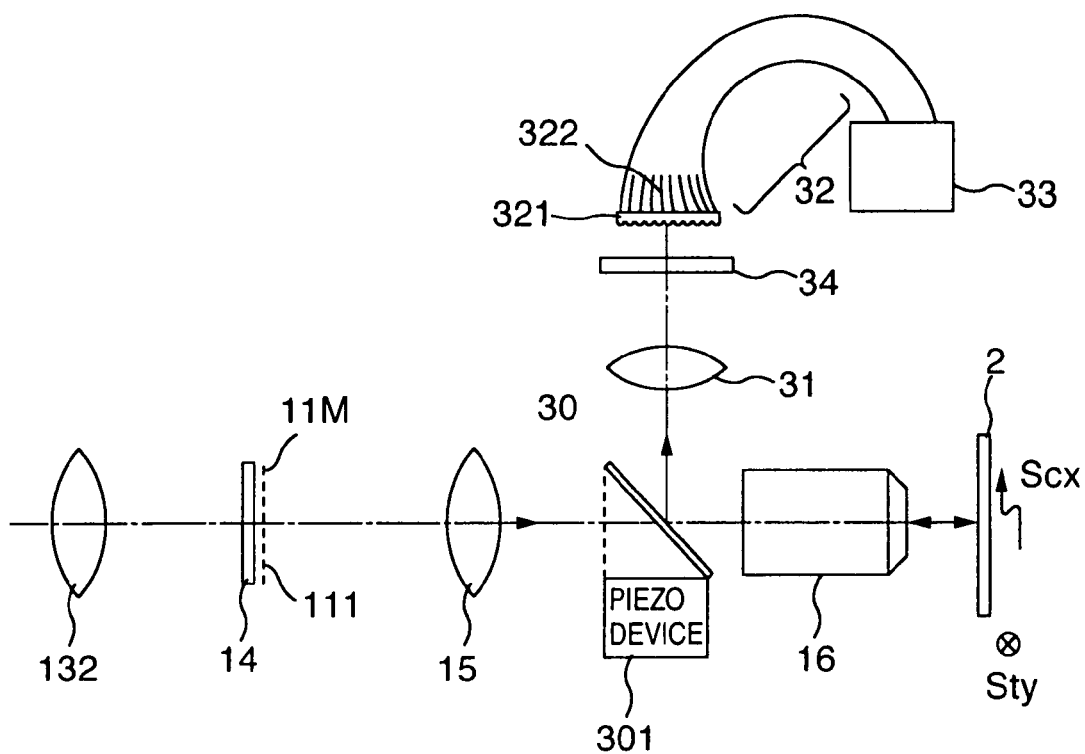
FIG. 5 is an embodiment-illustrating diagram in the present invention, which is a diagram for explaining the embodiment in FIG. 1.

Next, the explanation will be given below concerning the following: Changes in the positions of detected fluorescent light images when the positions of the multi-spot excitation lights on the DNA chip are changed using the AO deflector, and corrections of the position changes needed in order to execute the detection with the fixed detector. The wavelength separating beam splitter 30 in FIG. 1 performs the corrections of the position changes as well. FIG. 5 illustrates the main portion in FIG. 1, and the same reference numeral as that in FIG. 1 denotes the same component. The wavelength separating beam splitter 30 is driven by a piezo device 301 having a high resonant frequency characteristic of 5 to 10 kHz, and is configured to perform a microscopic rotation with the y axis as its center.

FIGS. 6A to 6E and FIG. 7 are diagrams for explaining the role of this microscopic rotation, and the same reference numeral as that in FIG. 1 denotes the same component. By the deflection signal inputted into the AO deflector 12 from the control apparatus 4, the respective positions of the multi excitation microscopic spots 1011, 1021, . . . , 10M1 on the DNA chip 2 in FIG. 6C are changed to 1012, 1022, . . . , 10M2 in sequence on the one-pixel basis. At this time, assuming that the wavelength separating beam splitter 30 performs no rotation, as illustrated in FIG. 6D, multi fluorescent light points 1211, 1221, . . . , 12M1 on a fluorescent light detection plane $\Sigma_{PH}$ that is located at a position conjugated with the DNA chip are changed to 1212, 1222, . . . , 12M2 on the one-pixel basis as well.

Figure 7:
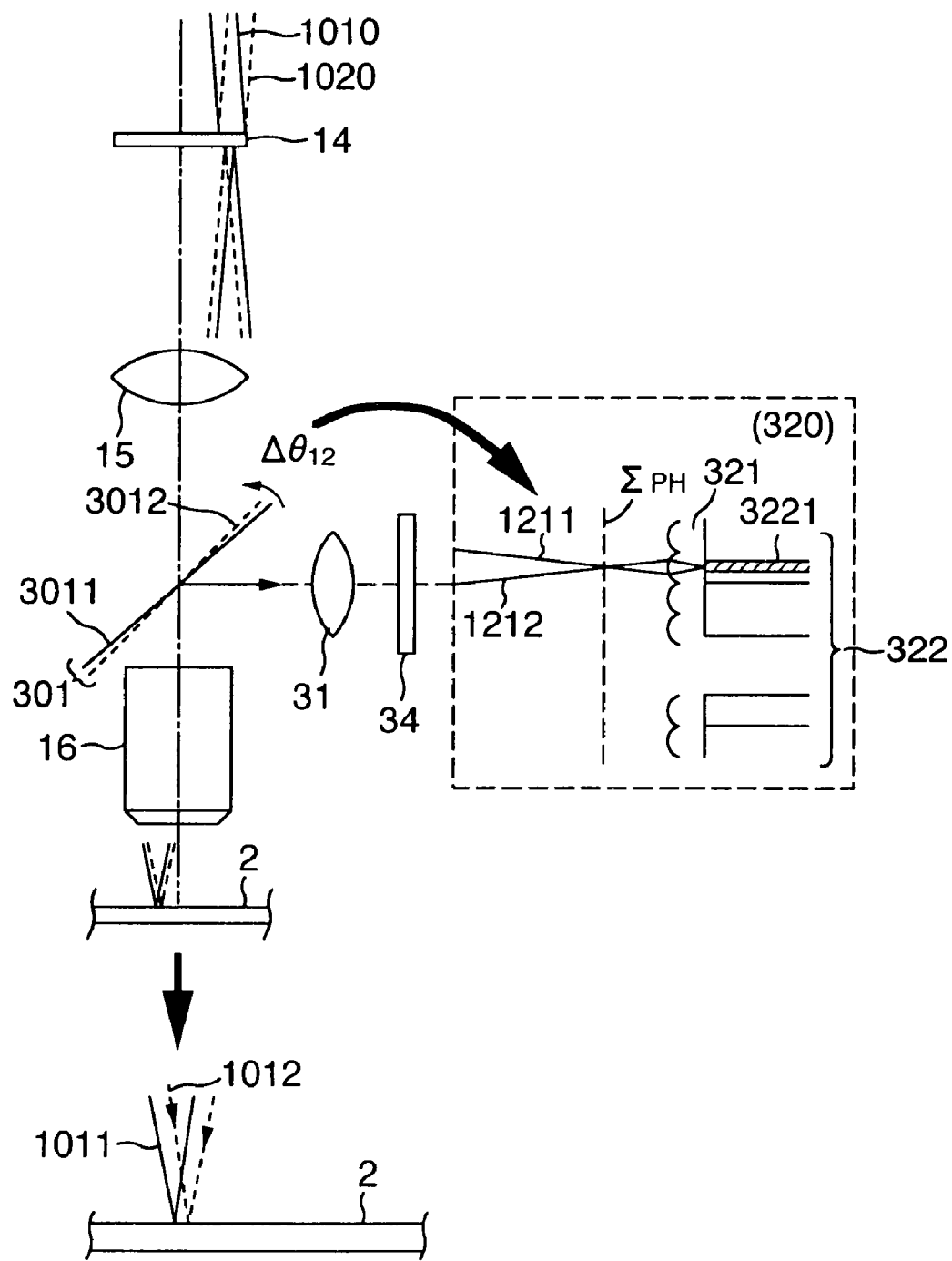
FIG. 7 is a diagram for explaining the movement of the spot fluorescent light images at the time of deflecting the wavelength selection beam splitter.
Figure 8:
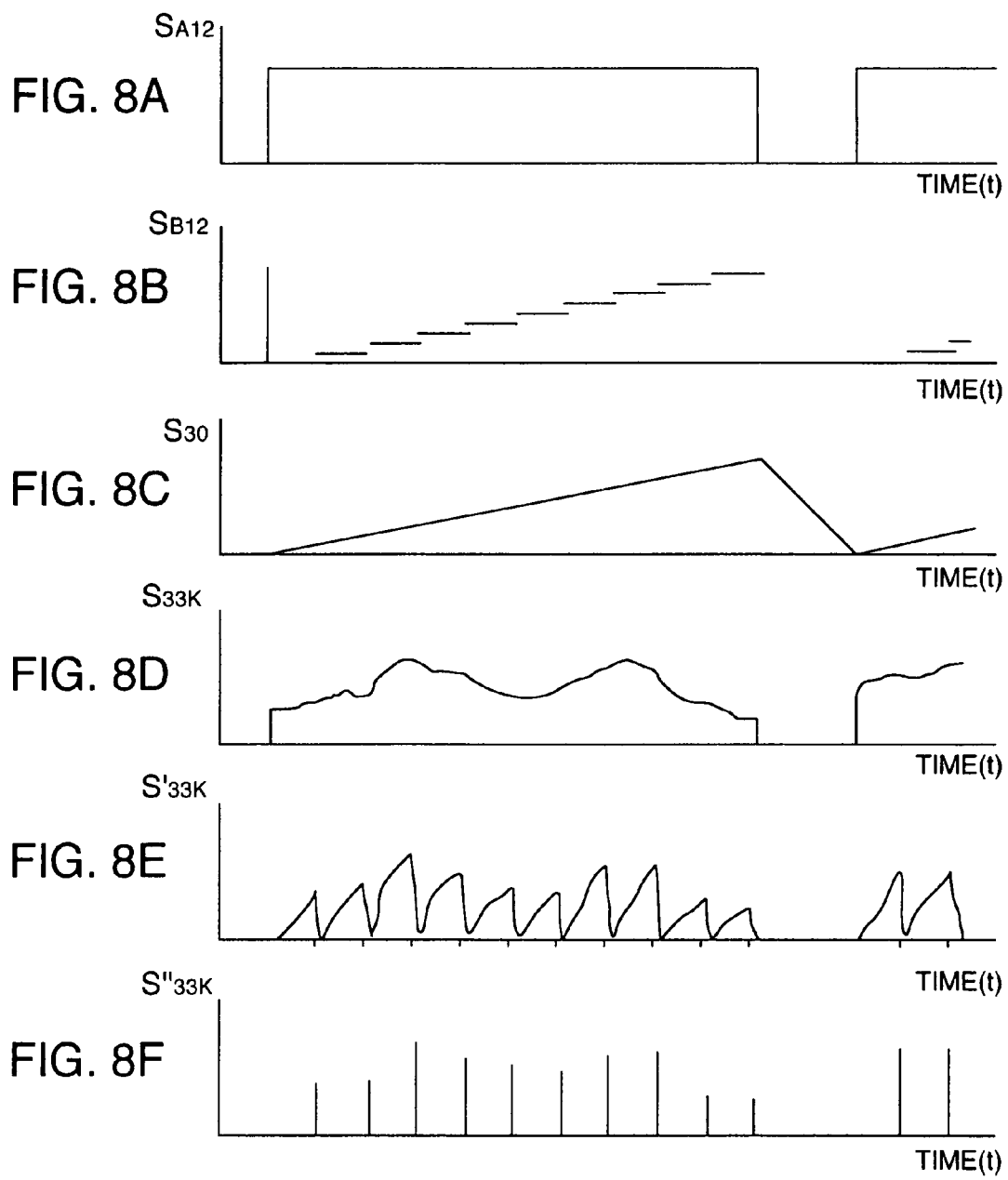
FIGS. 8A to 8F are diagrams for illustrating operations, detection signals and so on of the respective components in FIG. 1.

The fluorescent light spot image 1212 on the fluorescent light detection plane, as illustrated in the drawings, is image-formed as a 1212 point onto an end of one optical fiber in an optical fiber bundle 322 by a fluorescent light detecting microlens array 321, then being launched into the one optical fiber. The one optical fiber is formed of a core 3221 through which a light passes and a portion 3222 for protecting the core. The diameter of the core through which the light passes is somewhat larger than that of the (multi) fluorescent light point 1211 on the fluorescent light detection plane $\Sigma_{PH}$. If, however, the wavelength separating beam splitter 30 performs no rotation, the 1211 point is displaced to 1212, 1213, 1214 . . . (FIG. 6E) by the driving of the AO deflector 12, then being shifted from the optical fiber light-receiving end. This makes the detection impossible. Accordingly, as illustrated in FIG. 7, using the piezo device 301 having the high resonant frequency characteristic, the wavelength separating beam splitter 30 is driven so that it performs the microscopic rotation.

Namely, in FIGS. 6A to 6E in the case of no microscopic rotation, the fluorescent light microscopic spot image 1211 is displaced to the different locations 1212, 1213, 1214. On the other hand, as illustrated within a dotted-line frame in FIG. 7, driving the beam splitter to perform the microscopic rotation permits the spot to come onto substantially the same position on the plane $\Sigma_{PH}$.

FIGS. 8A to 8F illustrate the relative time variations among the following respective signals: $S_{A12}$, an ON-OFF signal or an intensity modulation signal of the above-described AO deflector 12, $S_{B12}$, the deflection signal of the AO deflector 12, $S_{30}$, a driving signal of the piezo device 301 for deflection-driving the wavelength separating beam splitter 30, $S_{33K}$, a fluorescent light detection signal detected by one k-th photomultiplier tube 33 through a fiber 32, $S'_{33K}$, a per-pixel image storage (integration) signal of the fluorescent light detection signal, and $S''_{33K}$, a per-pixel final result of this image storage (a value obtained by a sampling-and-holding of $S'_{33K}$ at a point-in-time before the image storing has been performed and the multi-spot excitation lights transfer to the excitation of the next pixel). In the embodiment of this graph, the multi-spot excitation lights are shifted in sequence on the one-pixel basis by the AO deflector 12, and in this way, one spot has been shifted in sequence by the amount of ten pixels.

In order to enhance a signal-to-noise ratio in the detection of each pixel, the number of this shifting need to be equal to 2 or more. The larger the number is, the more desirable it is to implement the enhancement of the signal-to-noise ratio. However, conditions such as restrictions on the apparatus's configuration components naturally impose an upper limit on the number. Nevertheless, making the number equal to 5 or more outstandingly reduces the influences of the scattered lights or the fluorescent lights accompanied by the foreign substance irradiation with the adjacent multi-spot excitation lights halfway in the optical paths.

As illustrated in FIGS. 8A to 8F, the frequency (the frequency of an ultrasound applied to an ultrasound quartz oscillator, i.e., the deflection angle of the deflector) signal S112 of the AO deflector 12 is changed in sequence in a step-like manner. During this change, the driving signal $S_{30}$ of the piezo device 301 for deflection-driving the wavelength separating beam splitter 30 is changed linearly in response to this change. The AO deflector 12 diffracts a light by an extremely slight amount of change of a transparent medium's refractive index caused by the ultrasound propagation. Meanwhile, the piezo device 301 drives the beam splitter 30 as a whole. As a result, there exists a difference in the frequency response characteristic between them. Consequently, the fast frequency signal $S_{B12}$ of the AO deflector 12 is formed into the step-like configuration and the slow driving signal $S_{30}$ of the piezo device is formed into the linear configuration.

Figure 9:
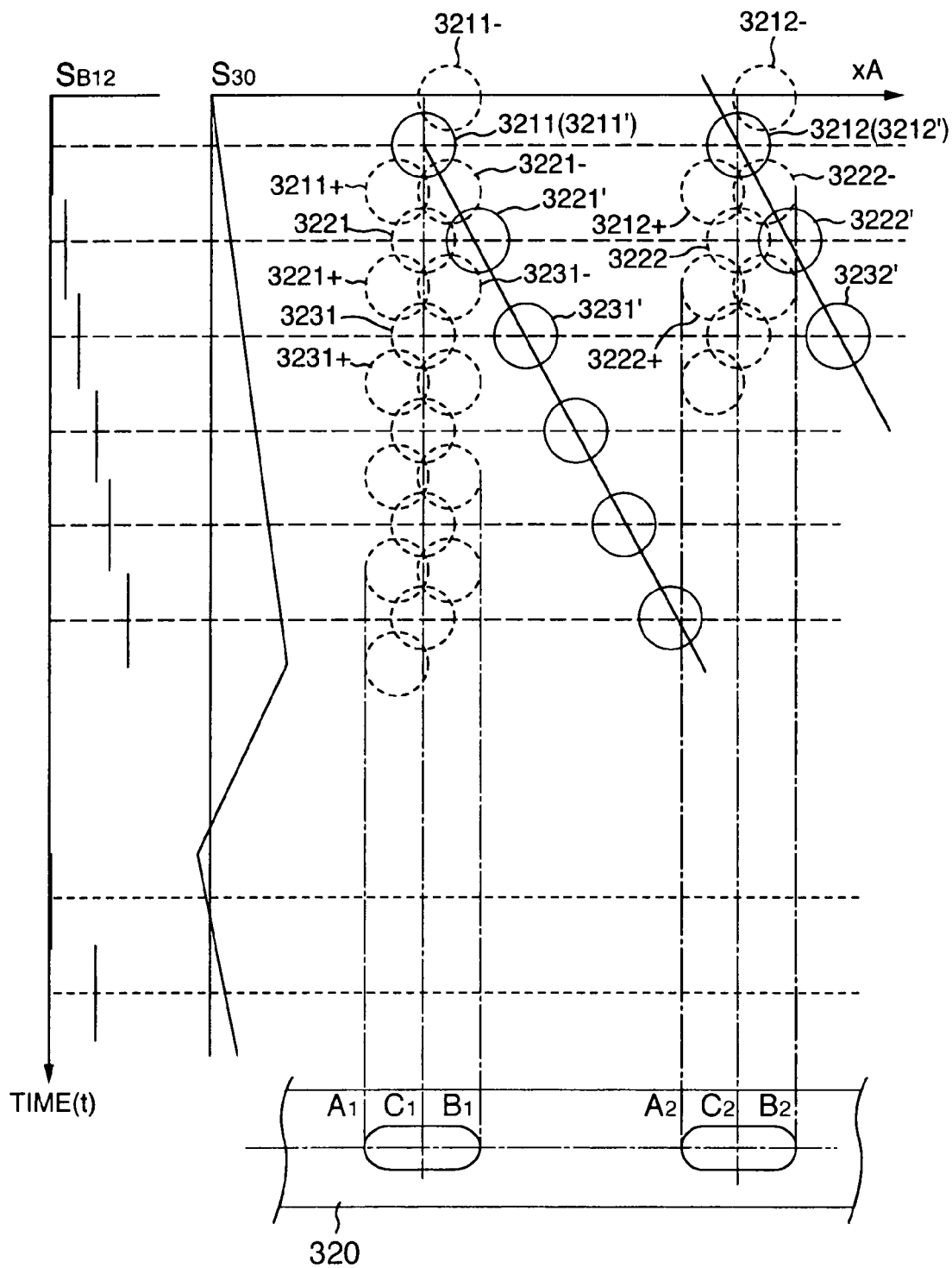
FIG. 9 is a diagram for illustrating the movement of the images on a fluorescent light image detection plane in the embodiment in FIG. 1.

FIG. 9 is a diagram for illustrating the positions of the fluorescent light spot images formed by these two signals on the fluorescent light detection plane $\Sigma_{PH}$. The change from the above to the below in this drawing represents the lapse of a time t. Two graphs on the left side indicate the changes of $S_{B12}$ and $S_{30}$. Although the number of the steps is equal to 10 in FIG. 8, it is equal to 5 in this drawing. Solid-line circles 3211', 3221', 3231', . . . that exist on the right side of the graph in FIG. 9 indicate the position shift of the fluorescent light detection multi-spot image in the case where, as was explained in FIGS. 6A to 6E, the position correction by the piezo device has not been performed yet. Incidentally, the right direction (transverse direction) in the drawing represents the arrangement direction $x_A$ of the spot array, and solid-line circles 3212', 3222', 3232', . . . indicate the position shift of the fluorescent light spot image adjacent to the above-described image. Moreover, dotted-line circles indicate the consequences obtained as the result of executing the position correction by the piezo device.

Namely, even when the AO deflector 12 had finished performing the step displacement of the excitation light and thus the excitation light has already stopped, the piezo device is still driving the deflection linearly. As a result, the corrected position of the fluorescent light spot image formed on the fluorescent light detection plane $\Sigma_{PH}$ is displaced as is indicated by $3211_-$, $3211$, $3211_+$ by a slight amount though, while the excitation light continues to stop (The corrected position of the adjacent fluorescent light spot image is displaced as is indicated by $3212_-$, $3212$, $3212_+$ by a slight amount, though).

Figure 10:
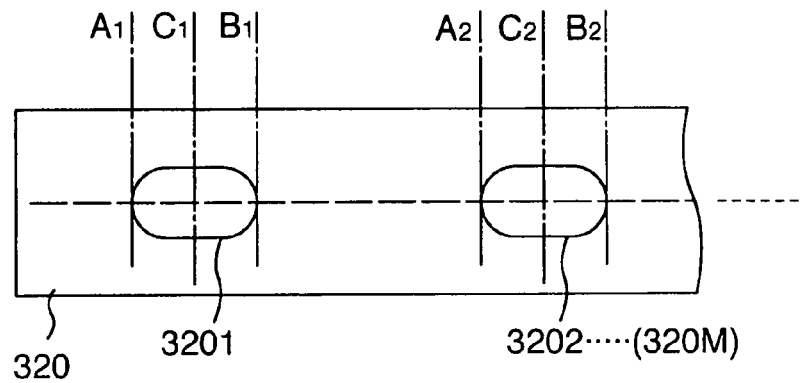
FIG. 10 is a diagram for illustrating light-receiving apertures on the fluorescent light detection plane in the embodiment in FIG. 1.

When the excitation light has been step-displaced to the next irradiation position on the DNA chip, and even if it continues to stop there, the corrected position of the fluorescent light spot image is displaced as is indicated by $3221_-$, $3221$, $3221_+$ by a slight amount, though (The corrected position of the adjacent fluorescent light spot image is displaced as is indicated by $3222_-$, $3222$, $3222_+$ by just a slight amount, though). In order to cover and detect this slight amount of displacement of the fluorescent light spot images, as illustrated in FIG. 10, there is provided an arrangement of ellipse-shaped apertures 3201, 3202, . . . , 320M on a fluorescent light detection light-receiving plane (or, a plane conjugated with the light-receiving plane) 320, the longer radius of the ellipse being in the spot array direction $x_A$. In the case of the above-described detection using the fiber, it is all right to set a condition that the fiber light-receiving end plane should include the ellipse.

Figure 11:
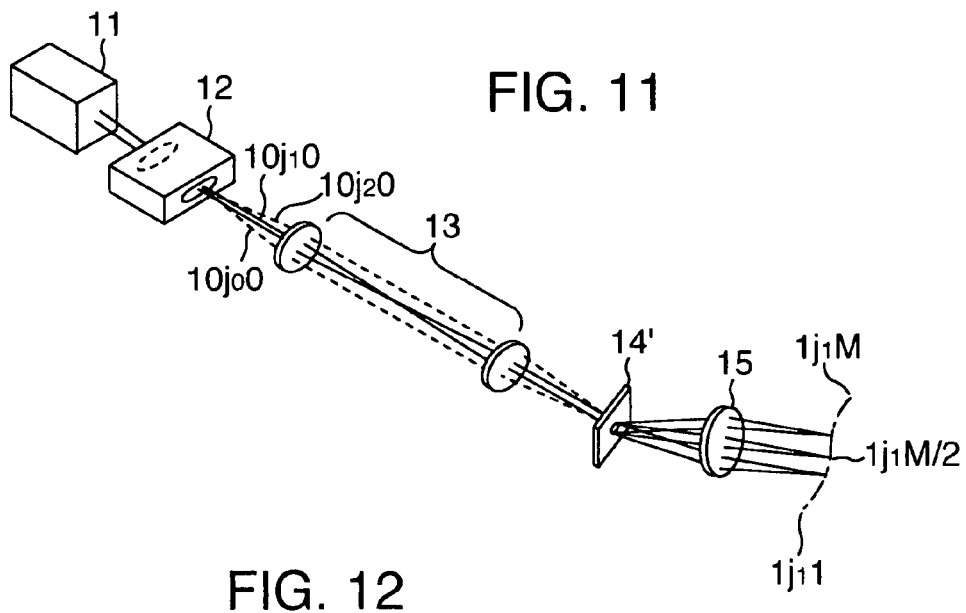
FIG. 11 is an embodiment-illustrating diagram in the present invention, where the multi spots are formed using a hologram.

FIG. 11 is a diagram for illustrating an embodiment in the present invention. The same reference numeral as that in FIG. 1 denotes the same component or the same function. In the present drawing, there is illustrated only a portion relating to the generation of the multi-spot excitation lights out of the entire apparatus in FIG. 1. The configuration components other than the portion are basically the same as those in FIG. 1. A reference numeral 14' denotes a multi-spot generating hologram.

Figure 12:
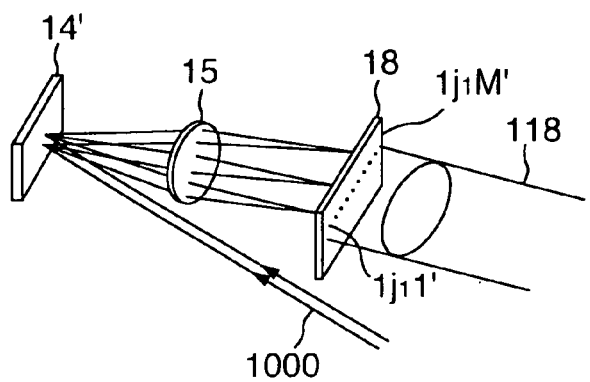
FIG. 12 is a diagram for illustrating a method of creating the hologram in FIG. 11.

FIG. 12 is a diagram for illustrating a method of creating the multi-spot generating hologram. As illustrated in FIG. 12, a laser light is irradiated with a mask 18 having pinhole array $1j_11'$, $1j_12'$, . . . , $1j_1M'$ apertures having hole diameters corresponding to dimensions of the multi-spot excitation lights. Then, the transmittance lights having passed through the mask are converged onto a hologram storage medium by a Fourier transformation lens 15. Next, the converged position is irradiated with a reference light 1000 from a somewhat oblique direction at an incident angle $\phi=\phi_0$ in a superimposed manner, thereby forming the Fourier transformation hologram at the above-described converged position.

In order to enhance the light utilization efficiency, there is employed a phase-modulation type storage medium. Also, random phases that are independent of the mutual positions of the respective apertures are added to the apertures. This addition is performed in order to avoid the following situation: The intensity of a 0th light at the central position (a position where the space frequency is equal to 0) on the Fourier transformation surface is increased up to an order-of-magnitude difference, and thus values such as the signal-to-noise ratio and the diffraction efficiency of the formed hologram become worse.

The hologram created in this way is used in the multi-spot excitation lights-generating system in the DNA inspecting apparatus in FIG. 11.

In FIG. 11, a laser light is launched into the AO deflector 12 and then passes through the lens system 13. Next, the hologram 14' that has been created by the above-described method is irradiated with the laser light at an incident angle $\phi_0$. An incident angle $\phi$ of the laser light launched into the hologram is set so that, at the center (the center of the deflection angle) of the driving frequency of the AO deflector 12, the incident angle $\phi$ becomes equal to the incident angle $\phi_0$ of the reference light 1000 toward the hologram surface at the time of creating the hologram by the method in FIG. 12. The irradiation of the hologram with the laser light in accordance with this setting, as illustrated in FIG. 11, reproduces, at $1j_11$, $1j_12$, . . . , $1j_1M$, a spot array that is the same as the pinhole array at the time of creating the hologram in FIG. 12.

Next, changing the frequency of the AO deflector brings about a slight amount of change in the incident angle into the hologram, thereby bringing about a slight amount of change in the angles of the multi-spot reproduced lights as well. As a result, it turns out that a position equivalent to the adjacent pixel is illuminated and excited. Accordingly, a sequential driving of the AO deflector makes it possible to execute the multi-spot excitation illumination of the DNA chip in the step-like manner, i.e., in such a manner that the position to be irradiated is changed in sequence on the one-pixel pitch basis.

Figure 13:
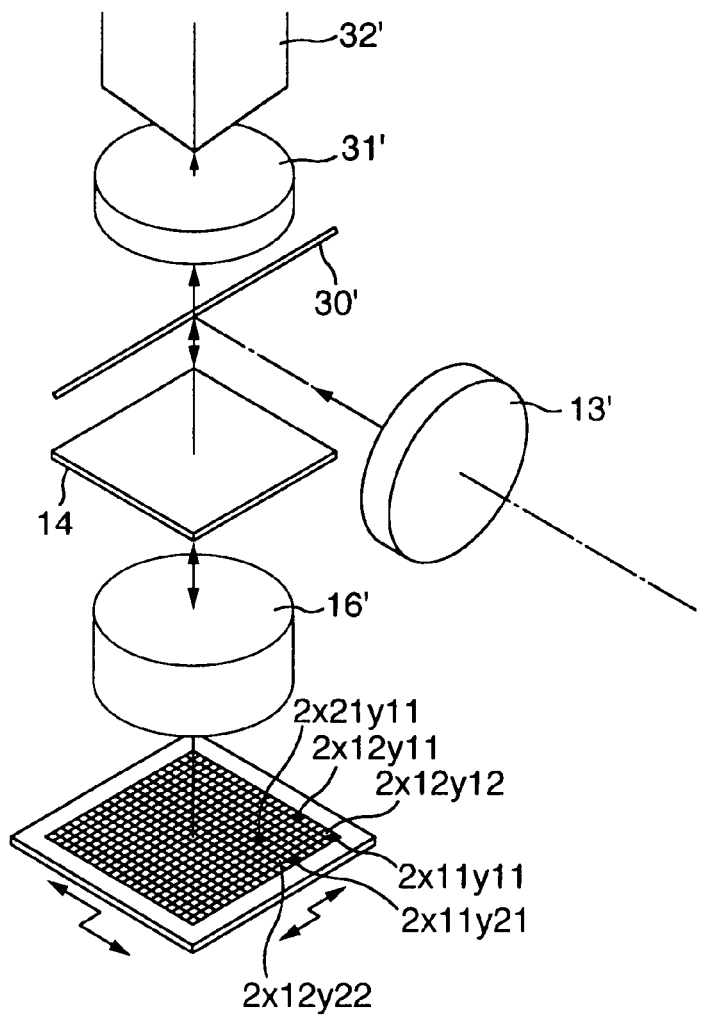
FIG. 13 is a diagram for illustrating another embodiment in the present invention.

FIG. 13 is a diagram for illustrating another embodiment of the DNA inspecting apparatus in the present invention. The same reference numeral as that in FIG. 1 denotes the same component. In the present embodiment, unlike the embodiment in FIG. 1, the detection in a 2-dimensional manner is executed as well simultaneously. Namely, the excitation illumination light is caused to pass through an illuminating lens 13' capable of simultaneously illuminating a 2-dimensionally-broad range. Moreover, the excitation illumination light is reflected by a wavelength selection beam splitter 30', then illuminating a 2-dimensional microlens array 14'. The 2-dimensional microlens array 14' has the same functions as those in the case where the 1-dimensional microlens array has been already explained using FIGS. 1 to 4, and what differs therefrom is the 2-dimensional array arrangement alone. Consequently, as illustrated in FIG. 14, 2-dimensional microscopic spots 1410' are formed at focal point positions of microlenses 141'.

In the case of the present embodiment, pinhole apertures are bored with the positions of 1410' as their center. In this way, the DNA chip is irradiated with only the lights that have passed through the pinhole apertures. A ratio between a diameter d of the microscopic multi spots and an arrangement pitch p of the spots is equal to an integer that is larger than 2 and that, preferably, is larger than 5. As illustrated in FIG. 13, a high-resolution lens 16' causes the DNA chip to be simultaneously irradiated and excited with the 2-dimensional multi-spot lights having passed through the pinhole apertures. The pixels undergoing the excitation irradiation, i.e., $2x11y11$, $2x12y11$, $2x11y21$, $2x21y11$, . . . , have an equal pitch spacing with 4 pixels skipped.

Fluorescent lights generated from the above-described pixels that have simultaneously undergone the excitation irradiation pass through the above-described high-resolution lens 16', then passing through the respective pinholes 1410' on the lower surface of the microlens array. The fluorescent lights having passed through the pinholes pass through the respective microlenses, thereby being enlarged up to a size of the upper surfaces (convex surfaces) of the microlenses. The fluorescent light intensities on the upper surfaces of the microlenses are image-formed onto a high-sensitivity image storage type 2-dimensional sensor 32' through the wavelength selection beam splitter 30' and an image-forming lens 31'. Although the interference filter is not illustrated in the present drawing, the interference filter, or the color filter that permits a wavelength longer than the fluorescent lights to pass through is provided between the wavelength separating beam splitter 30' and the 2-dimensional sensor 32'.

Figure 14:
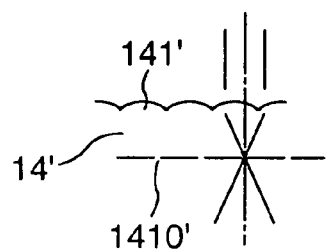
FIG. 14 is a diagram for illustrating a 2-dimensional multi-spot generating microlens array used in the embodiment in FIG. 13.

In the 1-dimensional and 2-dimensional microlens arrays illustrated in FIG. 4 and FIG. 14, respectively, a light incoming into an intermediate area between the adjacent microlenses in the respective microlenses is in a danger of becoming a scattered light and then a noise light. Thus, by performing a masking (not illustrated) by which the intermediate area is covered with a light-shielding portion composed of a material such as chromium oxide, it becomes possible to eliminate such a noise.

Figure 15:
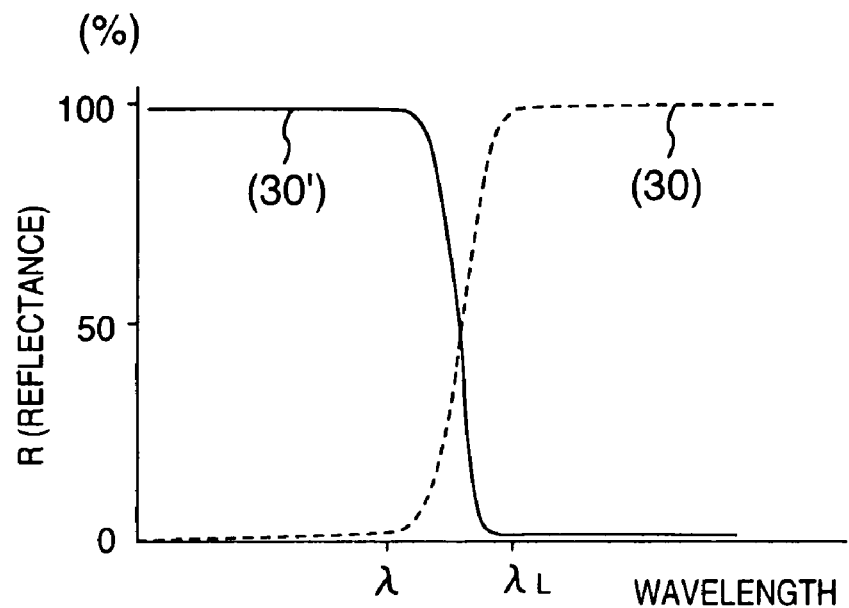
FIG. 15 is a diagram for indicating a characteristic of the wavelength separating beam splitter in the embodiments in the present invention.
Figure 16:
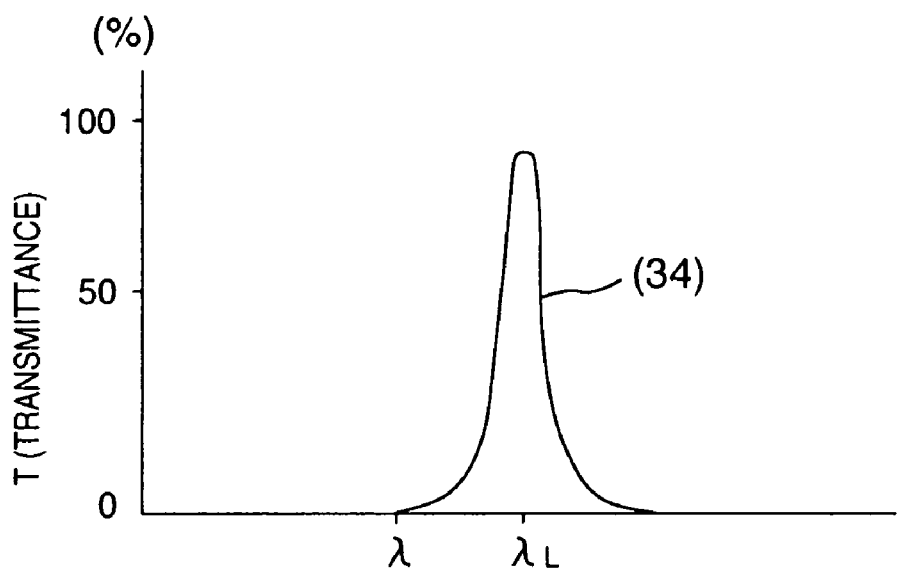
FIG. 16 is a diagram for indicating a characteristic of an interference filter in the embodiments in the present invention.

FIG. 15 and FIG. 16 illustrate a spectroscopic reflection characteristic and a spectroscopic transmittance characteristic respectively of the wavelength separating beam splitters 30, 30' and the interference filter 34, which have been used in the above-described embodiments and in FIGS. 1, 5, 7, and 13. The use of both of the apparatuses makes it possible to decrease the influences of the excitation lights, thereby allowing the precise detection to be executed. In the drawing, $\lambda$ denotes a wavelength of the excitation lights. The excitation wavelength bandwidth is narrow because the laser light is usually used in order to increase a per-unit area intensity of the spot irradiation. $\lambda_L$ denotes a central wavelength of the fluorescent lights to be detected.

As the fluorescent material added to the DNA fragment to be hybridized, several types of fluorescent substances are employed. For example, when employing often employed Cy5 (Cyanine5), an absorption peak wavelength of the fluorescent material is equal to 649 nm and a peak wavelength of the fluorescent lights is equal to 670 nm. Also, on an even shorter wavelength side, when employing Cy3 (Cyanine3), the absorption peak wavelength of the fluorescent material is equal to 550 nm and the peak wavelength of the fluorescent lights is equal to 570 nm. Since the spectroscopic absorption characteristic of the absorbing material has a bandwidth, it is not always required to cause the wavelength of the excitation laser light to coincide with the absorption peak wavelength. Accordingly, there is used a laser light the wavelength of which is close to the absorption peak wavelength.

In the case of Cy5, there is used a red He—Ne laser light at the wavelength of 633 nm or a semiconductor laser light at the wavelength of 635 nm. In the case of Cy3, there is used a green He—Ne laser light at the wavelength of 544 nm or the like. In the interference filter and the wavelength separating beam splitter for extracting only the fluorescent lights, as the central wavelength, a wavelength is selected which is close to the fluorescent light peak wavelength and at which it is easy to separate the excitation lights.

In the above-described fluorescent light detection, it becomes of the utmost importance to completely light-shield the excitation lights especially when the fluorescent lights are weak.

Figure 17:
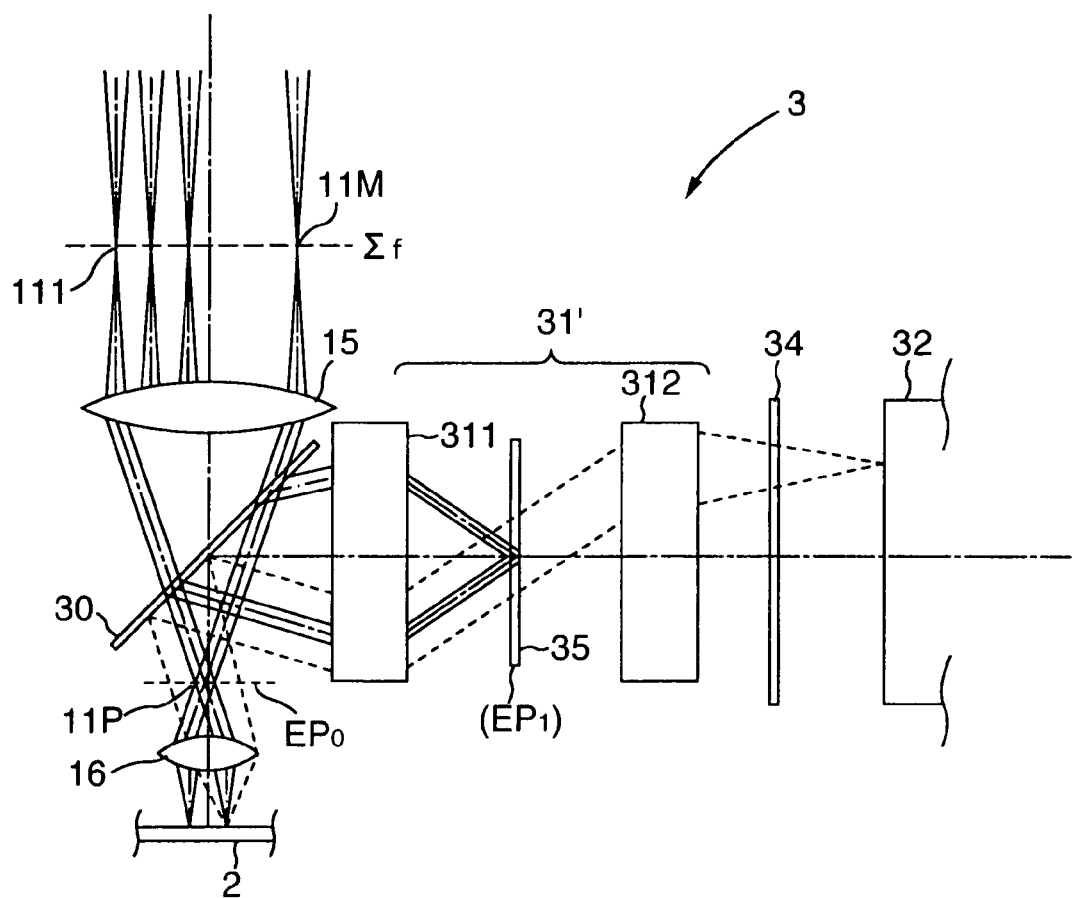
FIG. 17 is an embodiment-illustrating diagram in the present invention, where excitation lights are light-shielded using a space filter.

FIG. 17 is an embodiment-illustrating diagram in the present invention, where it is intended to execute the above-described light-shielding of the excitation light more completely. Namely, the light-shielding based on the present embodiment is executed in the following cases: The use of the interference filter or the wavelength separating beam splitter alone is insufficient for the light-shielding, or it is desirable to increase the band half-value width of the interference filter in order to increase the fluorescent light detection intensities. In FIG. 17, the same reference numeral as that in FIG. 1 have the same component or the same function.

A multi-spot array $11_1, \ldots, 11M$ formed on a plane $\Sigma_f$ by the microlens array or the hologram is image-formed onto the DNA chip as excitation lights through the operation of the lens 15 and the objective lens 16. At this time, the respective multi-spot lights pass through a center of an incident pupil $EP_0$ of the objective lens with a spread the radius of which is substantially $RNA_o$. Setting a numerical aperture and the focal length of the objective lens to be NA and f, respectively, a spot diameter Ds of the excitation lights on the DNA chip is given by the following equation:

$$Ds = 2k_1 f \lambda / RNA_o'$$

(where $k_1 = 0.6$)
Representing, by p, a pixel resolution (the pixel pitch) for the DNA chip detection, this value is substantially equal to Ds. Assuming that p is equal to 2 μm and the excitation light wavelength λ is equal to 633 nm, a value $RNA_o'/f$ becomes equal to 0.19. The value $RNA_o'/f$ is a NA of an illumination for illuminating the spot of 2 μm (i.e., a minimum NA of the objective lens needed in order to image-form the 2 μm spot). Representing this value by NA', the NA' is given as follows:

$$NA' = \sin(\tan^{-1}(RNA_o'/f)) \approx RNA_o'/f = 0.19$$

In order to detect the weak fluorescent lights, the NA of the objective lens 16 falls in the range of 0.7 to 0.9.

Next, the respective excitation spot lights, which have passed through the incident pupil of the objective lens with the above-described spot diameter, irradiate the DNA chip with the excitation spot lights of about 2 μm through the operation of the objective lens. Since the objective lens is both-telecentric in nature, about 4 to 8% of the excitation lights out of the excitation lights incoming into the DNA chip in perpendicular thereto are regularly reflected by the chip surface, then returning back to the objective lens. The wavelength separating beam splitter permits most of the regularly reflected excitation lights to pass through, but the beam splitter reflects the regularly reflected excitation lights by just a slight amount. Then, the slight amount of reflected excitation lights travel toward the fluorescent light detecting system 3.

Figure 18:
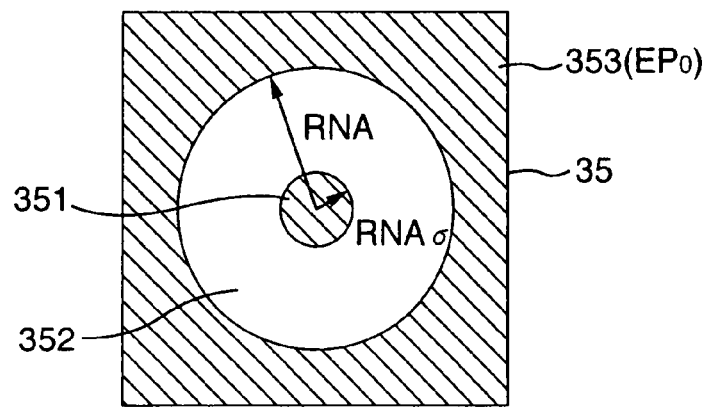
FIG. 18 is a diagram for illustrating the space filter in FIG. 17.

The fluorescent light detecting system 3 includes the interference filter 34, thereby light-shielding the excitation lights. Nevertheless, the complete light-shielding is a difficult task. Namely, trying to widen the bandwidth of the interference filter so as to detect the fluorescent lights as much as possible results in just a slight amount of leakage of the excitation lights. Thus, a lens system 31' for image-forming and detecting the fluorescent spot lights onto a fluorescent light detection plane (or, a plane conjugated therewith) is configured with lens systems 311, 312 as illustrated in the drawing. This configuration is designed so as to image-form the objective lens pupil at a position existing between 311 and 312. A space filter 35 is located at this position conjugated with the pupil. The space filter 35 has a configuration as illustrated in FIG. 18.

The light-forming magnification of the objective lens pupil surface toward the space filter 35 by the lens system 311 is assumed to be 1 time. The space filter has a circle-shaped light-shielding portion 351 of a radius RNA, in the central portion of an aperture, the aperture having a radius RNA that is equal to a radius of the objective lens pupil from the optical axis center of a light-shielding portion 353. The multi-spot excitation lights, which had been regularly reflected by the DNA chip, turns out to have the beam radius of $RNA_o$, on the space filter. Consequently, if $RNA_o > RNA_o'$ holds, the regularly reflected excitation lights are light-shielded by the light-shielding portion 351.

Meanwhile, the fluorescent lights excited and generated by the multi-spot excitation lights are launched into the objective lens with almost no directivity, then incoming into the space filter. The light-shielding portion 351 light-shields the fluorescent lights as well, but a ratio of the light-shielded fluorescent lights toward the space filter incoming fluorescent lights becomes equal to $(NA'/NA)^2$. Substituting the above-described value, this value is found to be 7 (when NA=0.7) to 4 (when NA=0.9)%, which is a loss of a negligible order.

In this way, it is possible to reduce the unnecessary excitation lights tremendously without lowering the light amount of the fluorescent lights to be detected. The fluorescent light detection lights having passed through the space filter pass through the lens 34 and the interference filter 34, then image-forming the spot images on the DNA chip onto the detection plane, i.e., the optical fiber light-emitting ends, so as to be subjected to the fluorescent light detection.

Figure 19:
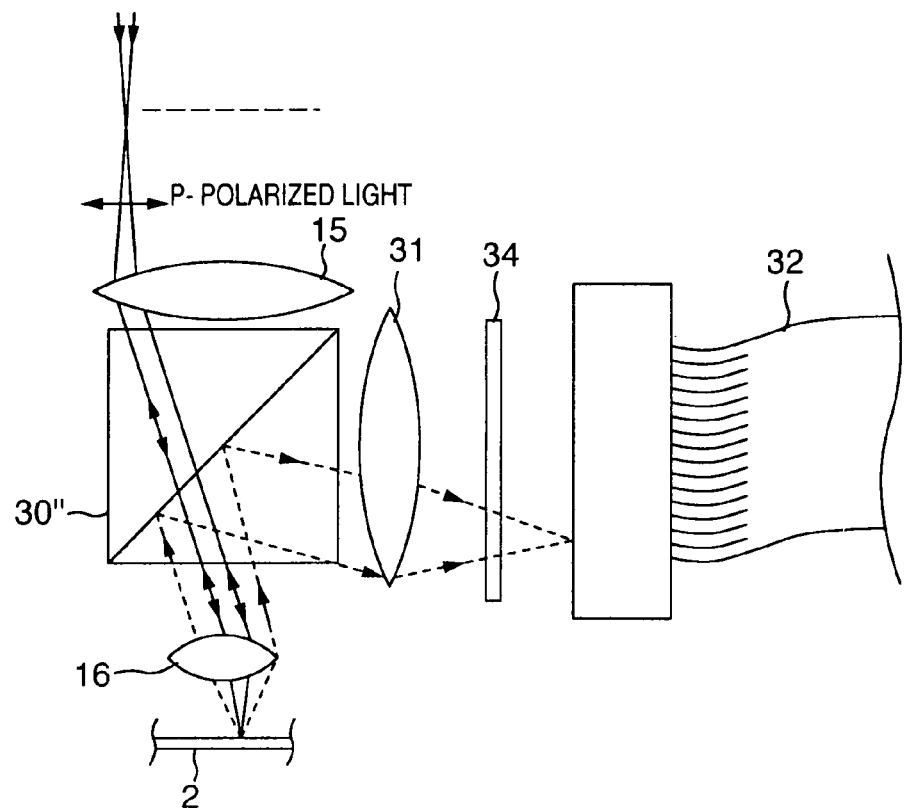
FIG. 19 is another embodiment-illustrating diagram in the present invention, which is a diagram for illustrating an excitation light light-shielding method utilizing the polarization.

FIG. 19 is an embodiment-illustrating diagram in the present invention, which indicates a method of preventing the excitation lights from being guided into a fluorescent light detecting optical path. The same reference numeral as that in FIG. 1 denotes the same component. In the present embodiment, a polarization beam splitter 30" is employed as a beam splitter for branching off the fluorescent light detecting optical path from an excitation light optical path. Namely, a split surface of the polarization beam splitter is irradiated with the excitation lights that are P-polarized toward the split surface. Then, since the excitation lights having been reflected on the DNA chip surface and having returned back still remain P-polarized, the excitation lights pass through the polarization beam splitter and never enter the fluorescent light detecting optical path. On the other hand, since the polarization state of the generated fluorescent lights differs from that of the excitation lights, the S-polarized fluorescent lights are reflected by the polarization beam splitter 30", then being guided into the fluorescent light detecting optical path. In this way, this method makes it possible to prevent the excitation lights from being guided into the fluorescent light detecting optical path.

Figure 20:
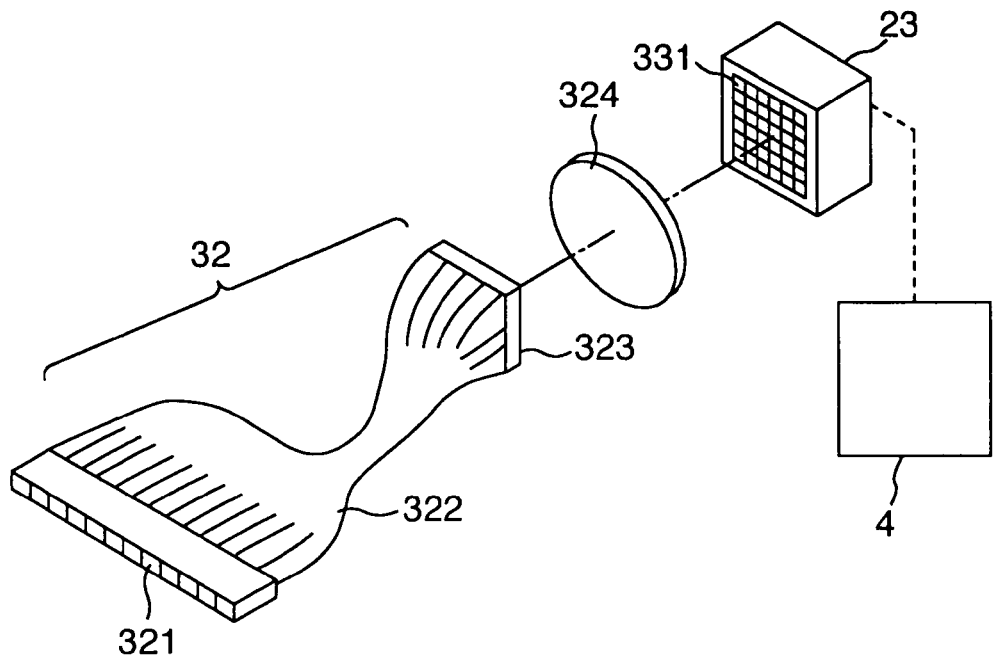
FIG. 20 is an embodiment-illustrating diagram in the present invention, where the 1-dimensional spot array is detected using a 2-dimensional multi-channel photomultiplier tube.
Figure 21:
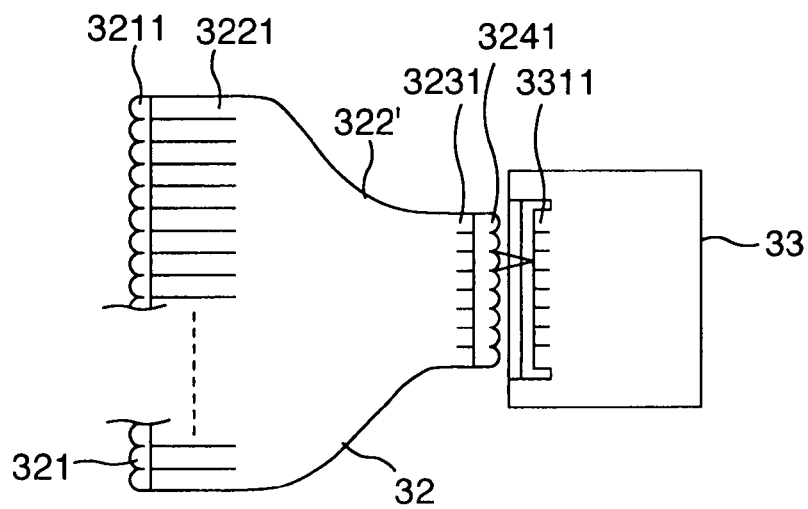
FIG. 21 is a diagram for illustrating light-receiving and light-emitting ends of optical fibers and taking-in of spot images in the embodiment in FIG. 20.

FIG. 20 is an embodiment-illustrating diagram in the present invention, where the fluorescent light detection is executed using the optical fibers and the multi-channel photomultiplier tube. Namely, FIG. 20 illustrates the concrete content of the detection of the fluorescent light multi-spot images in the embodiments illustrated in FIGS. 1, 5, 7, 17, and 19. As illustrated in FIG. 21, the light-receiving end of the fiber system 32 for the fluorescent light multi-spot images the multi-spot number of which is M or more is the multi-lens array 321 including 1-dimensionally arranged M lenses.

As having been explained in FIG. 7, using the respective microlenses, the fluorescent light multi-spot images are launched into the cores through which a light passes in the fibers. If, as illustrated in FIG. 20 the multi-channel photomultiplier tube 33 includes 2-dimensionally arranged light-receiving apertures, the light-emitting ends of the fibers are also configured to be 2-dimensionally arranged. In the case of the embodiment in FIG. 20, the fluorescent lights emitted from the respective light-emitting ends are image-formed by the image-forming lens 324 in such a manner that the fiber light-emitting ends 323 correspond to the respective light-receiving apertures 331 of the photomultiplier tube 33.

In the case of the embodiment in FIG. 21, a 2-dimensional lens array 3241 is provided at the light-emitting ends of the fibers in the corresponding manner. The fluorescent lights emitted from the respective fibers pass through the respective lenses, thereby being directly converged onto 2-dimensional light-receiving apertures (photoelectric plane) 3311 of the multi-channel photomultiplier tube. In the embodiments illustrated in FIGS. 20, 21, the 2-dimensional multi-channel photomultiplier tube is employed. When using the 1-dimensional multi-channel photomultiplier tube as well, configuring the light-emitting ends to be 1-dimensionally arranged also allows the detection to be executed by the same method.

Figure 22:
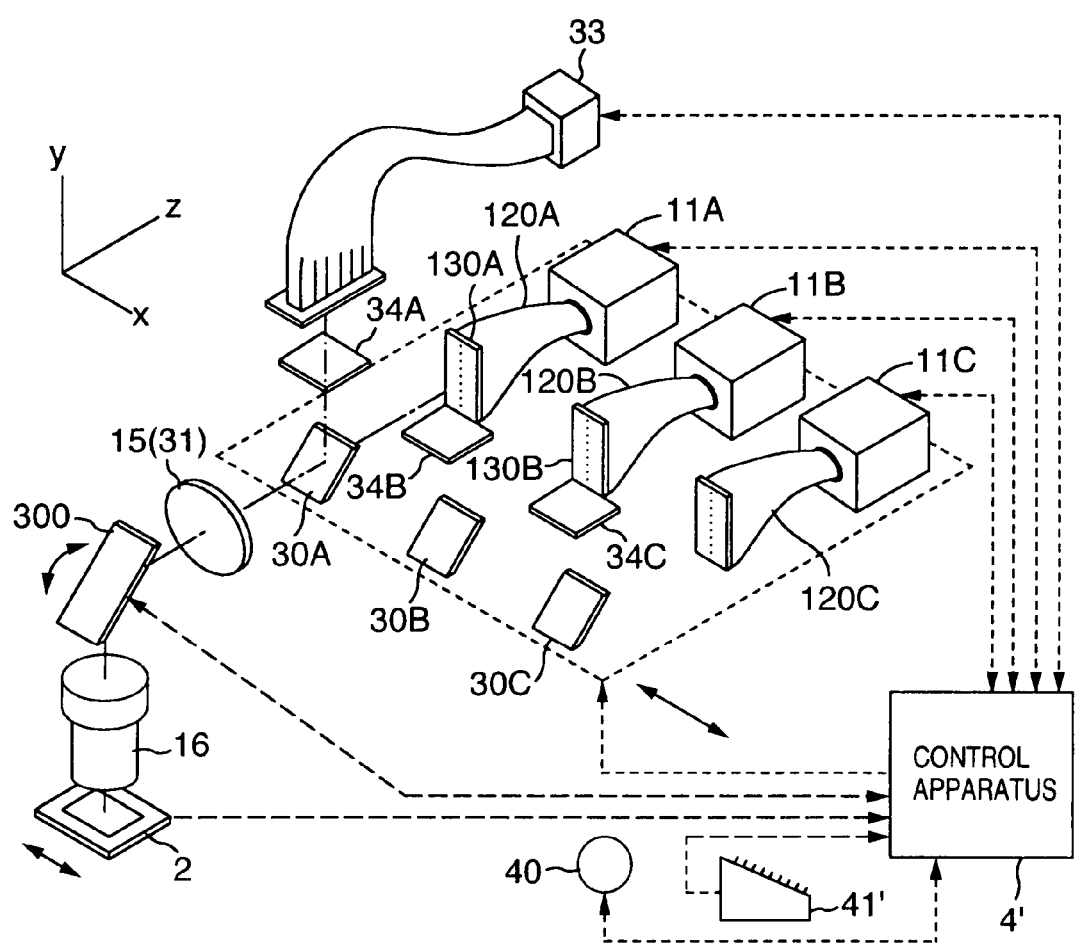
FIG. 22 is an embodiment-illustrating diagram in the present invention, where the detection is executed using excitation lights having a plurality of different wavelengths.

FIG. 22 is an embodiment-illustrating diagram in the present invention. In the present embodiment, as the excitation lights, there are used excitation lights having a plurality of different wavelengths. Light-source systems 11A, 11B, and 11C form lights emitted from excitation light light-sources with different wavelengths $\lambda_A$, $\lambda_B$, and $\lambda_C$, then causing the lights to be launched into fiber bundles. In the light-source systems, multi-lens arrays are arranged at the light-emitting ends, and pinhole arrays are provided at the positions at which the lights after being emitted are substantially converged, and the excitation lights having been emitted from the pinhole arrays are configured so that the excitation lights pass through wavelength separating beam splitters 30A, 30B, and 30 C. As illustrated in FIG. 22, when the system 11A is selected as the excitation light light-source system for the fluorescent light detection, the excitation light with $\lambda_A$ passes through the lens 15, and is reflected by a deflection mirror 300, then passing through the objective lens 16 so as to perform multi-spot excitation irradiation toward the DNA chip 2. Moreover, fluorescent lights generated from the respective multi spots pass through the objective lens 16, the deflection mirror 300, and the lens 15 (31). Then, the fluorescent lights are reflected by the wavelength separating beam splitter 30A, eventually passing through an interference filter 34A so as to be detected by the method explained in FIGS. 20, 21 using the multi-channel photomultiplier tube.

When the fluorescent lights to be detected are of different types, the entire light-source system 50 (i.e., 11A, B, C; 120A, B, C; 130A, B, C; 30A, B, C; 34A, B, C) is displaced in solid-line arrow directions in accordance with a control apparatus 4' by a driving mechanism not illustrated. Then, either of the different wavelengths $\lambda_B$ and $\lambda_C$ is selected so as to execute the fluorescent light detection using this selected wavelength. When the plurality of types of fluorescent lights are to be used for one DNA chip, the light-source systems are displaced in sequence, thereby executing the detection using the different excitation lights one after another.

Figure 26:
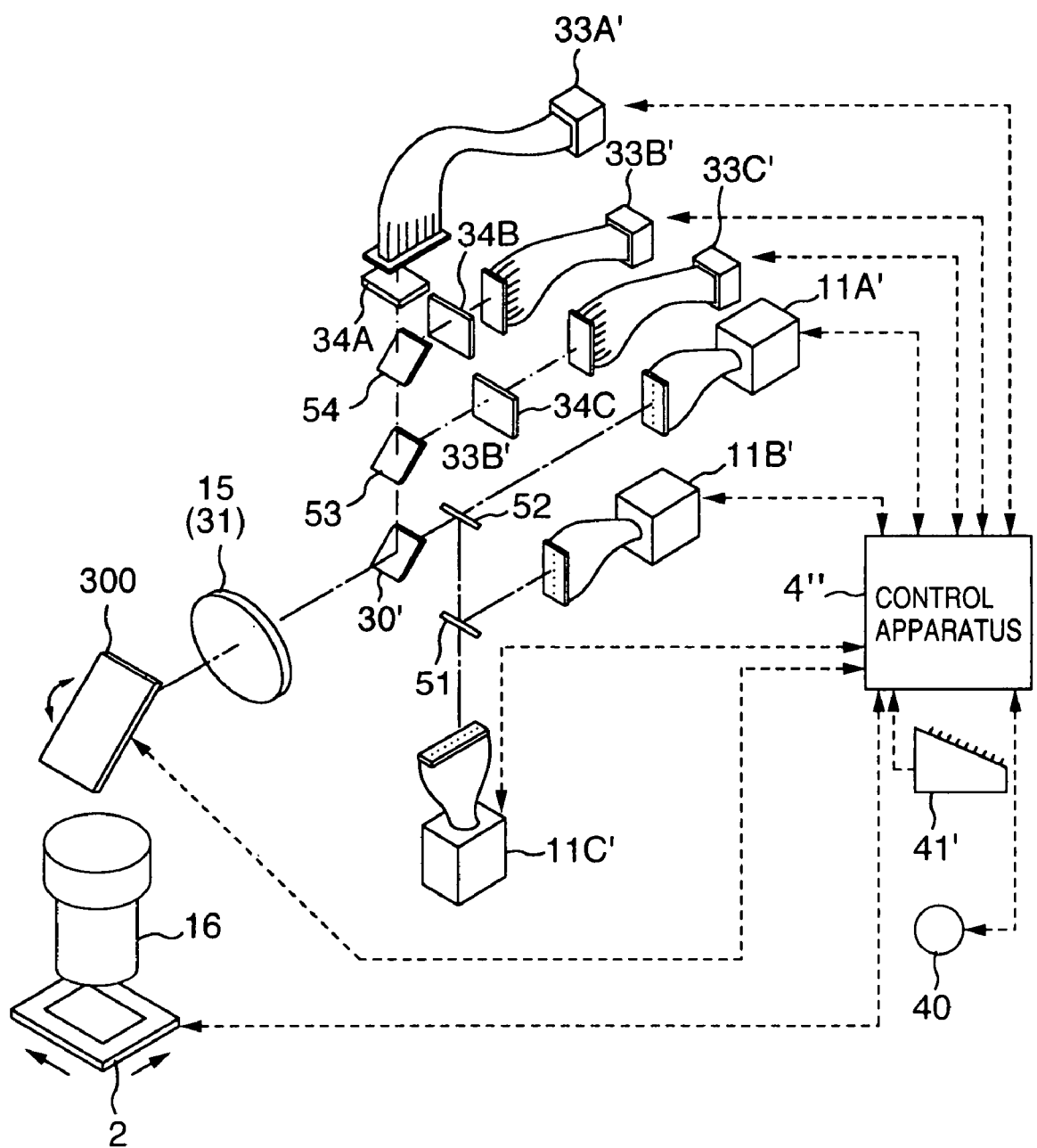
FIG. 26 is an embodiment-illustrating diagram in the present invention, where using excitation lights having a plurality of different wavelengths, the simultaneous detection is executed.

FIG. 26 is another embodiment-illustrating diagram, where the above-described plurality of types of fluorescent lights are used. Unlike the case in FIG. 22, irradiations with the plurality of types of excitation lights are performed simultaneously, thereby trying to shorten the detecting time. In FIG. 26, excitation lights, which are emitted from light-source systems 11A', 11B', and 11C' with a plurality of different wavelengths $\lambda_A'$, $\lambda_B'$, and $\lambda_C'$ corresponding to, for example, 3 colors of red, green, and blue, are synthesized effectively into one optical path by wavelength selection synthesizing mirrors 51, 52. Namely, the wavelength selection synthesizing mirror 51 permits blue to pass through and causes green to be reflected. Also, the wavelength selection synthesizing mirror 52 permits red to pass through and causes green and blue to be reflected.

The synthesized 3 colors pass through a beam splitter 30' and, after passing through the lens 15, the deflection mirror 300, and the objective lens 16, perform 3-color simultaneous spot excitation illuminations with the 3 colors onto the DNA chip. The respective fluorescent materials are excited at each wavelength and emit lights with the respective fluorescent colors. The fluorescent lights emitted have wavelengths that are slightly longer than those of the excitation lights. This condition makes it possible to separate, using wavelength separating beam splitters 53, 54, the wavelengths of the 3-wavelength fluorescent lights excited by the 3-wavelength excitation lights. Namely, the wavelength separating beam splitter 53 causes the blue fluorescent light to be reflected and permits the green and the red to pass through. Also, the wavelength separating beam splitter 54 causes the green to be reflected and permits the red to pass through.

In optical paths resulting from the separation into the respective 3 colors in this way, there are located interference filters 34C, 34B and the filter 34A that each permit the respective fluorescent lights alone to pass through with a high-purity. Then, the microscopic spot images of the respective fluorescent lights are detected simultaneously by the above-described method using multi-channel photomultiplier tubes 33C', 33B', and 33A' through fibers.

In the embodiments in FIGS. 22, 26, the deflection mirror 300 performs the array direction scanning of the excitation multi-spot lights. As the deflection mirror, there is employed a mirror of the piezo driving system or of the galvanometer mirror type. In this case, unlike the embodiment explained in FIG. 1, the multi spots are subjected not to the step displacement but to a continuous (linear) scanning. The multi spots on the DNA chip are scanned, but one and the same (identical) deflection mirror is used in the detecting optical path as well. As a result, unmoved multi spots are image-formed at the ends of the fluorescent light detecting fibers. On account of this, it turns out that pixel addresses are determined based on the deflection angle of the deflection mirror.

Based on the relationship between the pixel addresses and the deflection angle, a plurality of fluorescent light detection signals obtained from the multi-channel photomultiplier tubes in a parallel manner are organized and stored by the control apparatuses 4' (FIG. 22) or 4" (FIG. 26). Such data processing, of course, requires that the measuring and detecting conditions be inputted in advance. These pieces of input information are inputted from a terminal 41' or from a high-order computer 40 then, as necessary, data on the measured and inspected result is transferred to the computer.

In the embodiment in FIG. 26, the explanation has been given concerning the case where the irradiations with the plurality of excitation lights having the different wavelengths are performed simultaneously. By the way, in the case where there exist an overlap between the wavelength bands of the plurality of excitation lights and those of the fluorescent lights at which the respective excitation lights aim, a shutter situated near the light-sources and not illustrated is used toward the overlapped excitation light or the fluorescent light detection is executed with the time shifted by an ON-OFF of the light-sources themselves.

Figure 23:
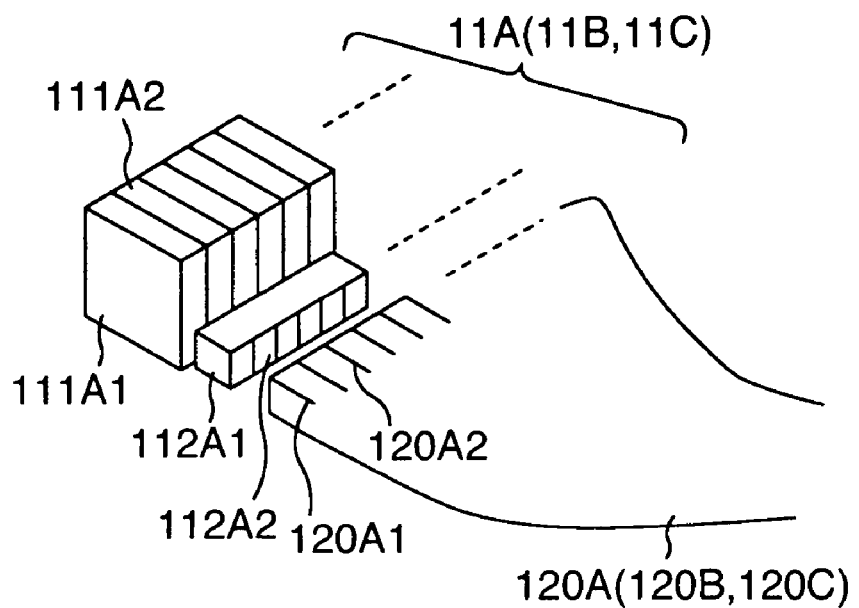
FIG. 23 is an embodiment-illustrating diagram in the present invention, where a plurality of semiconductor lasers are used as the excitation lights.

FIG. 23 is an embodiment-illustrating diagram in the present invention, where a plurality of semiconductor lasers 111A2, 111A2, . . . having substantially the same wavelength are employed as the excitation light light-source. The semiconductor laser is of a small volume, producing a comparatively high-output, and is inexpensive. As a consequence, as illustrated in the drawing, configuring a multi-spot light-source using a large number of semiconductor lasers makes it possible to irradiate the DNA chip with intense multi-spot excitation lights, thereby allowing the high-speed detection to be implemented. The lights emitted from the respective semiconductor lasers are taken into light-receiving ends of fibers 120A1, 120A2, . . . by lenses 112A1, 112A2, . . . .

Figure 24:
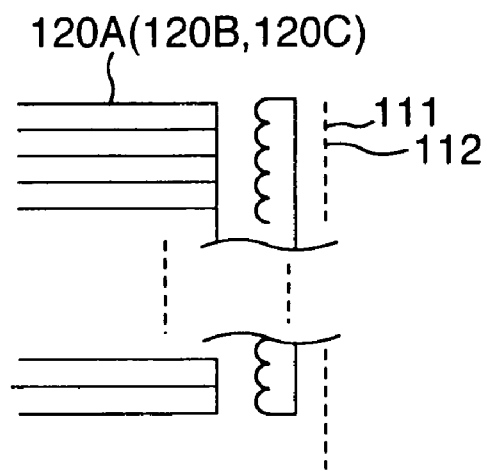
FIG. 24 is an embodiment-illustrating diagram in the present invention, where multi-spot lights are obtained from light-emitting ends of optical fibers.

The laser lights emitted from the light-emitting ends, as illustrated in FIG. 24, are converged onto a pinhole arrangement 111, 112, . . . through a microlens array. Then, the transmittance lights having passed through the pinhole arrangement are used as the multi-spot excitation lights.

If the semiconductor lasers are not usable as the excitation lights, there are used high-output solid-state lasers excited with the semiconductor lasers, and high-output gaseous lasers. In such laser light-sources, by using an emitted beam in such a manner as to be split by a method illustrated in FIG. 25, it becomes possible to form multi-spot excitation lights having substantially the same intensity and substantially the same beam configuration.

Namely, the beam emitted from a laser light-source 111A' is split using multi-splitting beam splitters 1110A', 1120A', . . . . It is assumed that the number of the splitting is equal to k and reflectances of beam-split lights from the 1st stage of the splitting through the 2nd stage, the 3rd stage, . . . to the k-th stage are equal to $r_1, r_2, \ldots r_j, \ldots r_k$. Considering that $r_k$ is equal to 1 and since the respective beam-split lights are equal in their intensities, with reference to an arbitrary j ($1 \leq j \leq k$), $$r_j = 1/(k-j+1)$$

should be satisfied in order to form the above-described multi-spot excitation lights. Namely, at 111A', since k is equal to 4, i.e., 4-splitting, $r_1, r_2, r_3,$ and $r_4$ become equal to ¼, ⅓, ½, and 1, respectively. Similarly, since 3-splitting is performed at 1120A', $r_1, r_2,$ and $r_3$ become equal to ⅓, ½, and 1, respectively. In this way, the laser lights having the same intensity and the same beam configuration are launched into a lens array 112A1', then being launched into cores of the fibers.

Figure 25:
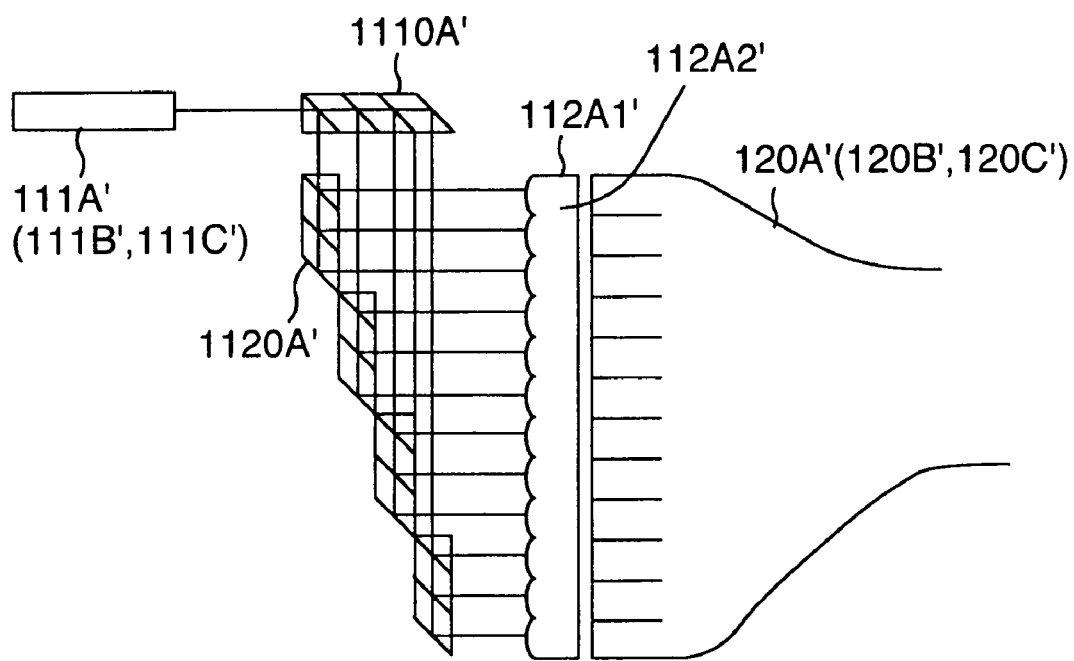
FIG. 25 is an embodiment-illustrating diagram in the present invention, where the multi-spot lights are obtained from one laser beam.

In the embodiment in FIG. 23, the plurality of semiconductor lasers are employed as the excitation light light-source for the generation of the multi-beam spots. In the case where the available laser light power is inadequate, however, it becomes required to form the multi-spot excitation lights with the use of a plurality of gaseous lasers other than the semiconductor lasers or a plurality of lasers based on the 2nd harmonics. In such a case, the systems illustrated in FIG. 25 are used in plural number and the fiber light-emitting ends picked up from the plurality of systems are arranged on a 1-dimensional line or a 2-dimensional plane. This makes it possible to obtain the multi-spot excitation lights with a high-excitation intensity.

In the above-described case where the plurality of excitation lights are used, depending on the excitation wavelength, there arises a necessity of using various types of different lasers, such as the semiconductor laser, the gaseous laser, and the solid-state laser using the 2nd harmonics excited with the semiconductor. In such a case, it is all right to form the multi-spot excitation lights in accordance with the above-described method illustrated in FIG. 23 or FIG. 25.

Figure 27:
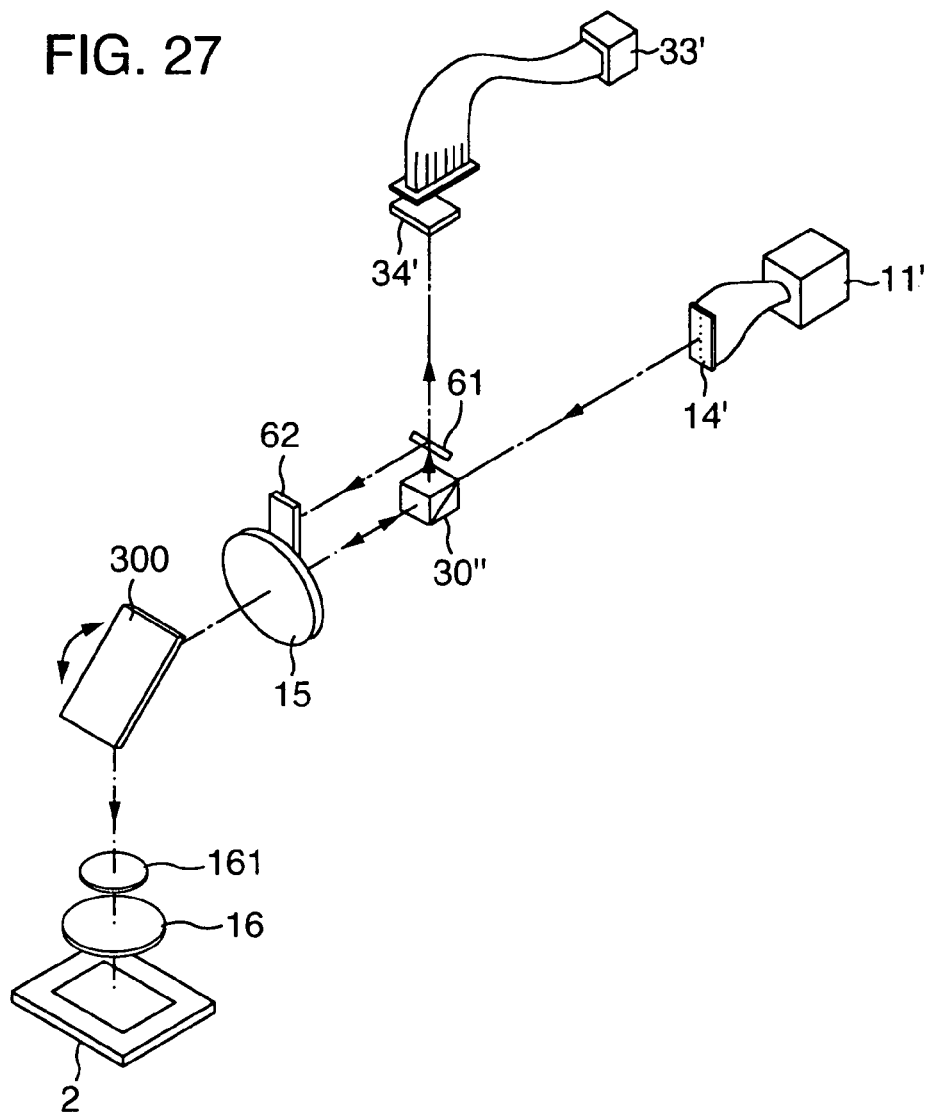
FIG. 27 is an embodiment-illustrating diagram in the present invention, where irradiation with the multi-spot lights is performed in an oblique direction and regularly reflected excitation lights are light-shielded on a pupil.
Figure 28:
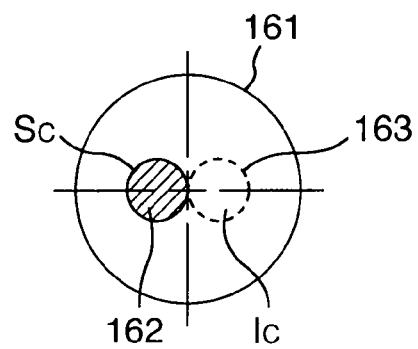
FIG. 28 is a diagram for illustrating a light-shielding portion on the pupil in FIG. 27.

FIGS. 27, 28 are embodiment-illustrating diagrams in the present invention. In the drawings, by eliminating the influences of the fluorescent lights and the scattered lights generated by the excitation multi-spot lights from a foreign substance mixed in the DNA chip, or the influence of a scattered light from a foreign substance in the fluorescent light detecting optical system, it is made possible to implement the high-accuracy fluorescent light detection. A reference numeral 11' denotes an excitation light-source, which causes a light to pass through a pinhole aperture array 14' through a fiber so as to create the excitation multi-spot lights. The multi-spot lights are image-formed onto the DNA chip through the operation of the lens 15 and the objective lens 16. A space filter 161 is located at the position of an incident pupil of the objective lens.

Figure 29:
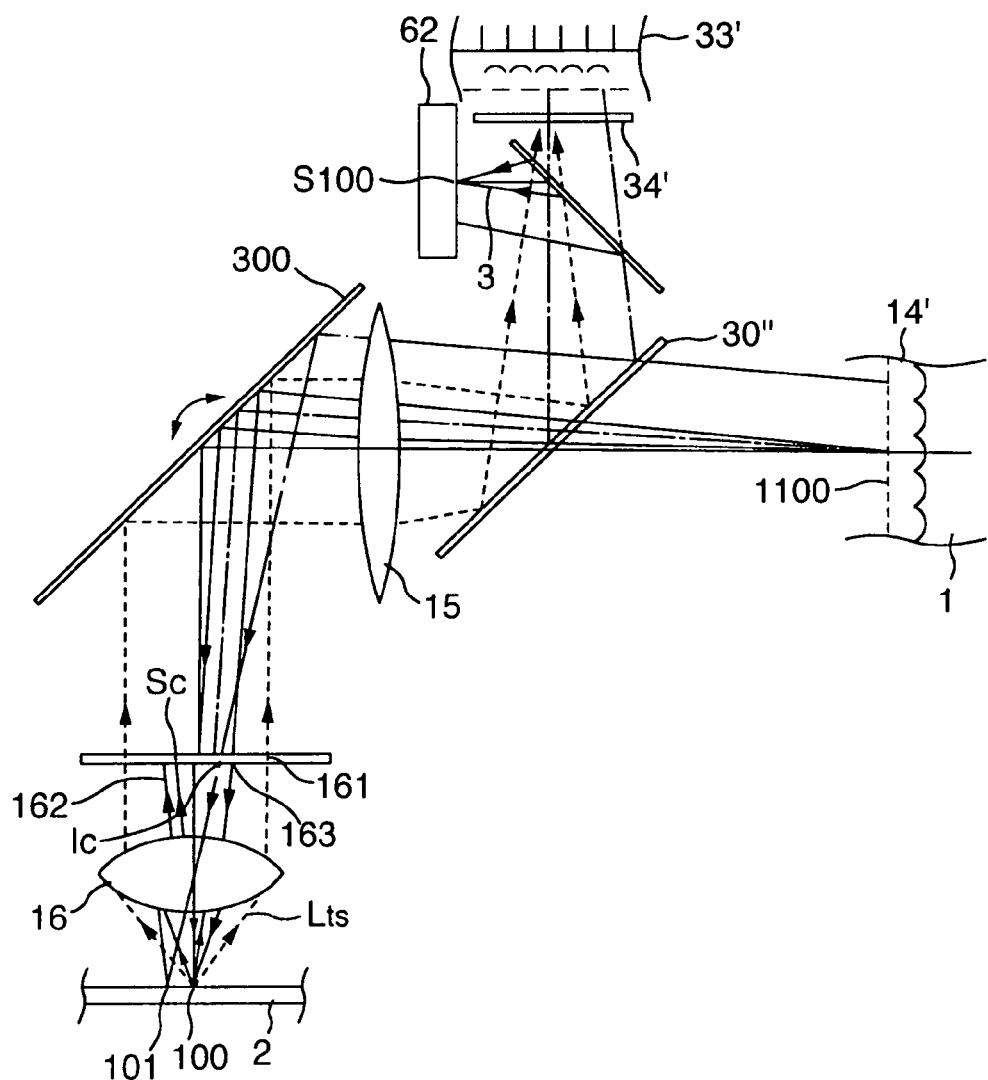
FIG. 29 is an embodiment-illustrating diagram in the present invention, which indicates a method of detecting scattered excitation lights so as to determine a foreign substance position and correcting a fluorescent light detection result.
Figure 30:
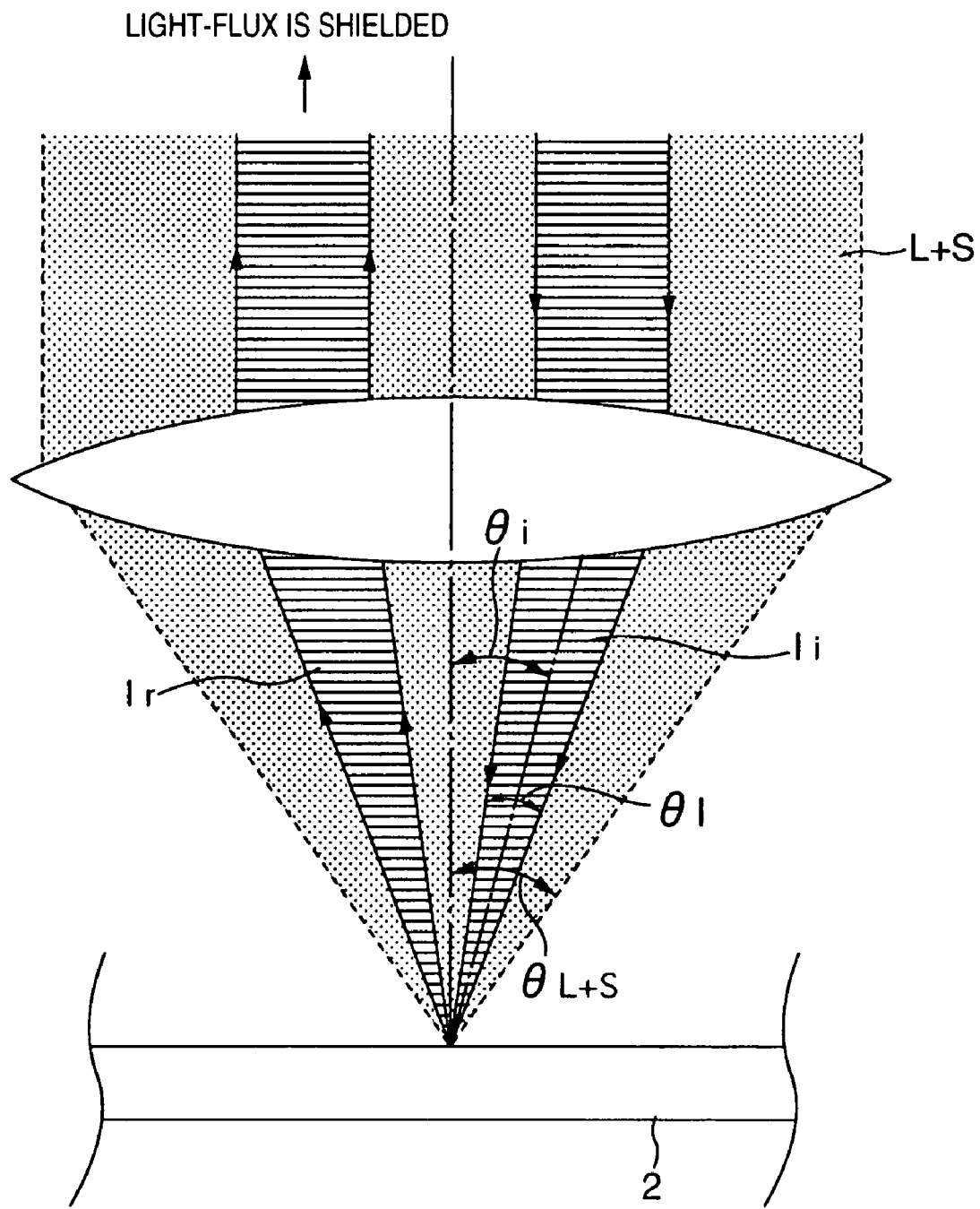
FIG. 30 is a diagram for illustrating the regularly reflected excitation lights and the scattered excitation lights between an objective lens and a DNA chip in FIG. 29.

The excitation multi-spot lights are set so that the multi-spot lights pass through a position 163 (refer to FIG. 28) shifted off from a center of the incident pupil. Namely, as illustrated in FIGS. 29, 30, the respective multi-spot lights pass through a portion shifted off from an optical axis of the objective lens, becoming a light-flux Ii represented by an oblique sloped line in FIG. 30. Then, the DNA chip 2 is irradiated with this light-flux in an oblique direction at an incident angle θi. As having been explained earlier in the relationship between the spot diameter and the NA', a convergence angle θI of this irradiation converging light is expressed by (NA') θI/2.

Also, the excitation lights reflected regularly by the DNA chip pass through the objective lens, then passing through a position (the position indicated by 162 in the drawing) that is symmetrical with 163 with the lens, optical axis as the symmetrical center on the pupil 161 (refer to FIG. 28).

Thus, as illustrated in FIG. 28, forming, in this position, a member 162 for light-shielding the regularly reflected excitation lights allows the regularly reflected excitation lights to be light-shielded by this member 162. In this way, the position off from the center of the pupil is set to be the optical path of a primary light-ray of the excitation lights. Moreover, with reference to the incident angle θi of this primary light-ray, a condition θi>θI/2 is made to be satisfied. This condition makes it possible to light-shield the regularly reflected excitation lights on the pupil without light-shielding the excitation lights on the pupil. It is needless to say that the present embodiment has the effect of eliminating the noise caused by the excitation lights, which has been explained in the embodiment in FIG. 17.

In the embodiment in FIG. 27, in addition to this effect, the influences of the foreign substance mixed on or in the DNA chip are eliminated in the following way: Namely, if there exists the foreign substance such as various kinds of proteins mixed at the time of forming the DNA sample, the irradiation of the foreign substance with the excitation lights causes the excitation lights to be scattered, because the dimension of such a foreign substance is small, i.e., several μm. Also, in the case of the above-described foreign substance of the organic substance type, intense fluorescent lights are emitted from the foreign substance, becoming the fluorescent lights that are more intense than the fluorescent material added to the DNA to be detected.

As illustrated in FIG. 30, the scattered excitation lights pass through a dotted-line surrounded area L+S determined by the NA (=sin $\theta_{L+S}$) of the objective lens. Then, after passing through the objective lens, the scattered excitation lights pass through a portion other than the light-shielding member 162 of the space filter, leaking into the fluorescent light detecting system. Only this leakage of the scattered excitation lights is extracted using a wavelength separating beam splitter 61, then executing the image detection. The wavelength separating beam splitter permits the fluorescent lights to pass through and causes the excitation lights to be reflected. Although, in FIG. 29, the wavelength separating beam splitter 61 is inserted in optical paths behind the wavelength separating beam splitter 30", it may be inserted in optical paths before the beam splitter 30". In this way, in much the same manner that the fluorescent light image is photographed by a detector 33' such as the multi-channel photomultiplier tube, an excitation light scattered image S100 ((refer to FIG. 29) of the excitation lights scattered by the foreign substance is detected as an image by a detector 62.

Figure 31A:
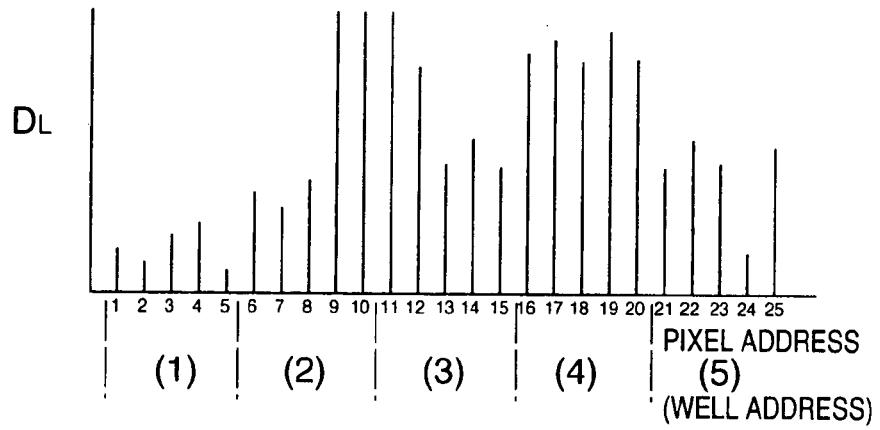
FIGS. 31A, 31B, 31C are diagrams for indicating a method of the correction by a detection signal of the foreign substance-scattered excitation lights.
Figure 31B:
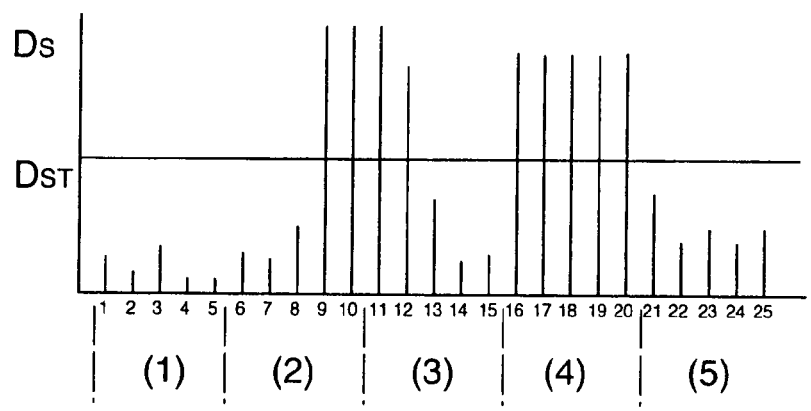

FIGS. 31A, 31B indicate, at a signal level on the per-pixel basis, a fluorescent light image signal $D_L$ and an excitation light image signal $D_S$ that have been detected in this way. Namely, numerals 1, 2, ..., 25 denote detected pixel addresses and numerals (1), (2), (3), (4), (5) denote addresses of cells to which the same DNA sequence is hybridized. Namely, for example, the pixels at the addresses 1, 2, 3, 4, 5 belong to the cell (1). Although, actually, the pixels in the cells are 2-dimensionally located and there exist, for example, 5×5 pixels, the pixels are 1-dimensionally located in order to make the drawings-accompanying explanation easy to understand. If the detection is exerted upon a pixel where the foreign substance exists, the scattered excitation light from the pixel exceeds a threshold value $D_{ST}$.

Figure 31C:
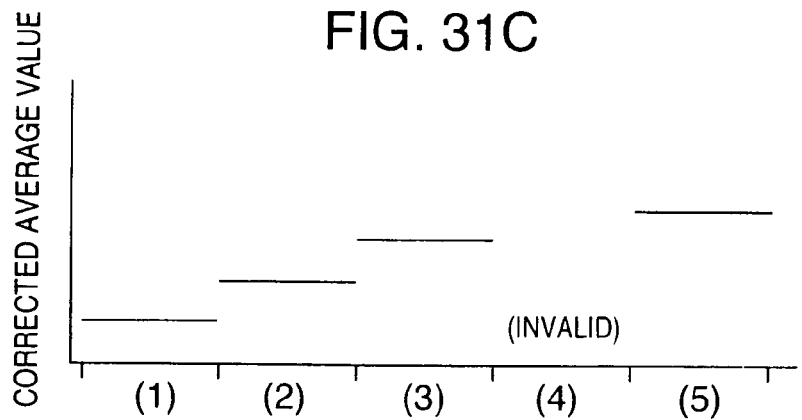

In FIG. 31B, at the pixel addresses 9, 10, 11, 12, and 16, 17, 18, 19, 20, the excitation light image signal $D_S$ exceeds the threshold value $D_{ST}$. Consequently, the information on the fluorescent light image signal $D_L$ existing at the corresponding addresses is strongly influenced by the foreign substance. Accordingly, an average value of the fluorescent lights in each cell is determined by discarding the information at these addresses. Namely, concerning the cell (2), the average value is determined not by using the information at the addresses 9, 10 but by using only the information at the remaining addresses 6, 7, 8. Similarly, concerning the cell (3), the average value is determined by using only the information at the addresses 13, 14, 15. In the cell (4), the scattering from the foreign substance occurs in all the pixels, and thus this cell is regarded as being invalid. The average intensity in each cell is determined in this way as is illustrated below in the graph in FIG. 31C. This allows the influences of the foreign substance to be reduced tremendously, thereby making it possible to execute the precise fluorescent light detection.

Incidentally, in the optical systems of the embodiments explained using FIGS. 27 to 30 where the influences of the foreign substance are eliminated, there are provided the optical systems where the excitation lights illuminate the DNA chip after passing through the objective lens. However, the configuration is also allowable where the irradiation with the excitation lights is performed from between the objective lens and the DNA chip in an oblique direction without passing through the objective lens. In this case, since the regularly reflected excitation lights are not launched into the objective lens, a space filter (which is equivalent to 161) becomes unnecessary.

Figure 32:
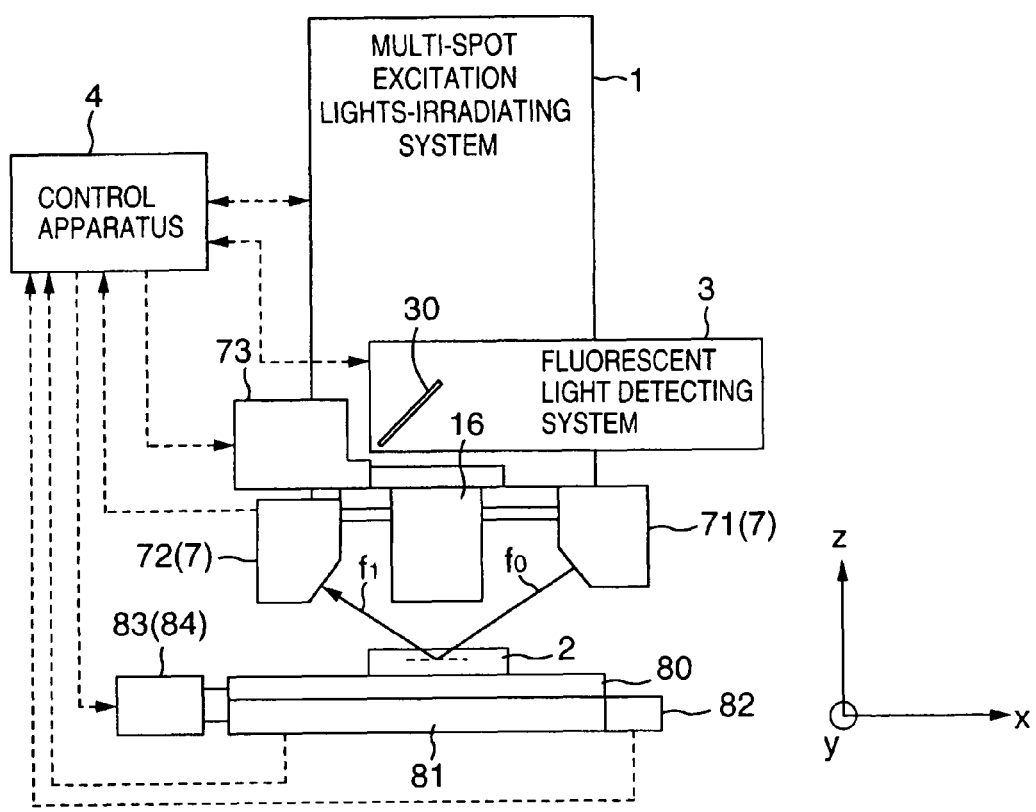
FIG. 32 is an embodiment-illustrating diagram in the present invention, which indicates focus detection and the control.

FIG. 32 is an embodiment-illustrating diagram in the present invention. The reference numerals denote the following components: 1 the multi-spot excitation lights-irradiating system the detailed embodiments of which have been explained already, 3 the fluorescent light detecting system for detecting the fluorescent lights generated by the multi-spot excitation lights, the details of which have been also explained already. The fluorescent material attached to the DNA hybridized onto the DNA chip 2 is irradiated with the microscopic multi-spot excitation lights of several μm through the use of the objective lens 16. In order to accomplish this, it is required to always maintain the distance between the objective lens and the fluorescent light plane at a fixed spacing within the focal depth so that the spot size is kept at a constant value. For the purpose of this, there is used a focal point detecting system 7 that is structurally integrated with the objective lens 16 for implementing the rigidity. The focal point detecting system 7 includes an oblique beam spot irradiating system 71 and a spot position detecting system 72. The oblique beam spot irradiating system 71 irradiates the fluorescent light plane on the DNA chip with the microscopic spots from an oblique direction.

The irradiation with the spots is performed, and the spacing between the objective lens 16 and the fluorescent light plane is detected. Then, the objective lens 16 is controlled so as to be driven in the z direction in accordance with the detection signal by an objective lens up-and-down driving mechanism 73 so that, even if a stage 80 for mounting the DNA chip 2 thereon is driven in x, y directions by a driving motor 83 (84), the above-described fixed spacing is maintained. A numeral 82 denotes a length-measuring device of x, y stage.

Figure 33:
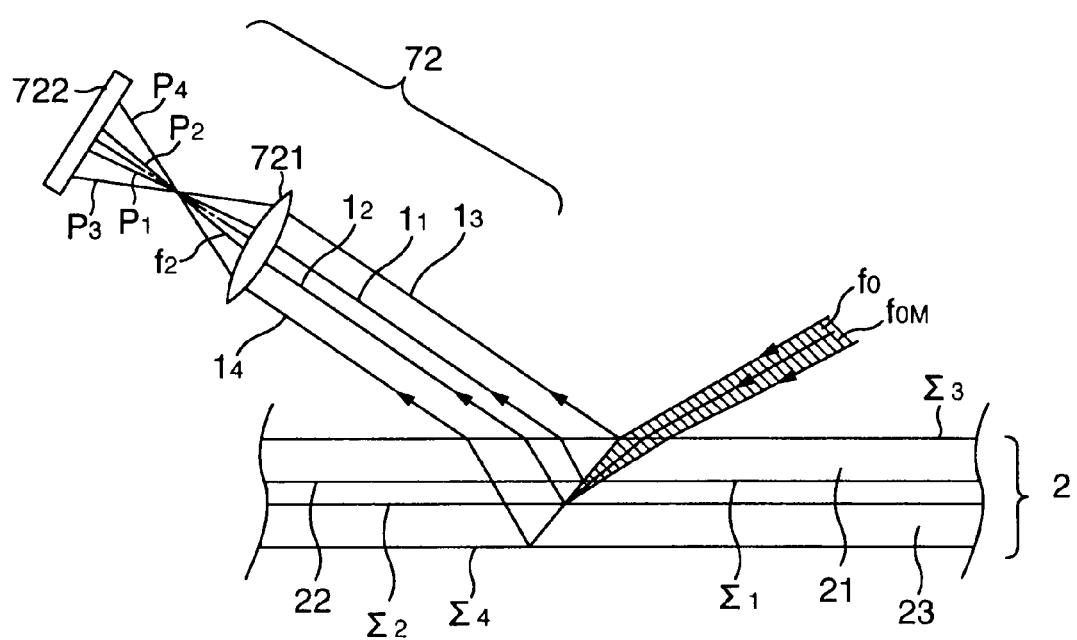
FIG. 33 is a diagram for illustrating a reflection response of the DNA chip in the focus detection in FIG. 32.

FIG. 33 illustrates an example of a cross sectional structure of the DNA chip. In this embodiment-illustrating diagram, the fluorescent light plane is a plane $\Sigma_2$. Namely, there exists the fluorescent light plane $\Sigma_2$ on a flat substrate 23 such as a glass. Between this plane and a plane $\Sigma_1$ on a glass substrate 21, there exists a clearance 22 into which a liquid containing the fluorescent material-added DNA to be inspected is poured for implementing the hybridization. At the stage of the DNA inspection, the clearance is filled with the liquid. However, depending on the cases, the clearance is left empty. Also, in some cases, the plane $\Sigma_1$ is selected as the fluorescent light plane, and the substrate 23 is composed of an opaque substance or a light-absorbing material.

A light beam $f_0$ irradiation of which is performed from an oblique direction by the oblique beam spot irradiating system 71 so that the light beam is converged onto the fluorescent light plane, is regularly reflected on the following 4 planes: An upper plane $\Sigma_3$ and the lower plane $\Sigma_1$ of the upper substrate 21, and the upper plane $\Sigma_2$ and a lower plane $\Sigma_4$ of the lower substrate 23. Light-rays $l_3$, $l_1$, $l_2$, and $l_4$, which are formed by the regular reflections of a primary light-ray $f_{0M}$ of the oblique irradiation beam $f_0$, are each image-formed by an image-forming lens 721 at positions $P_3$, $P_1$, $P_2$, and $P_4$ on a plane equivalent to a light-receiving plane of a light-receiving position sensor 722. The position of the fluorescent light plane is determined in advance and accordingly, if the respective planes $\Sigma_3$, $\Sigma_1$, $\Sigma_2$, and $\Sigma_4$ are away from each other to a certain extent, the following method makes it possible to execute the height detection of a desired detection plane alone: The dimension of the light-receiving position sensor 722 and the image-forming magnification of the lens 721 are determined beforehand so that only a spot image resulting from the reflected light-ray $l_2$ from the plane to be detected (which is $\Sigma_2$ in this embodiment-illustrating diagram) is received and the other spot images are image-formed outside the light-receiving aperture.

Namely, in this embodiment, it becomes possible to capture only the regularly reflected light reflected from the plane $\Sigma_2$ and thus to detect the spot position on the position sensor, i.e., the height position of the plane $\Sigma_2$. Then, based on this detected information and in accordance with the control apparatus 4, the objective lens and the focal point detecting system 7 integrated with the objective lens are displaced slightly in an up-and-down direction by the driving mechanism 73. This allows the fluorescent light detection to be executed always in the focus-achieving state.

If the incident angle of the oblique incidence focus detecting light in FIG. 33 is close to Brewster angle, causing the detecting light to be launched in the P-polarized state gives rise to an extremely small reflection on the plane surface, thereby making it difficult to execute the detection. Accordingly, there is employed the S-polarized detecting light. The employment of the S-polarization enhance the reflectance on the plane surface more in comparison with that of the P-polarization no matter what value the incident angle is. This is advantageous enough.

Figure 34:
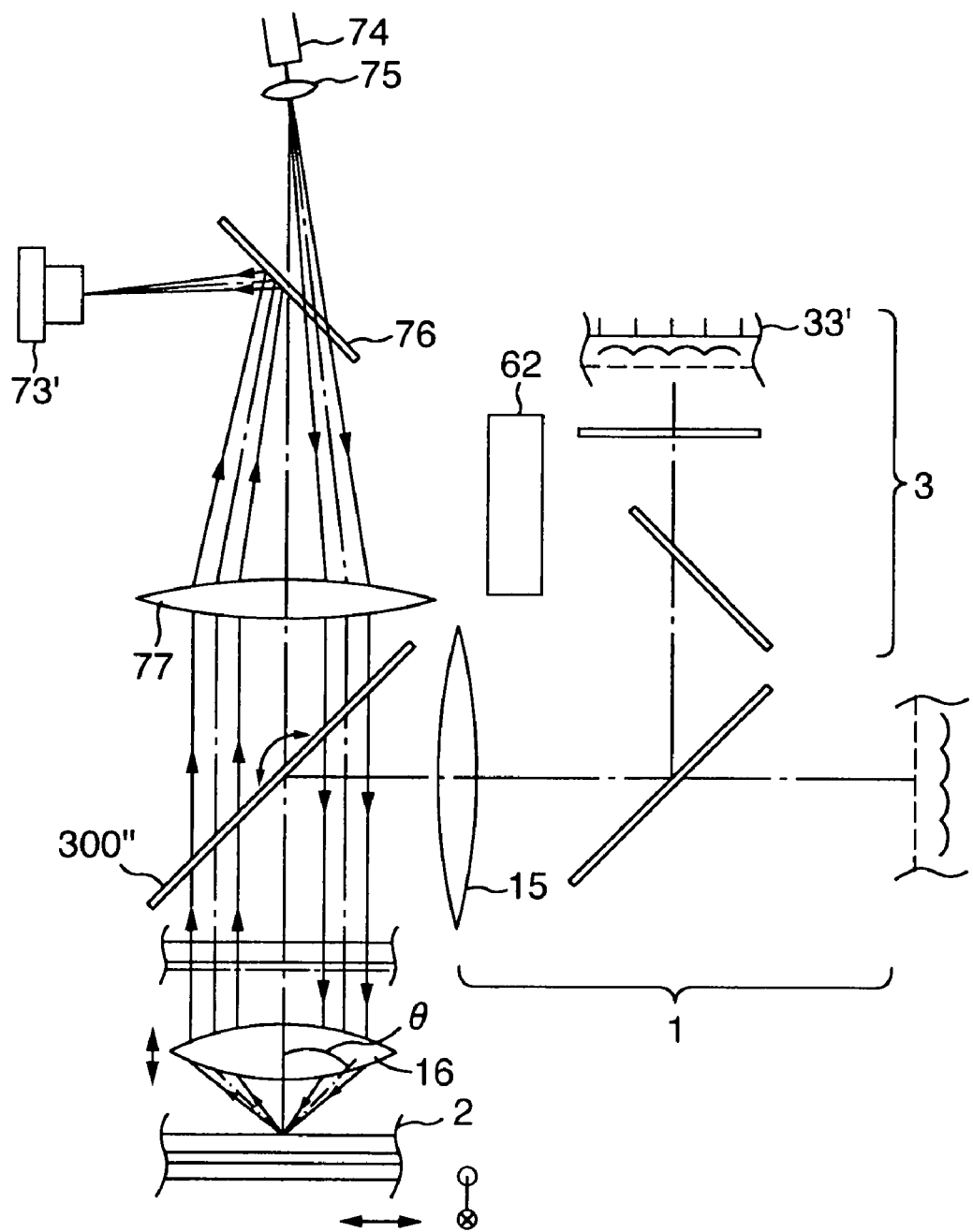
FIG. 34 is an embodiment-illustrating diagram in the present invention, where the focus detection is executed through the objective lens.

FIG. 34 is an embodiment-illustrating diagram in the present invention, where the focal point detection is executed through the objective lens 16. A laser light having been guided by a fiber 74 from a near-infrared semiconductor laser light-source not illustrated, after being emitted from the fiber, passes through a beam splitter 76, a lens 77, and a wavelength separating beam splitter 300". Then, the light passes through the objective lens 16 so as to be converged, and the fluorescent light plane on the DNA chip 2 is irradiated with the converged light from oblique directions. The incident angle θ of this irradiating light is equivalent to the numerical aperture NA of the objective lens in its magnitude (an incident angle that is somewhat smaller than sin θ=NA≈0.8). The regularly reflected light passes through the objective lens again, eventually forming, onto a position sensor 73', an image of the light-converged point on the DNA chip 2. Then, the position sensor 73' detects the position of this image. From this detected position, the height of the plane in the DNA chip can be determined. The objective lens is displaced in the up-and-down direction so that the image is image-formed at a reference point on the position sensor 73'. This, in the same way as the embodiment in FIG. 33, makes it possible to detect the focus position of the fluorescent light plane in the chip. Just like the present embodiment, by employing the light the wavelength of which is longer than that of the detected fluorescent light as the light to be used for the focal point detection, it becomes possible to execute the focal point detection precisely without exciting the fluorescent material, i.e., without generating the detection noise.

Incidentally, the wavelength separating beam splitter 300" in FIG. 34 permits the near-infrared light to pass through and reflects the excitation light and the fluorescent light used for the fluorescent light detection. The irradiation with a 1-dimensional excitation light spot array formed by a 1-dimensional excitation light irradiating optical system 1 is performed toward the fluorescent light plane in the DNA chip through the lens 15, the wavelength separating beam splitter 300", and the objective lens 16. A fluorescent light detecting optical system 3 detects the fluorescent light generated. The displacement of the excitation light spot array irradiating positions in the array direction is executed by causing the wavelength separating beam splitter 300" to perform the microscopic rotation.

Hereinafter, referring to FIGS. 35 to 40, the explanation will be given concerning a method of executing, all over the entire cells in the DNA chip, the fluorescent light detection toward the DNA chip that has been explained so far using the above-described respective embodiments.

Figure 35:
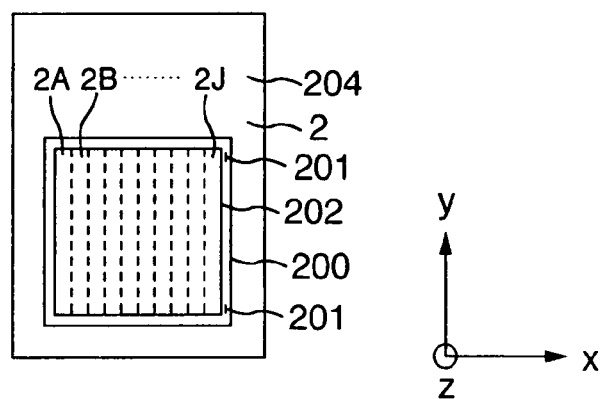
FIG. 35 is an embodiment-illustrating diagram in the present invention, which indicates a method of detecting the entire inspection target area of the DNA chip.

FIG. 35 illustrates the entire structure of the DNA chip. A numeral 204 denotes the whole case for housing the DNA chip. The DNA chip is a glass substrate on an inner side of a window 200 formed on this case, and the chip is fixed to the case 204. The fluorescent material-added DNA fragment is hybridized with an area 202 on the inner side of the window. In an area spreading outside the area 202 and inside the window 200, there are described alignment marks 201 for the positioning.

The relative positions between the cell 20 explained in FIG. 2 and the alignment marks 201 are designed and formed with an accuracy of several-tenth μm, the cell 20 including NXN (in FIG. 5, 5×5) pixels (indicated by the bold line) in which the fragment of the same DNA information is planted (i.e., the probing is performed).

The DNA chip is mounted on the detecting apparatus the embodiments of which have been explained already. Then, in an alignment detecting optical system (not illustrated) implemented in the detecting apparatus, using a device such as a mark position detecting 2-dimensional CCD, the positions of at least 2 of the alignment marks 201 are detected as positions on the CCD. Also, the position of the DNA chip at the time of executing this mark detection is detected using, for example as is illustrated in FIG. 32, the length-measuring devices 81, 82 for detecting the position in the x and y directions. The length-measuring devices are provided on a chuck on which the DNA chip is mounted.

The spacing between the optical axis of the above-described CCD detecting optical system and the detecting optical axis in the previously-described various types of fluorescent light detecting optical systems is fixed. This condition allows the pixels to be detected at the right positions from the above-described spacing, the above-described alignment mark detected positions by the CCD, and the detected position by the length-measuring devices, the pixels corresponding to more minute division of the inside of each cell on the DNA chip. At this time, if the detection of 2 or more of the alignment mark positions indicates that the DNA chip has been rotated, this rotation is corrected using a rotation mechanism not illustrated. Incidentally, the right position detection after this rotation correction is performed as necessary. Even if this rotation correction is not performed, if the amount of the rotation is small, it is also allowable to detect this rotation amount by the above-described method and to correct the x, y coordinates in accordance with the rotation amount detected. Also, it is possible to correct and detect the above-described multi-spot lights by a microscopic rotation of the optical system.

Figure 36:
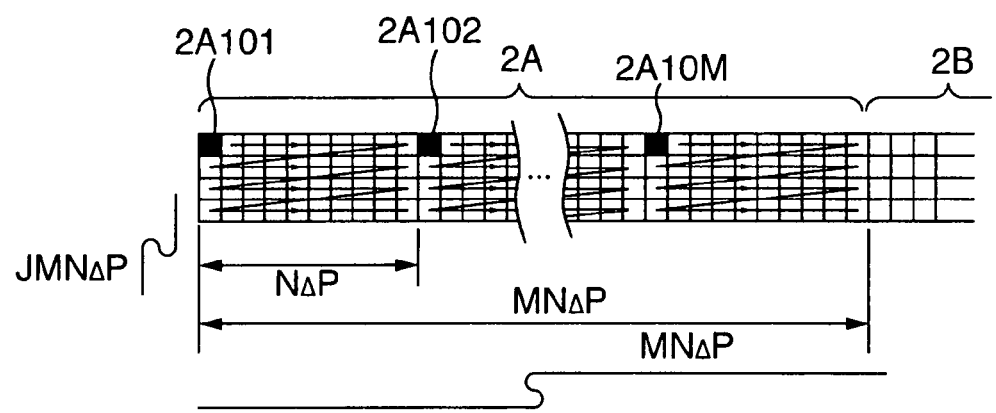
FIG. 36 is an enlarged explanatory diagram for explaining the embodiment in FIG. 35.

As having been explained so far, the detection of the alignment marks and the length-measurement of the DNA chuck make it possible to detect the pixels in each cell on the DNA chip with the precise positioning accuracy. As a consequence, in accordance with the following method, it becomes possible to execute the fluorescent light detection toward all the pixels in the chip in sequence, at a high speed, and without missing. A reference numeral 2A in FIG. 35 indicates an area detected by one scanning of the chuck. Here, the one scanning of the chuck is executed as follows: An operation of performing the irradiation with the M multi-spot array excitation lights, of performing the sequential scanning by the amount of N pixels in the spot array direction, and of returning the spot array back to an original operational position is repeated, and at the same time, the chuck is scanned in the y direction. Namely, as illustrated in FIG. 36, first, the pixels 2A101, 2A102, . . . , 2A10M on the DNA chip are illuminated and excited simultaneously. Next, the multi spots are displaced by the amount of one pixel-pitch $\Delta P$ by the above-described method, and this is continued in sequence.

When, in this way, the displacement by the amount of N(k) pixels is over, it turns out that the detection has been performed by the amount of MN(k) pixels in total, i.e., over a width of NM$\Delta$P, in a 1-dimensional array-like configuration. When the scanning by the amount of N(k) pixels has been finished, the multi-spot array is returned back to the original position. During this, the DNA chip has been displaced by the amount of one pixel in the y direction, which corresponds to a time-period from a time $t_0$ to $t_1$ of $y_{st}$ in FIG. 39. Consequently, during the time-period from the time $t_0$ to $t_1$, the repetition of the above-described operation by the number of the y direction pixels allows the fluorescent light detection to be finished toward all the pixels in the area 2A.

Figure 38:
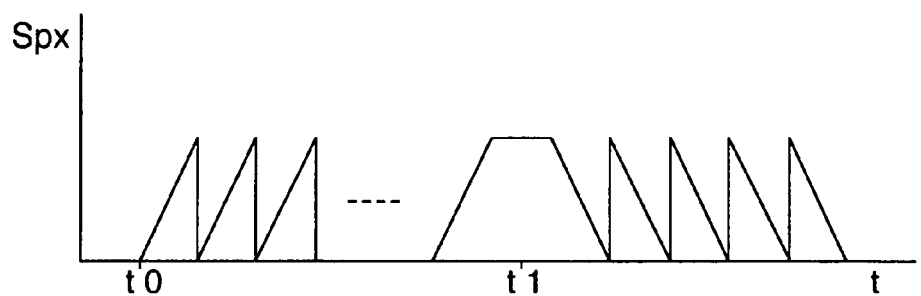
FIG. 38 is a diagram for indicating the movement of the multi spots in the embodiment in FIG. 35.
Figure 39:
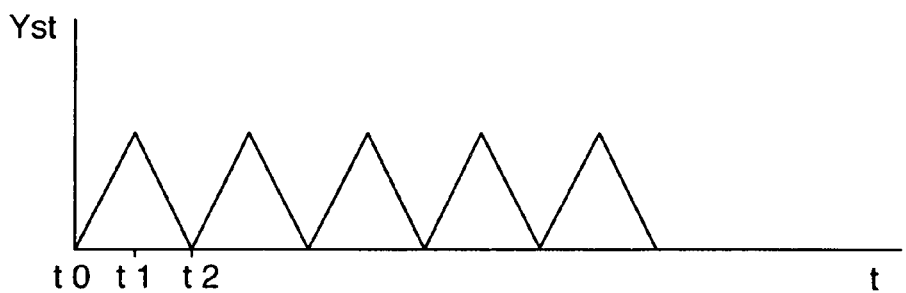
FIG. 39 is a diagram for indicating the movement of a DNA chip chuck in the x direction in the embodiment in FIG. 35.

In the case where the above-described operation is performed by the DNA detecting apparatus of the embodiment in FIG. 1, the driving signal of the multi-spot excitation lights by the AO deflector, or the displaced position of the spots is changed as is indicated by $S_{px}$ in FIG. 38. When seen in more detail, the driving signal or the displaced position is step-displaced just like $S_{B12}$ in FIG. 8. Also, the deflection signal of the wavelength selection beam splitter is changed similarly to $S_{px}$ in FIG. 38. The repetition of such changes from the time $t_0$ to $t_1$ permits all the area of the area 2A to be detected.

Figure 37:
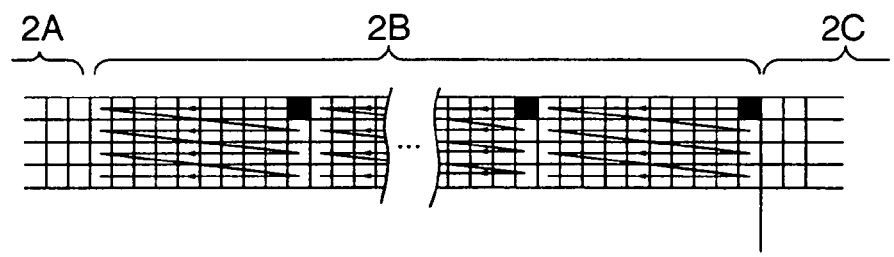
FIG. 37 is an enlarged explanatory diagram for explaining the embodiment in FIG. 35.
Figure 40:
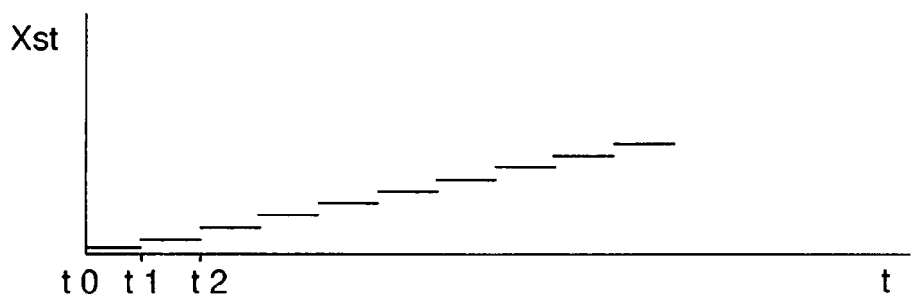
FIG. 40 is a diagram for indicating the movement of the DNA chip chuck in the y direction in the embodiment in FIG. 35.

When the detection has been performed to the end at the bottom of the area 2A (the time $t_1$), as is indicated by $x_{st}$ in FIG. 40, the DNA chip chuck is step-displaced over the width of NM$\Delta$P in the x direction. After the step displacement, as is indicated by $y_{st}$ after the time $t_1$ in FIG. 39, the chuck is scanned in an opposite orientation in the y direction. Simultaneously with this, just like $S_{px}$ after the time $t_1$ in FIG. 38, the deflection signal of the AO deflector 12 and that of the wavelength selection deflecting beam splitter 30 are scanned in an orientation opposite to the orientation at the time of detecting the area 2A (the time $t_0$ to the time $t_1$). This, as illustrated in FIG. 37, makes it possible to continuously detect an area 2B subsequently to the detection of the area 2A. By repeating the above-explained operation alternately in the − orientation and the + orientation concerning the y direction of the DNA chip, it becomes possible to detect all the areas 2A to 2J on the DNA chip at a high-speed.

Next, the explanation will be given below concerning a time needed to detect all the pixels on the DNA chip. Representing the cell number in the chip by L, each cell is divided into the N×N pixels so as to avoid the influences of the foreign substance and the like. This makes the total detection pixel number in the chip equal to $LN^2$. Setting the simultaneous irradiation spot number of the multi-spot excitation lights and a time needed for the detection with the multi spots to be M and $\Delta t$, respectively, and ignoring a time for the spot displacement and a time for the chuck movement in the x direction since these times can be assumed to be shorter as compared with the fluorescent light detecting time, the total fluorescent light detecting time T is given by the following equation:

$$T=LN^2\Delta t/M=LN^2/(M/\Delta t)$$

With reference to the number k of the scannings with the multi spots, a response time $T_p$ of the wavelength separating beam splitter 30 needs to be $k\Delta t$ or larger. Also, the light-source power needs to be $\beta M/\Delta t$ or larger. Also, it is desirable that the spacing between the excitation multi-spot lights be equal to 5 or more in view of the signal-to-noise ratio.

At a longer fluorescent light wavelength of 670 nm, the quantum efficiency of the photomultiplier tube used for the fluorescent light detection becomes considerably small, i.e., 5 to 10%. Also, there exists a limit to the output of the laser light used for the excitation. Taking such conditions into consideration and in order to execute the detection as fast as possible, letting, for example, k (=N)=10, M=50, $\Delta t$=50 µs, the cell number L=1000×1000, and the in-cell division pixel number N=5, T becomes equal to 25 s. Namely, this result satisfies the condition of the fluorescent light detecting time that is smaller than $LN^2/(6 \times 10^5)$sec. Additionally, substituting the above-described values of L and N into this condition, the result is found to be 42 sec. This value satisfies the condition of executing the detection within 1 minute, including attachment/detachment of a sample chip for the use other than the fluorescent light detection, inputting of the inspection conditions, and outputting of the result.

Allowing the detection to be executed in 1 minute exhibits an outstanding effect in the case where a lot of specimens to be detected are inspected. For example, 1 minute becomes sufficient to execute an inspection that has necessitated 5 minutes conventionally. Accordingly, even if a preprocessing spends somewhat a longer time, when the number of the specimens becomes around 100, it becomes usually possible to execute the preprocessing in parallel to the inspections of the large number of specimens. This makes it possible to shorten the detecting time by 5 or 6 hours.

The reasons why the present invention permits such a high-speed and high-accuracy detection to be implemented are as follows: The multi spots are used as the excitation lights simultaneously. Moreover, in the fluorescent light detection by each multi-spot excitation light, the detection is executed in a state of enlarging the spot spacing enough so that the influences of the other excitation spot lights can be suppressed up to the smallest possible degree.

FIGS. 41A, 41B, 41C, and 41D are diagrams for illustrating an embodiment of the method and units for obtaining the multi-spot lights according to the present invention.

Using a method described later, substantially parallel laser beams emitted from one light-source or a plurality of light-sources are formed into a plurality of (in the drawing, an even number) N/2 laser beams that are parallel to each other with a pitch of several mm and that travel in the same direction, then being formed into N laser beams (N is an integer) by N/2 beam-doubling prisms 411, 412 and so on. As illustrated in an enlarged perspective view in FIG. 48B, the beam-doubling prism has a cross section of a triangle and a cross section of a parallelogram. Here, the triangle has an oblique side forming an angle of substantially 45 degrees toward the light-emitting surface, and the parallelogram is in contact with this oblique plane and has a total reflection plane that is parallel to this oblique plane.

A light launched into the one side of the parallelogram is reflected on a beam split plane of the triangle oblique plane by the amount of substantially 50%, and the remaining substantially 50% passes through the beam split plane. The light having passed through the beam split plane passes through the prism of the triangle without being subjected to any change. Meanwhile, the reflected light undergoes a total reflection on the other plane of the parallelogram, then passing through the prism of the parallelogram. In this way, the light having passed through the triangle prism and the light having passed through the parallelogram prism are parallel to each other and have substantially the same intensity. Also, the spacing between both of the lights becomes equal to P. As a result, the beam spacing between the adjacent multi beams has become equal to P, which is one-half of the beam spacing 2P of the laser beams 81e.

In this way, by a beam-doubling prism array 4e where such beam-doubling prisms are arranged by the number of N/2 with the pitch of 2P, the laser beams 81e are formed into the plurality of N laser beams 8e which travel in substantially the same direction with the pitch of P and the adjacent beams of which are proximate to each other. The plurality of N laser beams 8e, by being launched into a polarization component 11e described later, are formed into a plurality of 2N laser beams which travel in substantially the same direction and the adjacent beams of which are proximate to each other.

Figure 42:
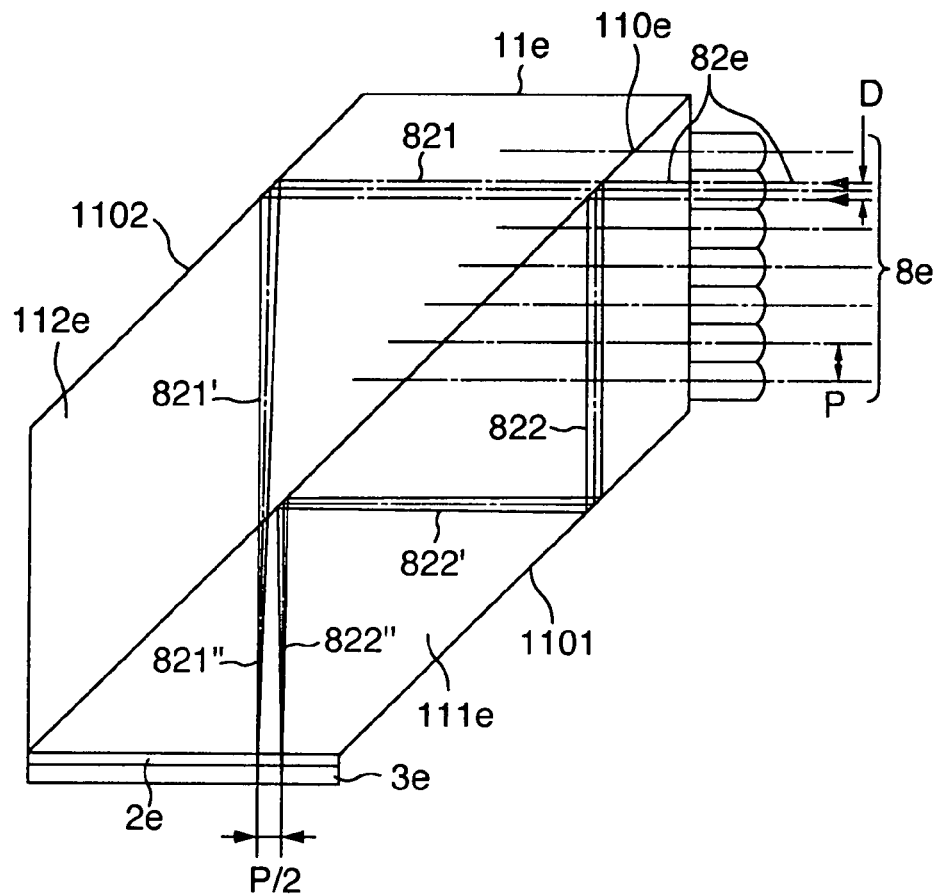
FIG. 42 is a front view for illustrating the configuration of an embodiment of the multi-spot light forming unit according to the present invention.

As illustrated in FIG. 42, the polarization component 11e includes the 1st multi-spot lights-doubling prism that has a polarization beam split plane 110e and transparent prisms 111e, 112e. Here, the transparent prisms each have total reflection planes 1101, 1102 that are parallel to the polarization beam split plane 110e and are positioned at distances of L1 and L2 from the polarization beam split plane 110e. On a light-receiving plane of the polarization component 11e toward the N beams, there are located strip-shaped convex lenses such as 21e, 22e, which result from cutting a spherical flat convex lens into strip-shaped configurations, by the number of N in such a manner as to correspond to the positions of the respective N parallel beams. Here, the enlarged diagram and the cross sectional enlarged diagram of the strip-shaped convex lenses are illustrated in FIGS. 49A to 49D and FIG. 42, respectively. The laser beams having passed through an array 20e of these strip-shaped convex lenses, as illustrated in FIG. 42, become converged lights each, then being launched into the polarization beam split plane in parallel to each other.

The respective converged beams are circularly polarized lights or linearly polarized lights polarized at 45 degrees toward the polarization beam split incidence plane 110e. Consequently, as illustrated in FIG. 42, an S-polarized component of an incident light 82e is reflected on this plane, and a P-polarized component thereof passes through this plane. As illustrated in FIG. 42, a reflected converged light 822 passes through the prism 111e, then being launched into the plane 1101 parallel to the polarization beam split plane 110e at an incident angle of 45 degrees. A converged beam 822' that has undergone a total reflection on the plane 1101 is S-polarized, and thus is reflected on the beam split plane 110e again. A reflected converged beam 822", passes through the prisms 111e, then going through.

Meanwhile, with respect to the P-polarized component, a converged beam 821 having passed through the beam split plane 110e passes through the prism 112e, then being launched into the plane 1102 parallel to the beam split plane 110e at an incident angle of 45 degrees. The reflected light becomes a totally reflected converged beam 821', then being launched into the beam split plane 110e again. The incident light is P-polarized, and thus passes through the beam split plane by substantially 100%. This transmittance light 821" passes through the prism 111e, then going through.

The total reflection planes 1101, 1102 of the prisms 111e, 112e are positioned at the distances of L1 and L2 from the beam split plane. The values of L1 and L2 satisfy the following relation: $\sqrt{2}$ (L2−L1) is equal to P/2 that is one-half of the pitch P of the N parallel beams 8. Accordingly, when the lights having been separated by the beam split plane go through the polarization component, the two lights are shifted to each other by the amount of P/2. As a result, the N converged beams with the pitch of P that have been launched into the polarization component 11e pass through the polarization component 11e in a state of being formed into 2N converged beams with the pitch of P/2.

Figure 43:
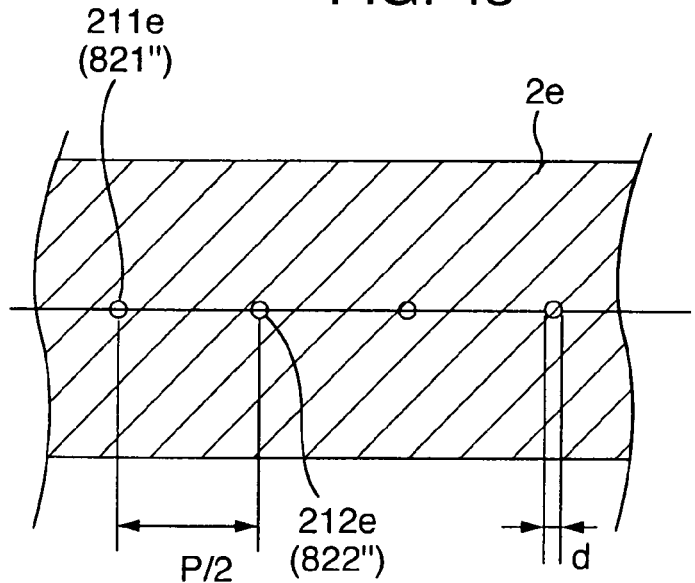
FIG. 43 is a front view for illustrating an embodiment of a mask according to the present invention.

On a light-emitting plane of the prism 111e in the polarization component 11e, as illustrated in FIG. 43, there is located a pinhole array mask 2 where pinhole apertures 211e having a diameter d are arranged by the number of 2N with a pitch of P/2. The converged lights pass through the pinhole apertures. Since the portion other than the 2N pinhole apertures light-shields lights, the pinhole array mask 2 light-shields a stray light differing from the converged lights and becoming a noise light. As a result, the lights having passed through the pinhole array mask generate spot array lights only from the pinhole portions.

The lights having passed through the pinhole array 2e are linearly P-polarized lights and linearly S-polarized lights alternately every adjacent spots. Directly behind the pinhole array 2e, there is located a quarter wave plate 3e. The quarter wave plate is set in such a manner that the optical axis forms 45 degrees toward the P-polarized and S-polarized directions. Consequently, the P-polarized and the S-polarized lights having passed through the quarter wave plate 3e become right-handed and left-handed circularly polarized lights, respectively.

The 2N parallel circularly polarized lights having passed through the quarter wave plate 3e are launched into a polarization component 12e. The polarization component 12e is a polarization beam splitter the structure of which is substantially the same as that of the above-described polarization component 11e. Namely, a beam split plane 120e permits a P-polarized light to pass through and causes an S-polarized light to be reflected. Also, the values of L1' and L2' satisfy the following relation: $\sqrt{2}$ (L2'−L1')=±P/4. Here, L1' denotes a distance between the beam split plane and a total reflection plane 1201 of a prism 121e through which the S-polarized light passes after having been reflected by the beam split plane. L2' denotes a distance between the beam split plane and a total reflection plane 1202 of a prism 122e through which the P-polarized light passes after having been reflected by the beam split plane. By providing the above-explained configuration, the 2N parallel beams with the pitch of P/2 that have been launched into the prism 12e are formed into mutually parallel 4N diverged beams with a pitch of P/4, then being emitted from the prism 12e.

As described above, the lights emitted from the 2N spots existing on the pinhole array mask are formed into the above-described 4N multi-spot lights by the polarization component 12e. At this time, the polarization component 12e makes the 4N multi-spot lights look as if the multi-spot lights were emitted from the surface of the mask 2e. Namely, when seen from the side on which the multi-spot lights have already passed through the polarization component 12e, the 4N multi-spot lights are formed on the surface of the mask 2e, then being emitted therefrom in the state of having become the diverged lights. This phenomenon is caused by a mirror image effect by the reflection planes 120e, 1201, and 1202.

As one example, assuming that the number of N is equal to 16 and the pitch P is equal to 1.6 mm, in the above-described embodiment, the number of the multi-spot lights and the pitch become equal to 64 and 0.4 mm, respectively. By launching the multi-spot lights into an objective lens of an infinite focal point microscope through an image-forming lens, assuming that the magnification of the optical system is 20 times, it becomes possible to irradiate a sample, i.e., a target to be inspected, with 2 μm-diameter spots with a 20 μm pitch by the number of 64 simultaneously. This will be explained in detail later.

In the above-described embodiment in FIG. 41A, the N/2 multi beams are launched into the 2nd beam-doubling prism array 4e. When N is equal to 8, if the laser light-source is not the He—Ne laser type producing a large output but a large intensity is required as the irradiation light, it is sufficient to prepare, for example, 8 He—Ne lasers and to launch the lasers into the 2nd beam-doubling prism array 4e with a 1.6 mm pitch. Also, it is sufficient that 8 semiconductor lasers are used and are formed into mutually parallel beams, thereby configuring 8 beams as is the case with the above-described He—Ne lasers so as to launch the lasers into the 2nd beam-doubling prism array 4e. In this case, since the pitch P is set to be 1.6 mm, the spacing 2P between adjacent beams of the 8 laser beams becomes equal to 3 mm, which is greater than the beam diameter of the He—Ne laser light, i.e., 1 mm. Accordingly, it is possible to launch the lasers in parallel to each other from the 8 laser light-sources.

In this way, even in the state where, by the 2nd beam-doubling prism array, the pitch is made equal to the spacing P that is less than 4 times as great as a diameter d of the beams emitted from the laser light-source, i.e., $4d$ or less, causing the beams to be launched into the multi-spot light forming unit using the polarization component allows the spacing to be made equal to ½ thereof. Also, using the polarization component a plurality of n times allows the spacing to be made equal to $½^n$ thereof. In this way, it becomes possible to execute the conventionally difficult following task: Converting the plurality of N laser beams, which are launched with the pitch that is less than 4 times as great as the beam diameter d, into the $2^{M'}N$ multi laser beams with the pitch of $P/2^{M'}$, thereby allowing the multi-spot lights to be formed with a high-efficiency.

Figure 44:
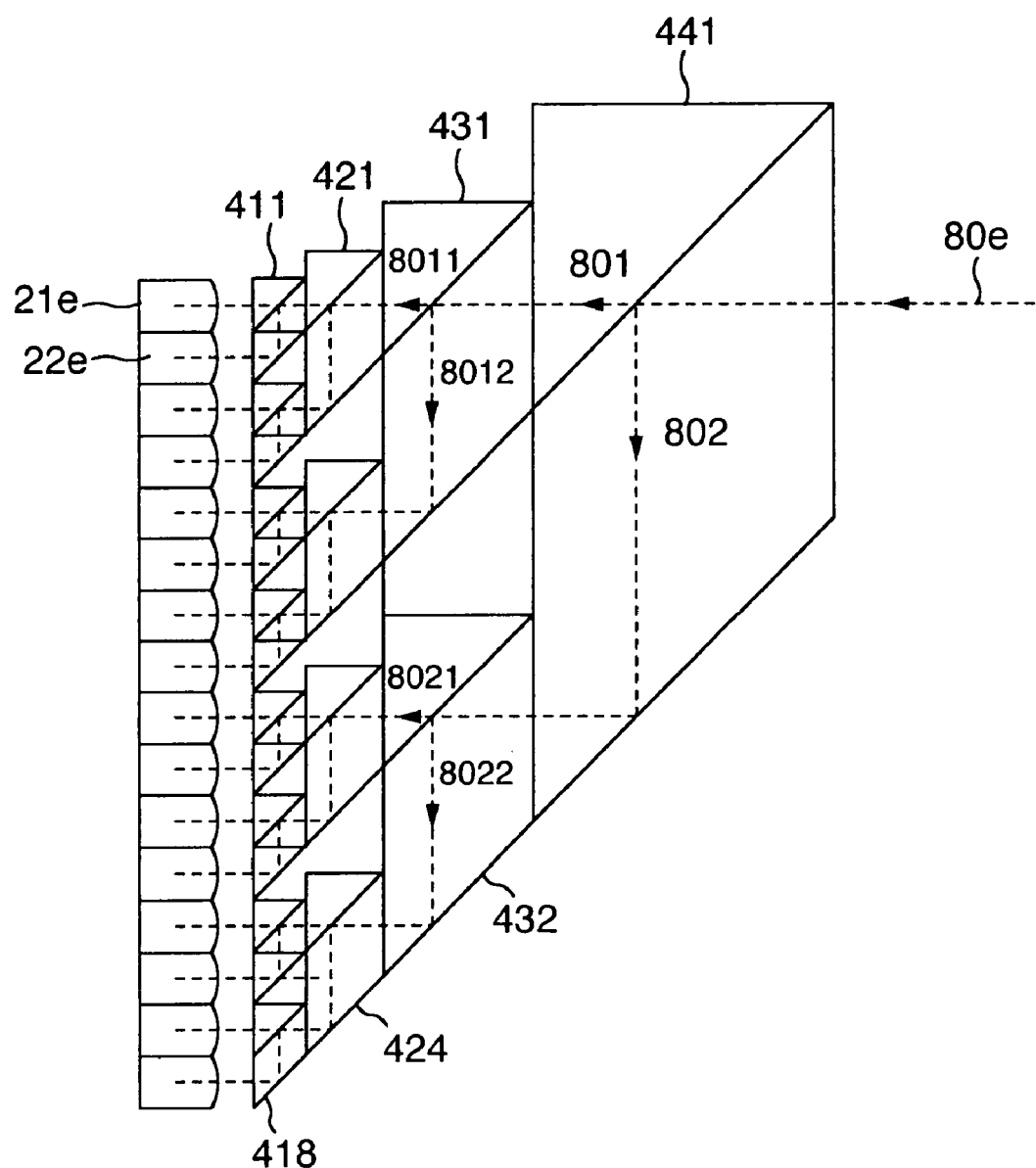
FIG. 44 is a front view for illustrating the configuration of an embodiment of the multi-spot light forming unit according to the present invention.

FIG. 44 is a diagram for illustrating another embodiment for forming the multi-spot lights according to the present invention. In the present embodiment, the N multi beams to be launched into the polarization component are formed using one laser light-source. For example, in the case where, like YAGSHG laser, the output of the light-source is large, the one laser light-source is effective enough. In such a case, as illustrated in FIG. 44, in addition to the 2nd beam-doubling prism denoted by 4e in FIG. 41A, the 2nd beam-doubling prisms the dimensions of which are 2 times, 4 times, and 8 times the dimension of the above-described 2nd beam-doubling prism 4e are arranged in a cascaded manner at n=4 stages in total.

Namely, one beam 80e emitted from one light-source is launched into the 8-times-dimensioned beam-doubling prism 441, thereby obtaining 2 beams 801 and 802 with a spacing of 8P. The 2 beams are launched into the 4-times-dimensioned beam-doubling prisms 431 and 432, thereby obtaining 4 beams 8011, 8012, 8021, and 8022 with a pitch of 4P. The 4 beams are launched into the 2-times-dimensioned beam-doubling prisms 421, 422, 423, and 424, thereby obtaining 8 beams with a pitch of 2P. The 8 beams are launched into the previously-mentioned 8 beam-doubling prisms 411, 412, 413, 414, 415, 416, 417, and 418 illustrated in FIG. 41B, thereby obtaining 16 beams with a pitch of P. This allows the 16 beams with the 1.6 mm pitch to be obtained from the one beam emitted from the one laser light-source.

The method explained in the above-described embodiment makes it possible to form the multi-spot lights having a total energy that is 70% or more of the energy of the laser beam emitted from the laser light-source, which was impossible in the prior art.

Moreover, taking the following measures makes it possible to form the multi-spot lights having a total energy that is 90% or more of the energy of the laser beam emitted from the laser light-source: Equipping the optical components with an anti-reflection coat, providing the optical components with a multi-layer coat for lowering the loss at the time of the beam separation, performing positioning of the incident lights toward the pinhole array, or the like.

Furthermore, the method explained in the above-described embodiment makes it possible to restrain the variation in the respective spot energies among the multi-spot lights within ±20%, which was impossible in the prior art.

Still further, taking the following measures outstandingly lowers a variation in the beam intensity caused by the reflection and the interference of the beams on the optical component surfaces, thereby making it possible to form the multi-spot lights that allow the variation in the respective spot energies among the multi-spot lights to be restrained within ±10%: Submitting conditions on the multi-layer coat at the time of the beam separation and controlling the manufacturing thereof, or bonding, with an optical adhesive, the mutually adjacent components out of the optical components such as the polarizer 11e in FIG. 41A, the strip-shaped convex lens array 20e the detail of which is illustrated in FIG. 41C, the pinhole array 2e, the wavelength plate 3e, and the polarizer 12e.

Incidentally, although, in the above-described embodiments, the explanation has been given concerning the case of forming the 64 or 16 multi-spot lights, the present invention is not limited thereto and is effective in the case of N=2, i.e., the case of obtaining 8 or more of the multi-spot lights.

Next, referring to FIG. 45, the explanation will be given below concerning an embodiment where the beams obtained by the multi-spot light forming methods explained so far are applied to the fluorescent light detection, especially to the DNA inspection using the fluorescent light detection.

Figure 45:
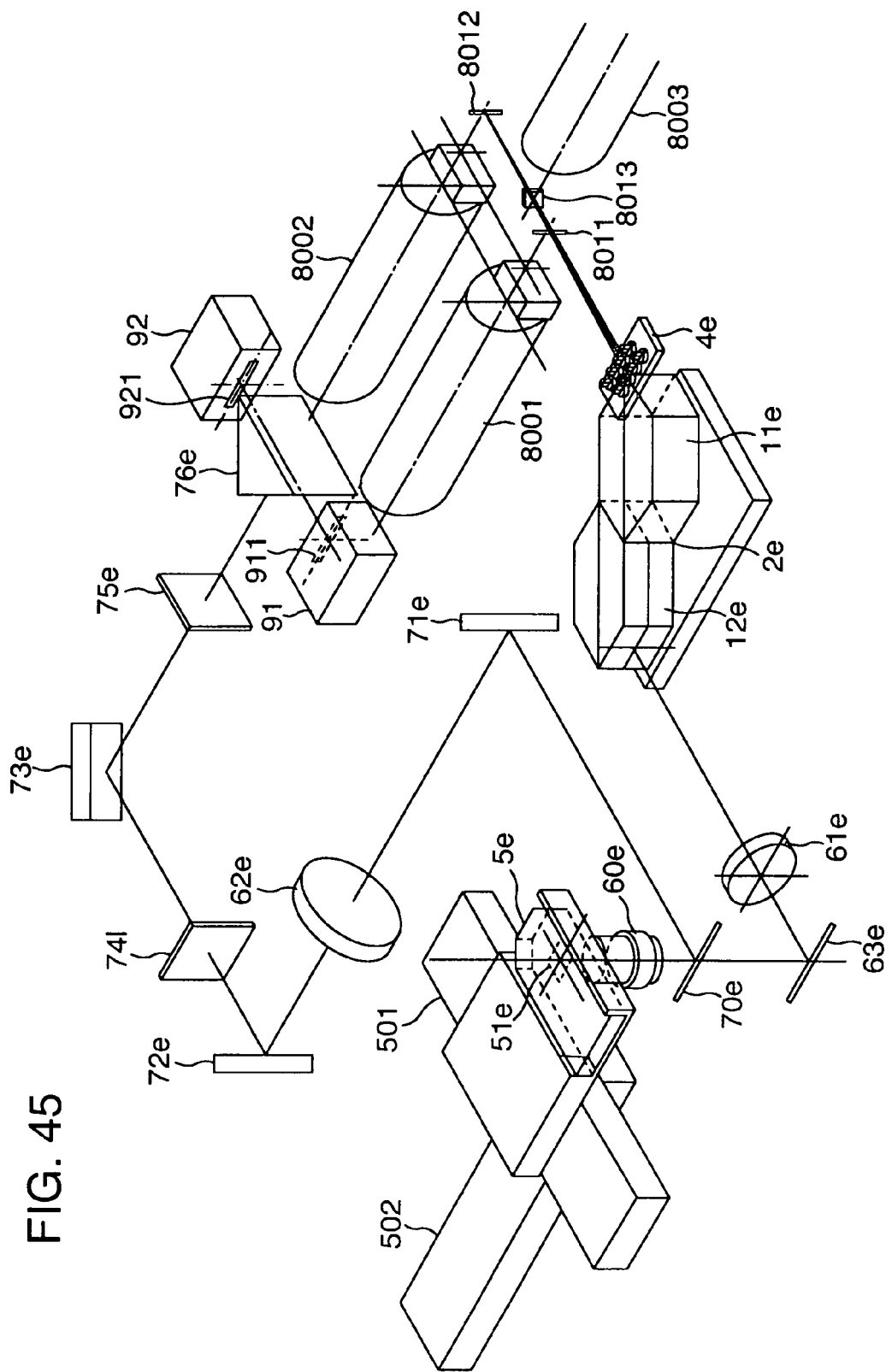
FIG. 45 is a perspective view for illustrating the configuration of an embodiment of the fluorescent light detecting and DNA inspecting apparatus according to the present invention.

In FIG. 45, numerals 8001, 8002, 8003, . . . , denote laser light-sources, and include 8 lasers in total that are not illustrated though. The beams emitted from the respective laser light-sources are directed into one direction in parallel to each other with a pitch of about 1.6 mm by mirrors 8011, 8012, 8013 . . . that are several mm in size. The 8 beams are obtained by the above-described method from the polarization component 12e as if the 64 multi-spot lights were emitted from the mask surface 3e with the 0.4 mm pitch. The 64 multi-spot lights pass through an image-forming lens 61e, a mirror 63e, a wavelength selection beam splitter 70e, then being illuminated onto an inspection plane 51e of a DNA chip 5e through an objective lens 60e.

On the surface of the DNA chip, there has been performed in advance the probing of a DNA determined for each of predetermined positions. Meanwhile, a target DNA obtained by adding a fluorescent material to a DNA formed by refining and amplifying a living body is poured onto the above-described probe DNA. Then, if the nucleotide sequence of the probe DNA and that of the target DNA correspond to each other, they are hybridized with each other. As a result, the fluorescent material-added target DNA is coupled with the probe DNA.

There exist various types of fluorescent materials to be added to the target DNA. The fluorescent material in the present embodiment absorbs the He—Ne laser light at the wavelength of 633 nm and emits the fluorescent light at the wavelength of 670 nm. The fluorescent light is received by the objective lens 60e, and the transmittance light is reflected by the wavelength selection beam splitter 70e, thereby being guided into a detecting optical system. The wavelength selection beam splitter 70e is a multi-layer coat beam splitter for permitting the 633 nm light to pass through and causing the 670 nm light to be reflected.

The fluorescent light reflected at the beam splitter 70e is reflected at a mirror 71e, then passing through an image-forming lens 62e. The image-forming lens 62e is configured as a telecentric optical system, so that primary light-rays of the fluorescent lights, which have been generated from the respective multi-spot lights with which the fluorescent materials on the DNA chip surface are irradiated, travel in parallel to each other after passing through the image-forming lens 62e. As a consequence, at an incident angle that is common to all the fluorescent lights, a fluorescent light generated from whatever multi-spot light is launched into a wavelength separating beam splitter reflecting the fluorescent lights at the above-described wavelength. This condition permits the 633 nm excitation light to pass through the beam splitter in a state of being scarcely reflected. Here, the 633 nm excitation light is a noise component contained slightly in amount in the fluorescent light generated from whatever multi-spot light. Namely, although the 633 nm excitation lights reach a wavelength separating beam splitter 72e slightly in amount, the excitation lights are caused to pass through the beam splitter. As a result, only the fluorescent lights are reflected, then traveling toward detectors 91, 92.

The above-described excitation light, which has been reflected on the DNA chip and then travels toward the detector side, has a light intensity that is stronger by several orders or more in comparison with a light intensity of the fluorescent light generated. On account of this, as described above, it is impossible to separate the excitation lights using the wavelength separating beam splitter 70e alone. In particular, the incident angles of the excitation lights into the beam splitter 70e differ, depending on the positions of the excitation light spots. Accordingly, it is impossible for any spot to eliminate the corresponding excitation light equally. In contrast to this, as explained above, the wavelength separating beam splitters 72e, 73e located between the telecentric image-forming lens 62e and the detectors 91, 92 are capable of reflecting the light from whatever spot position on the same incidence condition. The elimination of the excitation lights like this and interference filters 74e, 75e light-shield the excitation lights almost completely, allowing only the fluorescent lights to be taken into the detectors.

The detectors 91, 92, which are multi-channel photomultiplier tubes, have 32 light-receiving apertures each. Spot images of the fluorescent lights are separated into two by a right-angled mirror 76e located in front of the photomultiplier tubes 91, 92, then being image-formed at substantially the positions of the light-receiving apertures of the photomultiplier tubes. There exist pinhole arrays in front of the light-receiving apertures of the photomultiplier tubes. The pinhole arrays have apertures and a pitch that are substantially equal to the dimensions of spot images that are image-formed by the DNA chip-irradiating 2 μm-diameter and 20 μm-pitch excitation multi-spot lights with a magnification M of the objective lens and the image-forming lens. Namely, the pinhole arrays have the apertures 2M μm in diameter and the pitch of 20M μm. The pitch of 20M μm is equal to a light-receiving aperture pitch of the photomultiplier tubes.

This corresponds to performing the simultaneous irradiation with the multi-spot light array and performing the confocal point detection toward the generated fluorescent lights, thereby making it possible to execute the fluorescent light detection having a high signal-to-noise ratio. The 64 signals obtained are amplified by a circuit not illustrated, and are converted into digital information by an A/D (analogue/digital) converter, thus being transferred to a CPU (processing circuit) not illustrated. Then, data on the fluorescent light intensities at the irradiation positions is stored.

Stages 501, 502 are driven, thereby determining the fluorescent light intensities at the different positions in sequence in accordance with the above-described method. In order to execute the fluorescent light detection having a high signal-to-noise ratio, the pitch of the irradiation spots is made equal to several to tens of times the diameter of the irradiation spots. Accordingly, so as to accomplish the entire surface detection all over the target to be inspected, the detection is performed by driving the xy stage not only in a direction perpendicular to the arrangement of the multi-spot lights but also in the arrangement direction.

Figure 46:
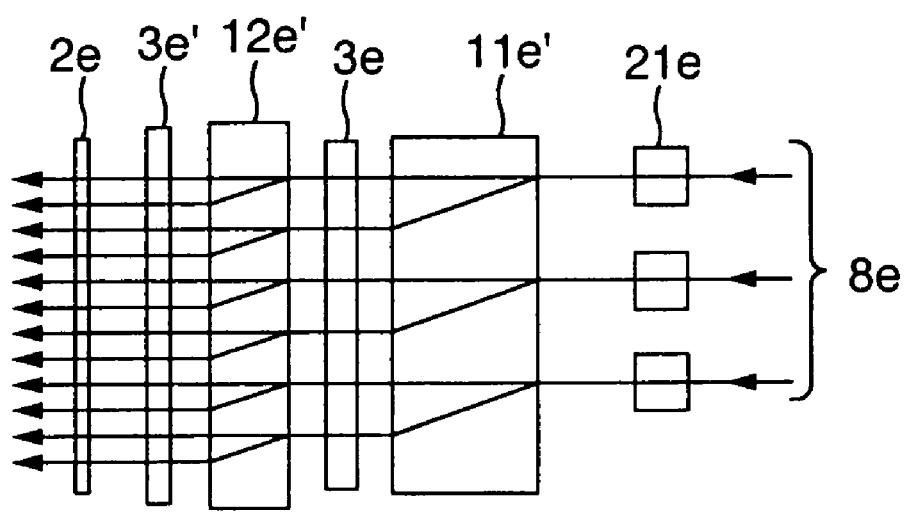
FIG. 46 is a front view for illustrating an embodiment of the multi-spot light forming unit according to the present invention.

FIG. 46 is a diagram for illustrating an embodiment in the present invention. The parallel beams 8e emitted from the one laser light-source or the plurality of laser light-sources are the circularly polarized lights or the linearly polarized lights polarized at 45 degrees toward the paper surface. One beam among the plurality of parallel beams 8e is launched into the one lens 21e within the array 20e of the strip-shaped convex lenses and becomes the converged beam, then being launched into a birefringent material such as calcite. A polarized component of an ordinary ray thereof travels straight without being altered, and a polarized component of an extraordinary ray thereof is refracted. A thickness of this polarization component is set so that a spacing between the ordinary ray and the extraordinary ray at the time of having passed through the polarization component becomes equal to one-half of the arrangement pitch P of the plurality of N incident beam lights 8e. As a result, after having passed through the polarizer 11e', 2N converged beams travel with a pitch of P/2 in parallel to each other.

In the respective beams, the polarized directions in their linearly polarized states differ from each other alternately by 90 degrees. The respective beams are caused to pass through the quarter wave plate 3e having the optical axis that forms 45 degrees toward the polarized directions, or a half wave plate 3e having an optical axis that forms 22.5 degrees toward the polarized directions, thereby obtaining circularly polarized lights or linearly polarized lights having polarized directions polarized at ±45 degrees toward the paper surface. These 2N beams are launched into a polarizer 12e'. The polarizer 12e, is a calcite the thickness of which is one-half of that of 11e'. The beams have passed through the polarizer 12e', which obtains 4N converged beams with a pitch of P/4.

These lights are caused to pass through a wavelength plate 3e' that is the same as the above-explained wavelength plate, thereby becoming circularly polarized lights or linearly polarized lights polarized at 45 degrees toward the paper surface. These multi beams are launched into a plate 2e including a multi-aperture array that has a pitch and an aperture diameter. Here, the pitch is equal to the pitch of the multi beams, and the aperture diameter is substantially equal to a converged diameter determined by the lens 21e and the diameter of the beams launched into the lens. This makes it possible to obtain noise-free multi-spot lights including only the lights having passed through the apertures.

Figure 47:
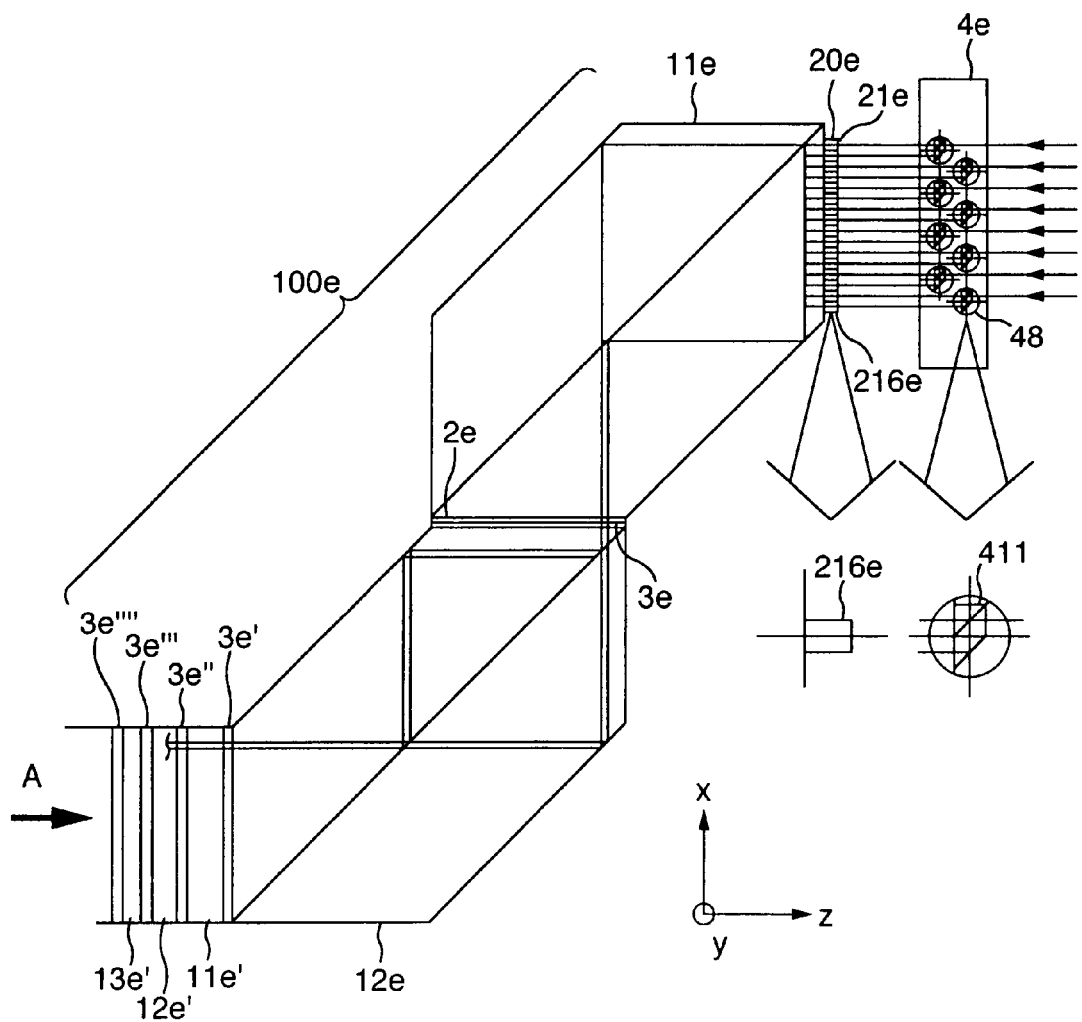
FIG. 47 is a front view for illustrating an embodiment of a 2-dimensional multi-spot light forming unit according to the present invention.

FIG. 47 is an embodiment-illustrating diagram for indicating a multi-spot light forming method used for the confocal point detection in the present invention. In FIG. 47, the same reference numeral as that in FIGS. 41A to 41D denotes the same component. The beams emitted from 1e or the plurality of laser light-sources are formed into the 8 parallel beams, then being formed into the 16 parallel beams by the 2nd beam-doubling prism 4e. The 16 parallel beams are formed into the converged beams by the convex lens array 20e.

Figure 48:
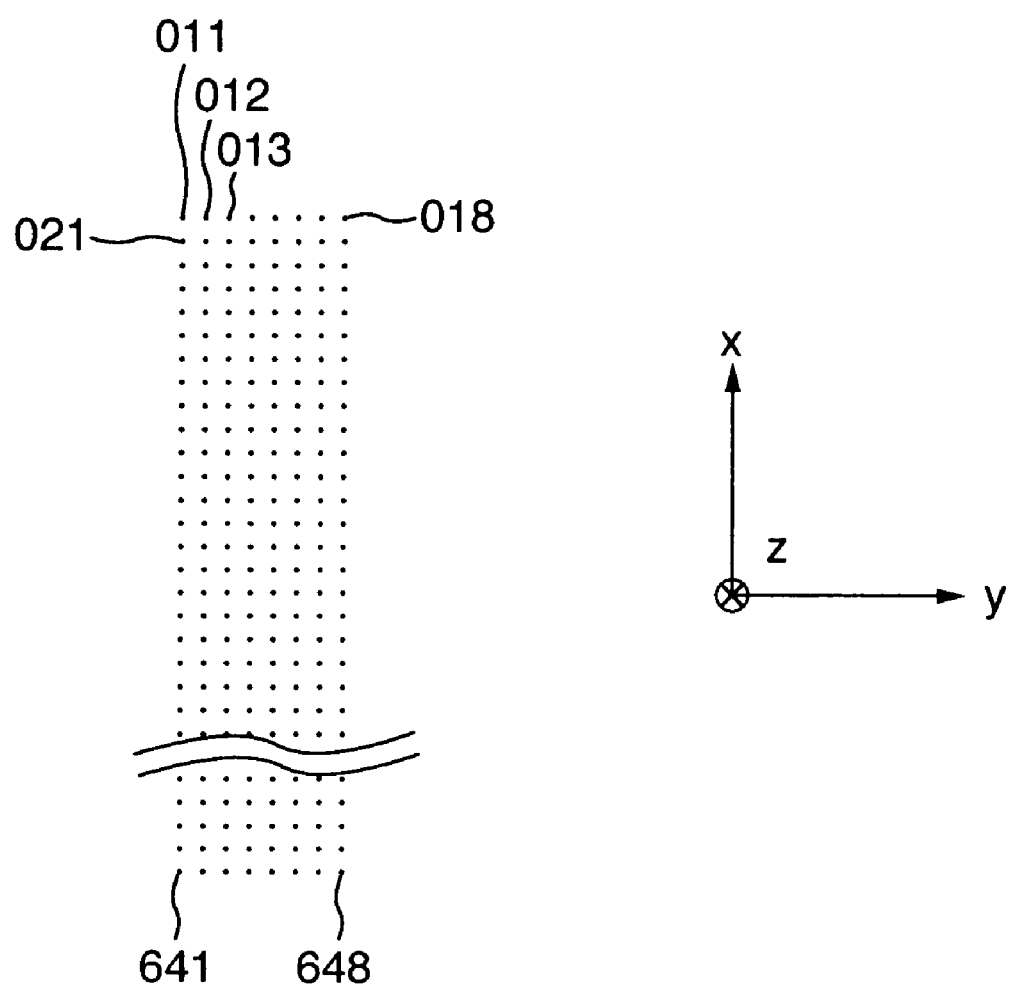
FIG. 48 is a front view for illustrating an example of the arrangement of the 2-dimensional multi-spot lights according to the present invention.

Then, the 1st multi-spot lights-doubling prisms 11e, 12e form the 64 multi-spot lights. At this time, the 64 multi-spot lights are obtained as if the 64 multi-spot lights were emitted effectively from the apertures of the mask 3e by the operation of the 1st multi-spot lights-doubling prism 12e. A quarter wave plate 3e' is attached to a light-emitting surface of the multi-spot lights-doubling prism 12e. Thus, the 64 multi-spot lights become circularly polarized lights, then being launched into a polarization component 11e' composed of the calcite. The polarizer 11e', a quarter wave plate 3e", a polarizer 12e", a quarter wave plate 3e''', a polarizer 13e', and a quarter wave plate 3e'''' are based on the same beam 2-splitting method as that explained in FIG. 46. Thus, in the polarizers 11e', 12e', and 13e', the thickness of each calcite becomes thinner just as t, ½t, and ¼t. Also, the direction in which the beams are going to split is the y direction. Accordingly, the 64 spot lights are generated in the x direction by the 1st multi-spot lights-doubling prisms 11e, 12e, and 8 spot lights are generated in the y direction by the beam 2-splitting method using the calcite. Consequently, as illustrated in FIG. 48, 64×8 spot lights are generated in total.

Figure 49:
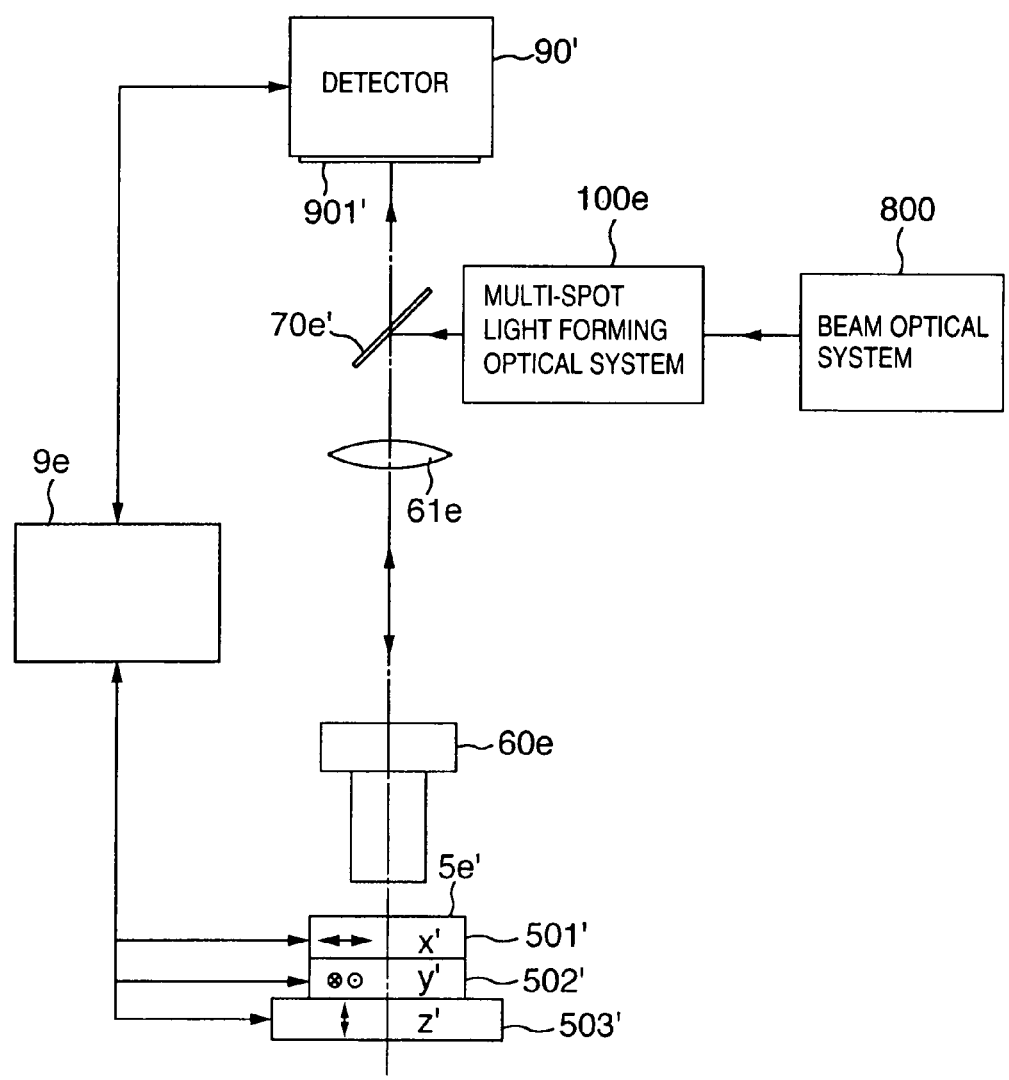
FIG. 49 is a front view for illustrating an embodiment of a confocal point detecting apparatus according to the present invention.

FIG. 49 indicates a confocal point detecting method using the above-described 64×8 multi-spot lights. In FIG. 49, the same reference numeral as that in the other drawings denotes the same component. The 8 beams emitted from a laser light-source and formed by an 8-beam optical system 800 are launched into the 64×8 multi-spot light-forming optical system 110e illustrated in FIG. 47. Then, in accordance with the above-described method, the 64×8 multi-spot lights illustrated in FIG. 48 are being emitted effectively from the mask surface 3e.

These multi-spot lights are reduced in size and are projected onto a surface of a target 5e' to be measured, using a half mirror 70e', the image-forming lens 61e, and the objective lens 60e. The projected multi-spot lights are reflected on the surface to be measured, and pass through the objective lens 60e, the image-forming lens 61e, and the half mirror 70e', then being image-formed onto a surface of a 64×8-pinhole mask 901' located directly in front of an image-pickup surface of a detector 90'. The lights having passed through the pinholes reach the image-pickup surface of the detector. If the surface of the to-be-measured target coincides with an image-forming plane of the projected multi-spot lights, the reflected light are image-formed on the pinholes of the pinhole mask, thereby making it possible to obtain the strong detected values. If the surface of the to-be-measured target does not coincide with the image-forming plane, out-of-focused spread lights reach the pinholes of the pinhole mask 901', and accordingly the intensities of the lights having passed through the pinholes become lower. Consequently, by executing the above-described detection with the to-be-measured target being displaced in an up-and-down direction by z-stage 503' shown in FIG. 49, it becomes possible to obtain the heights at the positions of the respective spots from their z direction values from which the detection maximum intensities at the respective positions can be obtained.

Figure 50:
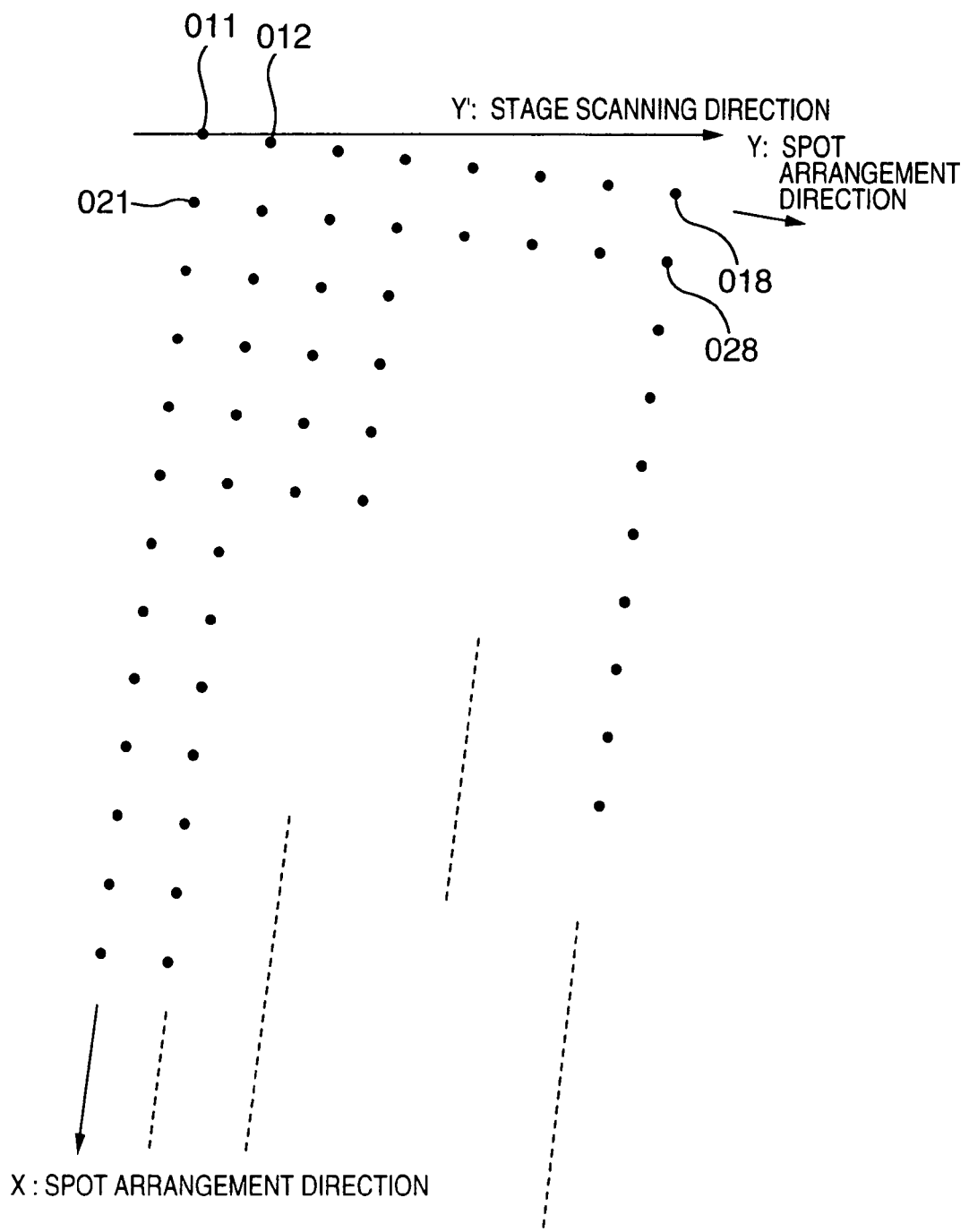
FIG. 50 is a diagram for indicating the relationship between the multi-spot lights and stage scanning in the confocal point detection according to the present invention.

In the above-explained confocal point detecting method in FIG. 49, when the target to be measured is fixed in the x, y directions, if, for example, the spot diameter is 1 μm and the spot spacing is 8 μm on the surface to be measured, only information about the 64×8 points with a 8 μm spacing can be obtained. Accordingly, it is required to detect the confocal point images at the other positions in sequence by displacing xy stage 501', 502'. FIG. 50 is an embodiment-illustrating diagram in the present invention, where there is indicated a method of obtaining the 2-dimensional confocal point images. The driving directions x', y' of the xy stage in FIG. 49 and the arrangement directions of the multi-spot lights to be projected onto the to-be-measured target are shifted slightly to each other as illustrated in FIG. 50. In the case of the 64×8 multi-spot lights, an angle θ formed between these two directions is set so that tan θ becomes equal to ⅛. On account of this shifting, scanning the stage in the y' direction results in irradiating empty positions between a spot 011 and a spot 021 with 7 spots, i.e., 012, 013, . . . , 018. This means that the entire surface scanning is performed all over the 1 μm spots with a 1 μm spacing placed therebetween.

The use of the above-described method irradiates the to-be-measured target with the multi-spot lights having high light intensities, and accordingly it becomes possible to detect the 64×8 spot positions in a short time. Thus, one scanning toward the samples is performed in the y' direction at a high-speed by the y stage and after the scanning, the stage is displaced slightly in the z direction, and the scanning is performed again. This operation is repeated, thereby detecting confocal point signals at the respective heights in sequence at a high-speed. In this way, a height at which the intensity is a maximum at each point is determined from the 2-dimensional intensity data at each point obtained at each height z. This makes it possible to execute the height measurement by the high-speed confocal point detecting method. Incidentally, setting the width of the above-described scanning to be equal to k times the pitch p of the multi-spot lights results in obtaining the 2-dimensional height information where the pixel number in the x direction is equal to 64×8=512 and the pixel number in the y direction is equal to 8 k.

Next, the explanation will be given below concerning another embodiment for forming the multi spots.

Here, taking the DNA probe array as an example, the explanation will be given concerning an apparatus and a method for measuring an intensity distribution of the fluorescent lights. The fluorescent lights are emitted from the fluorescent markers for marking the target DNAs trapped in the state of being hybridized with the DNA probes fixed onto the large number of microscopic reaction areas on the DNA probe array. Additionally, it is needless to say that the present invention is not limited to the inspection of the DNA, but is similarly applicable to the inspection and analysis of the other living body samples such as a fluorescent material-marked RNA, oligonucleotide and protein.

The DNA probe array to be detected is formed in the following way, for example: First, a washed glass substrate (such as a slide glass) is treated using a silane coupling agent (aminopropyltriethoxysilane), thereby introducing an amino group onto the surface. Next, an aldehede group-introduced oligonucleotide is dropped on microscopic areas so as to be reacted, thereby fixing the oligonucleotide on the glass substrate. A fluorescent marker-attached DNA is prepared independently as a specimen, i.e., a target to be inspected. Then, the fluorescent marker-attached DNA is spotted onto the oligonucleotide-fixed areas on the substrate so as to be trapped on the substrate by being hybridized therewith, thereby preparing the array to be measured. Incidentally, in order to fix the oligonucleotide on the glass substrate, the following methods are allowable: The surface treatment of the slide glass is performed using poly positive ions such as polylysine, thereby causing the electrostatic bond with electric charges of the DNA. Besides, the oligonucleotide is synthesized directly on the glass substrate, using a photolithography technique and a solid phase synthesizing technique. Being not limited to the above-described forming method, the DNA probe array can be formed by various well-known methods, and is measurable in much the same way.

Figure 51:
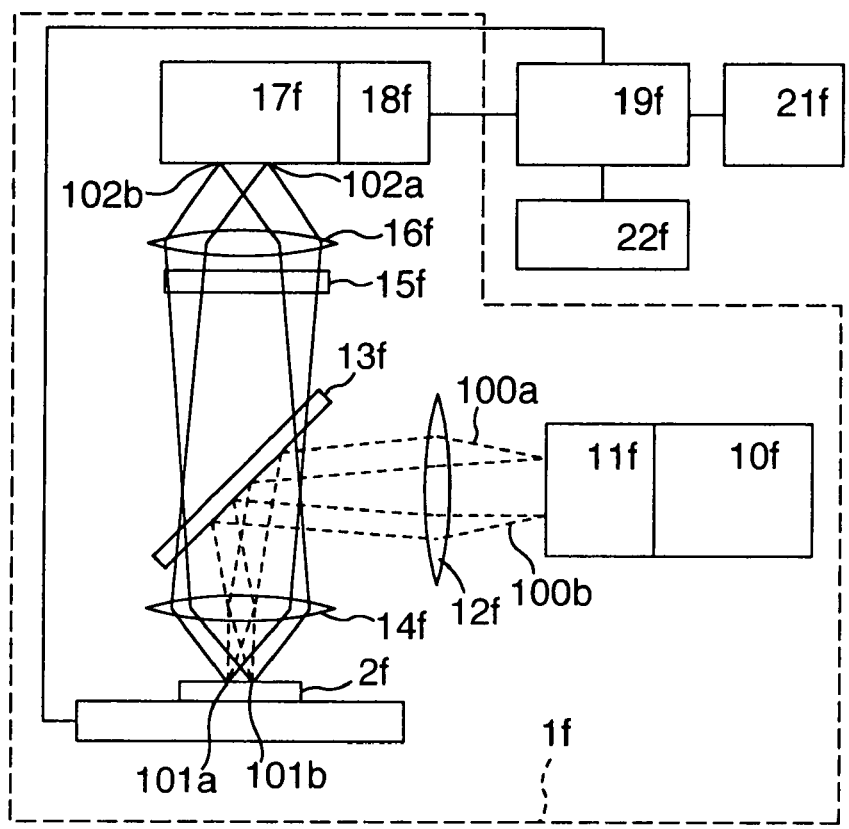
FIG. 51 is a schematic diagram for illustrating the entire configuration of one embodiment of a fluorescent marker distribution measuring apparatus according to the present invention.

FIG. 51 is a schematic diagram for illustrating the entire configuration of one embodiment of a fluorescent marker distribution measuring apparatus (DNA probe array measuring apparatus) according to the present invention. The apparatus includes a main body if of the DNA probe array measuring apparatus, a data processing/controlling unit 19f, and a monitor 21f. A substrate (DNA probe array) 2f is fixed on a XYZ driving unit 20f. A light from a light-source 10f of laser or the like is caused to pass through a multi light-source distribution unit 11f, thereby being emitted as a plurality of lights (100a, 100b, . . . ) that are located on straight lines equally and uniformly. These lights are collimated by a lens 12f, and are reflected downward by a dichroic mirror 13f, and are converged by an objective lens 14f, finally forming excitation spots (101a, 101b, . . . ) onto the substrate 2f. In the drawing, although only 2 of the lights and 2 of the excitation spots are illustrated for concern with the paper space, 64 excitation spots are formed actually. The larger the number of the excitation spots is made, just like 16, 32, 64, . . . , the more effective it becomes to implement the high-speed and high-sensitivity characteristics. Namely, if the total detecting time is the same, the larger the number of the spots becomes, the more likely it is to be able to lengthen the irradiating time per excitation spot and to be able to enhance the sensitivity. Also, if the irradiating time per excitation spot is the same, the larger the number of the spots becomes, the more likely it is to be able to shorten the total detecting time. In this case, 64 times speeding-up becomes executable.

Emitted lights (fluorescent lights, scattered light, reflected lights) generated from the excitation spots on the substrate 2f are converged again by the objective lens 14f, and are caused to pass through the dichroic mirror 13f (a 2-color property mirror for causing wavelength components of the excitation lights to be reflected and permitting longer wavelength components of the fluorescent lights to pass through), thereby extracting the fluorescent light components. Moreover, the fluorescent light wavelength components pass through an interference filter 15f deigned to permit the fluorescent light wavelength components to pass through. In addition, the fluorescent light components are converged by a lens 16f, thereby causing images of the excitation spots (101a, 101b, . . . ) to be image-formed as fluorescent light images (102a, 102b, . . . ).

A multi-detection unit 17f substantially simultaneously detects fluorescent light intensities generated from the plurality of excitation spots. Light signals from the multi-detection unit 17f are converted into numerical values by an A/D conversion unit 18f in harmony with a timing from the data processing/controlling unit 19f, then undergoing the processing such as various arithmetic operations by the data processing/controlling unit 19f. Also, the data processing/controlling unit 19f controls displacement of the XYZ driving unit 20f, and constructs a 2-dimensional distribution of the fluorescent light intensities on the substrate 2f in combination with the XY driving information, then displaying the 2-dimensional distribution on the monitor 21f. This makes it possible to detect the fluorescent light intensity distribution on a predetermined area surface of the substrate 2f, the total fluorescent light intensities of the plurality of microscopic areas provided on the substrate 2f, and so on. Accordingly, it becomes possible to calculate a quantity of the specimen DNAs coupled with the fixed oligonucleotide.

Here, on the surface of the substrate 2f, the excitation spots are set to be 2 μm in diameter and the spacing between the excitation spots is set to be about 20 μm. It is desirable to make an adjustment so that the size of the excitation spots becomes equal to 1/an integer-th of the spacing between the excitation spots. In the case of forming the 64 excitation spots, the spacing between both ends of all the spots becomes equal to 1.26 mm. Taking this into consideration, as the objective lens, the one satisfying the following conditions has been manufactured and used: The field-of-view 1.3 mm, the numerical aperture NA=0.70 (in order to enhance a fluorescent convergence efficiency), and (taking into consideration the case where the irradiation is performed from the back surface of the glass) a distance between the lens tip and the sample position 1.3 mm.

Figure 65:
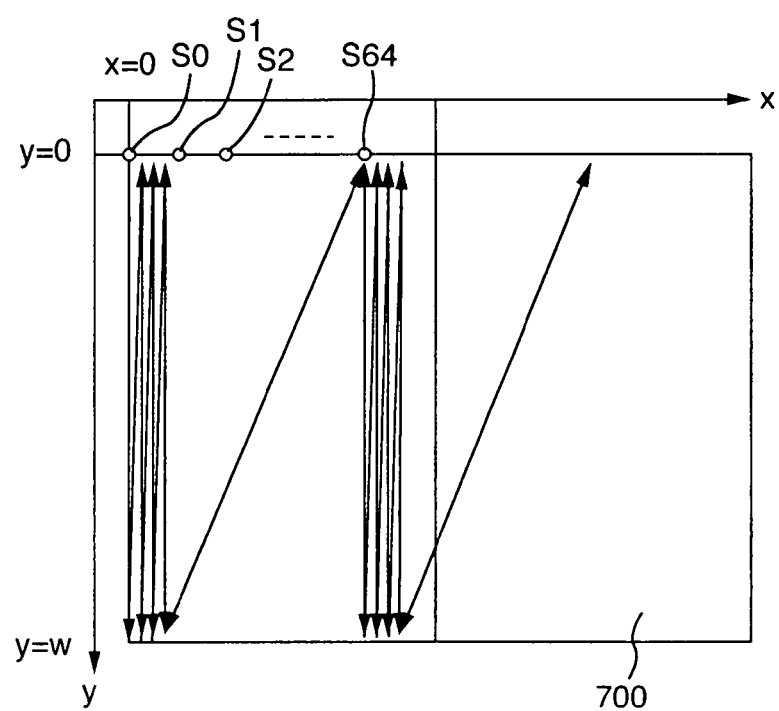
FIG. 65 is an explanatory diagram for explaining an example of the displacement of an XYZ driving unit 20*f*.

In order to measure the fluorescent lights all over the entire surface of an attention-paid area of the substrate 2f, the XYZ driving unit 20f is displaced in the following way: FIG. 65 is an explanatory diagram for explaining an example of the displacement of the XYZ driving unit 20f. The arrangement direction of the excitation spots is taken as an x axis. As illustrated in the drawing, the excitation spots S0, S1, S2, . . . , S63 are located in their initial positions in such a manner that the position of the excitation spot S0 becomes (0, 0), i.e., (x, y)=(0, 0). An area 700 is the attention-paid area to be measured which includes the oligonucleotide-fixed areas on the DNA probe array. In order to scan the entire surface of the area 700, the stage is displaced in a 2-dimensional manner. In the drawing, an arrow illustrates an orbit along which the excitation spot S0 is moved relatively to the area 700.

First, all the width of the area 700 is scanned in the y direction. Then, the y positions are returned back to 0, and the spots are shifted by the amount of the excitation spot diameter (in the present example, 2 μm) in the x direction. All the width of the area 700 is scanned again. This operation is repeated a plurality of times by the time the excitation spot S0 reaches the first position of S1. In the drawing, for simplicity, the scale-reduced illustration is given in such a scale that the spacing between the excitation spots is equivalent to 8 μm, and there is illustrated a manner where the positions in the x direction are changed 4 times so as to scan all the width in the y direction. Incidentally, in the case where the excitation spots are equal to 2 μm in diameter and the spacing between the excitation spots is equal to 20 μm, it turns out that the above-described operation has been repeated 1 times. This makes it possible to detect the entire surface of the area the width of which is x=0 to 1280 μm. The next operation is as follows: The y positions are returned back to 0 and the spots are shifted by 1260 μm in the x direction, thereby displacing the spots to an area that is adjacent to the area where the scanning has been finished using the 64 excitation spots. Namely, the spot S0 is displaced to the position corresponding to S64, and the above-described operation is repeated. This is repeated, thereby scanning the entire surface of the area 700.

Figure 66A:
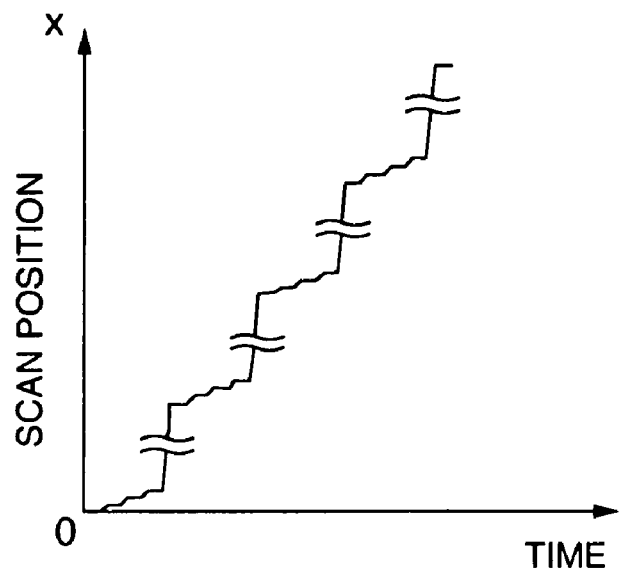
FIGS. 66A, 66B are diagrams for illustrating displacement curves of x, y axes of the XYZ driving unit 20*f*.
Figure 66B:
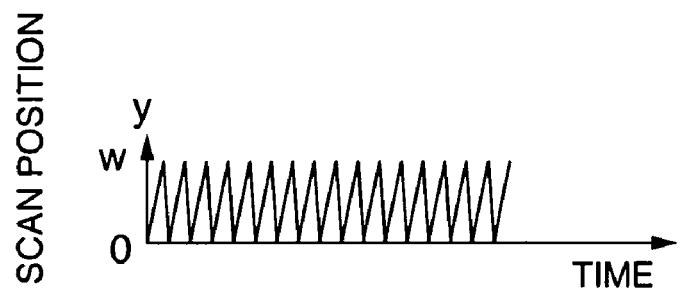

FIGS. 66A, 66B are diagrams for illustrating displacement curves of x, y axes of the XYZ driving unit 20f. FIG. 66A illustrates a displacement state of the XYZ driving unit in the x direction, and FIG. 66B illustrates a displacement state of the XYZ driving unit in the y direction. As is illustrated in the drawing, the operation of the present driving unit is characterized by repeating at least 2 types of displacement patterns in the x direction, i.e., the arrangement direction of the excitation spots, thereby scanning the entire surface of the to-be-measured area. Here, the 2 types of displacement patterns are step-like displacements with a microscopic width of 2 μm at n times (in the present example, 1 times) and a subsequent step-like displacement with a longer width at one time. This characteristic results from the existence of a limit to the objective lens' field-of-view size and the existence of a restriction to the spacing between the plurality of excitation spots. If the spacing between the excitation spots is made equal to a width obtained by substantially equally dividing the entire surface of the to-be-measured area by 64, it becomes unnecessary to employ the displacement method as described above. Namely, in the x direction, it is all right to repeat the step-like displacements with the microscopic width of the excitation spot diameter. In this case, however, the spacing between the excitation spots at both ends gets large, becoming substantially equal to a width of the entire surface of the to-be-measured area. This width exceeds the field-of-view width of a common objective lens (i.e., an objective lens being able to form the excitation spots of about 2 μm), thereby making it difficult to execute the measurement. If there should exist an objective lens having a sufficiently large field-of-view, the numerical aperture will become smaller or such an objective lens will be an extremely expensive one, either of which is unrealistic. Namely, the scanning method illustrated in FIGS. 65, 66A, and 66B is a method suitable for scanning the entire surface of the to-be-measured area with the use of the plurality of excitation spots.

Also, as timings of the data collection at the time of the scanning, there exist 2 timings, i.e., the timing at the time of the displacement in the x direction and the timing at the time of the displacement in the y direction. In principle, either of the timings makes it possible to obtain the information on the entire surface. However, it is advantageous to collect the data in harmony with the displacement in the y direction in particular. This is due to the following reasons: A stroke of the displacement at one time is longer in the y direction, and accordingly the connection with the adjacent pixel is more clear, and thus it is easy and secure to reconstruct an image from the measured data.

Next, the explanation will be given below concerning the configuration of the multi light-source distribution unit 11*f*. When the size of the excitation spots is 2 μm in diameter and the spacing between the excitation spots is 20 μm, at a light-emitting end of the multi light-source distribution unit 11*f*, the following is required: Assuming that a coupled magnification including the objective lens is 20 times, the lights need to be emitted from 64 portions under the condition that, at the light-emitting end, the size of the light spots is 40 μm in diameter and the spacing between the excitation spots is 400 μm. Since it is usually impossible to arrange the light-sources with the spacing of 400 μm, the following configurations have been constructed in the present invention. These configurations will be explained below, using FIGS. 52 to 57, and FIGS. 67 to 69.

Figure 52:
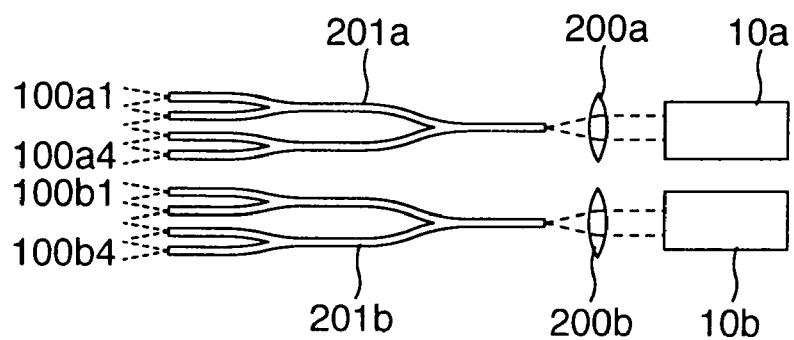
FIG. 52 is a diagram for illustrating the configuration of an embodiment of a multi light-source distribution unit according to the present invention.

FIG. 52 is a diagram for illustrating the configuration of an embodiment of a multi light-source distribution unit 11*f* for splitting lights emitted from n laser light-sources (2 of them are illustrated in the drawing) into 4n lights. Lights emitted from laser light-sources (10*a*, 10*b*) are each converged by lenses (200*a*, 200*b*), thereby being introduced into optical fibers (201*a*, 201*b*). Each optical fiber has 2 branching portions halfway, by which each of the converged lights is split into 4 lights. Accordingly, the excitation lights can be split just like 100*a*1, 100*a*2, ... 100*b*4. Incidentally, as the branching portion, it is possible to select not only the 2-branching type as illustrated in the drawing but also the other various types such as a 4-branching type. Also, in such a branching, there is employed a fiber that allows a light to be split equally. For example, light-emitting ends of optical fibers the core diameter of which is equal to about 40 μm are arranged with the spacing of 400 μm on a straight line, then projecting the lights in a ½th scale-reduced state. This makes it possible to implement the configuration in the present embodiment.

Figure 53:
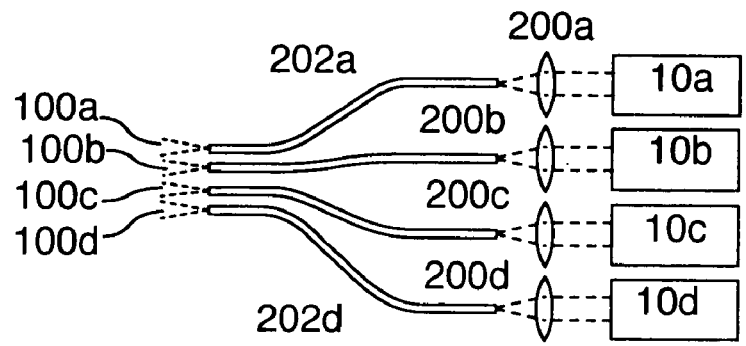
FIG. 53 is a diagram for illustrating the configuration of another embodiment of the multi light-source distribution unit according to the present invention.

FIG. 53 is a diagram for illustrating the configuration of another embodiment of the multi light-source distribution unit 11*f* for simply arranging lights emitted from m laser light-sources (4 of them are illustrated in the drawing) with the spacing of 400 μm on a straight line. The case m=4 is illustrated in the drawing. Lights emitted from the laser light-sources (10*a*, 10*b*, 10*c*, 10*d*) are each converged by lenses (200*a*, 200*b*, 200*c*, 200*d*), thereby being introduced into optical fibers (202*a*, 202*b*, 202*c*, 202*d*). Light-emitting ends of the optical fibers are arranged with the spacing of 400 μm on a straight line. This makes it possible to implement the configuration in the present embodiment concerning the lights (100*a*, 100*b*, 100*c*, 100*d*) regardless of the size of the laser light-sources with the spacing of 400 μm.

Figure 54:
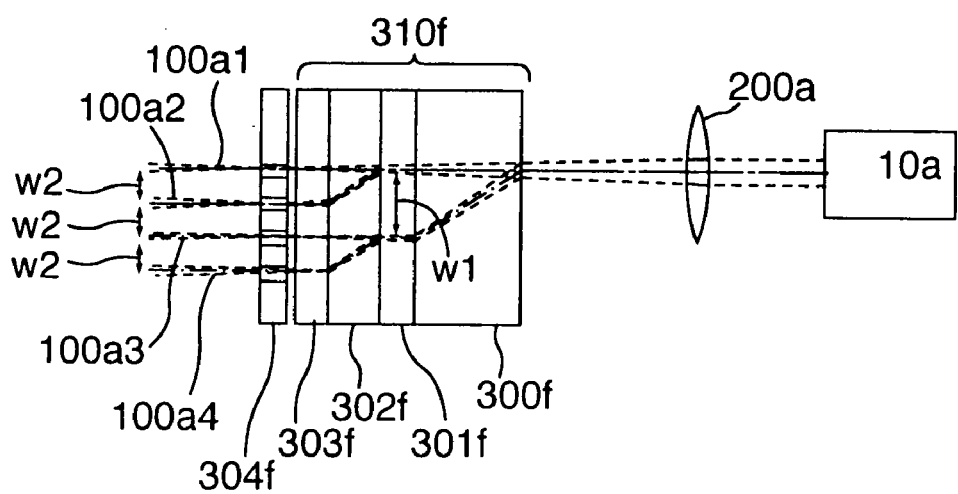
FIG. 54 is a diagram for illustrating the configuration of another embodiment of the multi light-source distribution unit according to the present invention.

FIG. 54 is a diagram for illustrating the configuration of another embodiment of the multi light-source distribution unit 11*f* utilizing the birefringent material (for example, calcite, and the other materials are also usable). As illustrated in the drawing, birefringent materials 300*f*, 302*f* such as calcite and quarter wave plates 301*f*, 303*f* are combined with each other in a sequence of, from the laser light-source side, the birefringent material 300*f*, the quarter wave plate 301*f*, the quarter wave plate 302*f*, and the quarter wave plate 303*f*, thereby forming a splitting component 310*f*. A laser light emitted from a laser light-source 10*a* is launched into the above-described component through a lens 200*a*. At this time, the polarization surface of the laser light has been inclined by 45 degrees, or the laser light has been converted into a circularly polarized light by being caused to pass through a quarter wave plate on the way. The laser light launched into the birefringent material 300*f* is double-refracted, thereby being separated into an ordinary ray and an extraordinary ray. A length of the birefringent material 300*f* is adjusted so that the two rays are away from each other by a distance w1. These lights are converted into circularly polarized lights by being caused to pass through the quarter wave plate 301*f* further, then being launched into the birefringent material 302*f*. Each of the 2 lights into which the light has been split is further split into 2 lights similarly. A length of the birefringent material 302*f* is adjusted so that the distance between the 2 lights becomes equal to w2. Making the adjustment so that w1 becomes 2 times as long as w2 allows the laser light to be split with an equal spacing. Incidentally, in order to let w2=400 μm, it is all right to set the lengths (in the optical axis direction) of the birefringent materials 300*f* and 302*f* to be about 8 mm and about 4 mm, respectively (in the case where the birefringent materials are calcite and the crystalline axes form 45 degrees toward the optical axes). Additionally, the lengths of the respective birefringent materials are varied, depending on the kind of the materials, the wavelength, and inclinations of the crystalline axes. When the directions of the crystalline axes are identical to each other, as described earlier, the length of the birefringent material is set to be ½th of that of the birefringent material at the preceding stage.

This configuration allows the 1 laser light to be split into the 4 laser lights equally and with substantially the same intensity, and permits the light-emitting ends to be located on a straight line. Thus, locating 16 laser lights with a spacing of 0.4×4=1.6 mm allows 64 light spots to be located with a spacing of 0.4 mm on a straight line. Incidentally, setting a focal point position of the lens 200*a* to be the position of pinholes 304*f* makes it possible to eliminate extra lights such as scattered lights. Accordingly, it becomes possible to make beautiful the configuration of the excitation spots on the substrate 2*f*, thereby permitting the resolution to be enhanced. Furthermore, the focal point position can be utilized as one focal point position for measuring the confocal point.

Also, although the splitting component 310*f* in the drawing has the configuration of executing the splitting with the 2 stages, it is also possible to employ 3 stages, 4 stages, and 6 stages. In these cases, it turns out that one laser light is split into 8, 16, and 64 lights, respectively, and the number of the laser lights required to obtain the 64 light spots can be made smaller like 8, 4, and 1. For example, in the case of a 6-stage configuration where there are employed the birefringent materials the respective lengths of which are 32, 16, 8, 4, 2, and 1 mm in sequence from the light-incoming side, it is possible to split the 1 laser light into 64 lights with a spacing of 0.1 mm.

Figure 55:
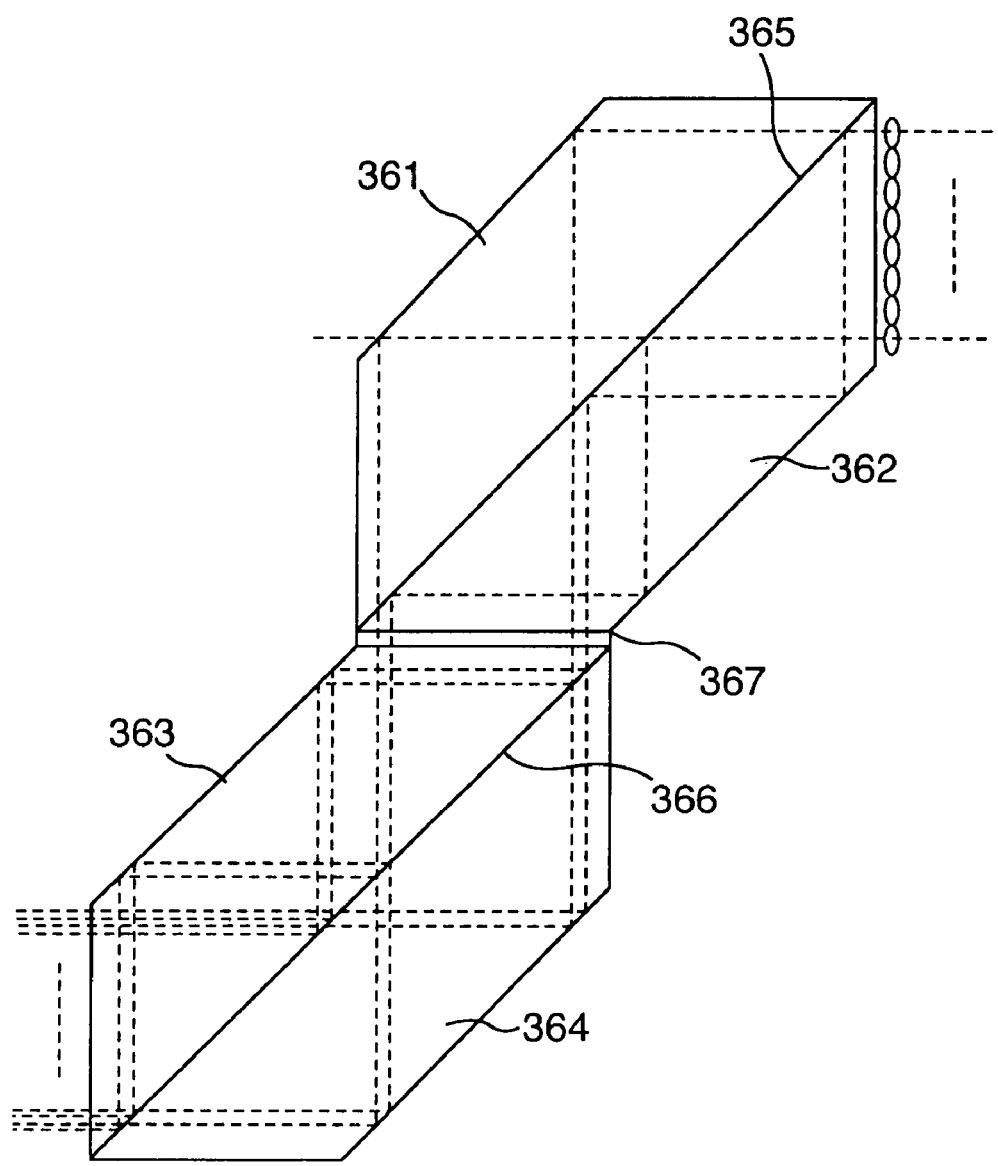
FIG. 55 is a diagram for illustrating the configuration of another embodiment of the multi light-source distribution unit according to the present invention.

FIG. 55 is a diagram for illustrating the configuration of another embodiment of the multi light-source distribution unit 11f. The components mainly includes 4 trapezoid-shaped glass prisms 361, 362, 363, and 364 and a quarter wave plate 367. The glass prisms 361, 362, 363, and 364 are connected to each other as illustrated in the drawing, and connected planes 365, 366 are polarization beam splitters. The respective glass prisms differ slightly in their dimensions. Thus, an incident light in a circularly polarized state is split into 2 lights on the connected plane 365, then becoming proximate to each other after the total reflection. At this time, making the optical path lengths differ from each other allows 2 parallel laser light-fluxes to be obtained. When causing the 2 lights to be launched into the components of the glass prisms 363, 364 again through the quarter wave plate 367, each of the 2 lights is further split into 2 lights by the same principle as that described above, which allows 4 light-fluxes to be formed in total. The adjustment of heights of the trapezoid-shaped glass prisms makes it possible to arbitrarily set a spacing between the light-fluxes, thereby making it easy to obtain the light-fluxes with the spacing of 0.4 mm, i.e., the light-fluxes that are exceedingly proximate to each other. In the drawing, there is illustrated the case where the number of emitted light-fluxes is 32 with reference to 8 incident light-fluxes. Incidentally, it is also allowable to locate a pinhole plate in proximity to the quarter wave plate 367.

Figure 56:
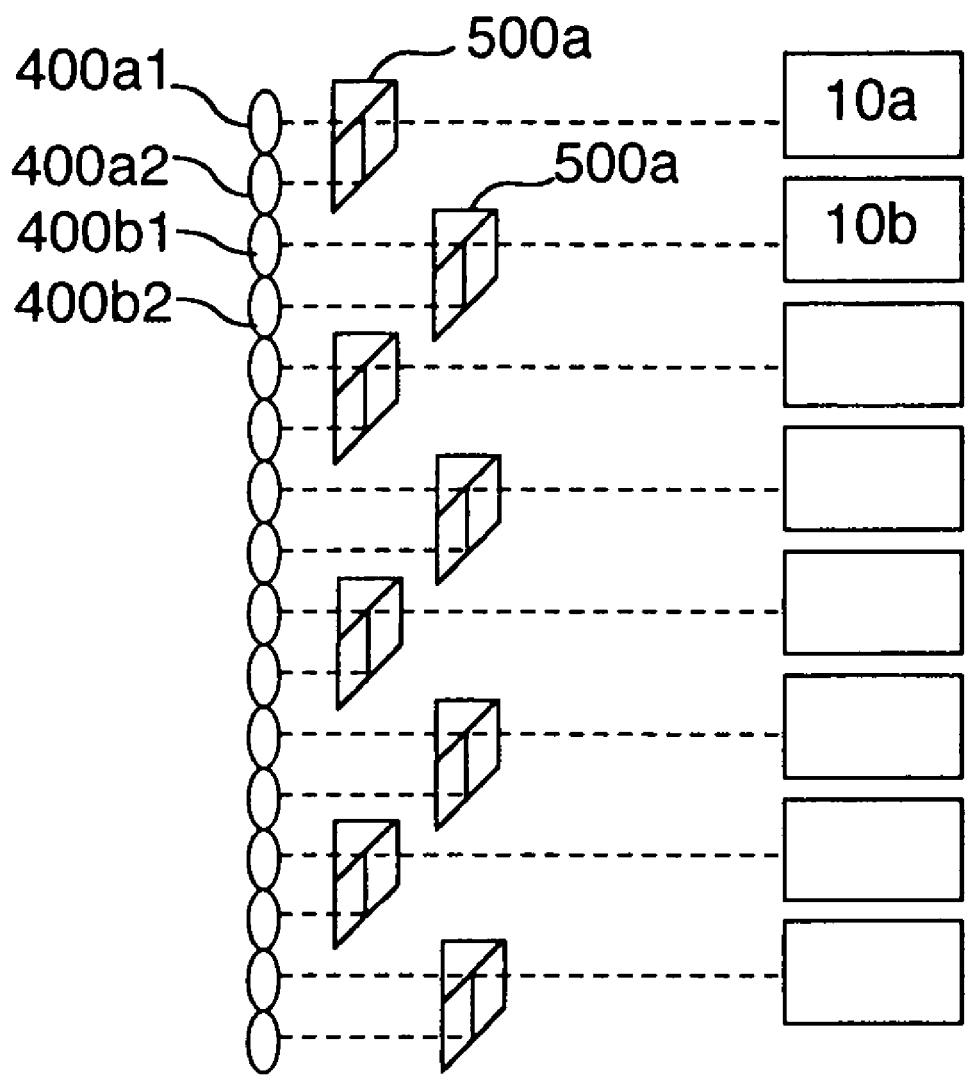
FIG. 56 is a diagram for illustrating the configuration of another embodiment of the multi light-source distribution unit according to the present invention.

FIG. 56 is a diagram for illustrating the configuration of another embodiment of the multi light-source distribution unit 11f. By using prisms 500a, 500b, . . . illustrated in the drawing which have a polarization beam splitter and a total reflection mirror, it becomes possible to split a beam into 2 beams. The use of the prisms by the number of 8 allows lights from 8 laser light-sources to be split into 16 lights. Incidentally, it is also allowable to employ, as a portion of the polarization beam splitter, a half mirror-shaped beam splitter where the transmittance=the reflectance (=an order of 50%).

Figure 57:
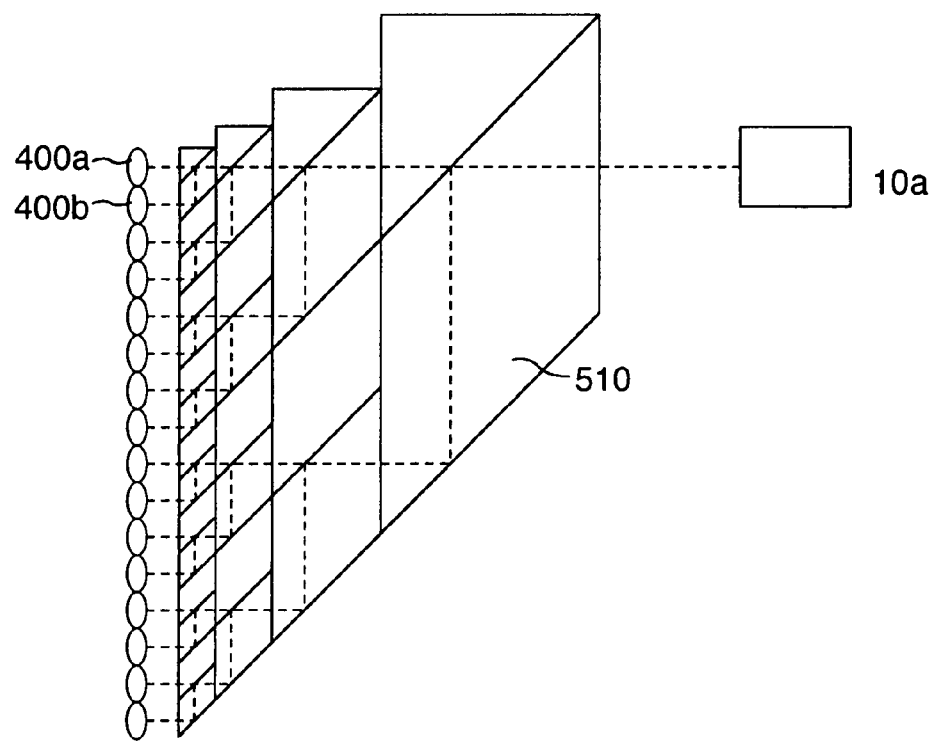
FIG. 57 is a diagram for illustrating the configuration of another embodiment of the multi light-source distribution unit according to the present invention.

FIG. 57 is a diagram for illustrating the configuration of another embodiment of the multi light-source distribution unit 11f. The prisms 500a, 500b, in FIG. 56 are arranged, and further thereon, there is used a prism 510 formed by accumulating larger-sized prisms in sequence. The half mirror-shaped beam splitters split a laser light. Repeating this at 4 stages allows 1 laser light to be split into 16 laser lights.

In the multi light-source distribution units of the configurations in FIGS. 56, 57, there exists a limit to a task of making the prism sizes smaller. Although the spacing between the laser lights to be split is allowable down to an order of 1 mm, it is getting gradually difficult to make the spacing even narrower. On account of this, in such a case, the combined use of the distribution units with the multi light-source distribution unit in FIG. 54 or FIG. 55 permits the laser lights to be split into the light-fluxes with a more microscopic spacing.

Figure 67:
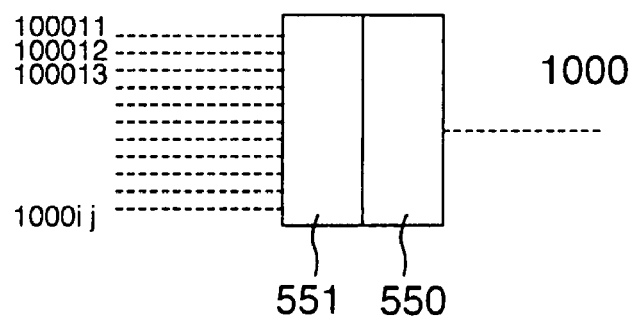
FIG. 67 is a diagram for illustrating the configuration of another embodiment of the multi light-source distribution unit according to the present invention.

In general, like the configuration of an embodiment of the multi light-source distribution unit illustrated in FIG. 67, a plurality of multi light-source distribution units 550, 551 are combined with each other. This makes it possible to construct another multi light-source distribution unit. Namely, the multi light-source distribution units in FIGS. 52 to 57 and what is more, multi light-source distribution units up to in FIGS. 68, 69 explained later are combined, thereby making it possible to construct another multi light-source distribution unit. Incidentally, the number of the laser light-sources is selected suitably in accordance with the number of the split-ting, the optical output of the laser light-source, and the light intensities of the excitation spots needed on the surface of the substrate 2f.

Figure 68:
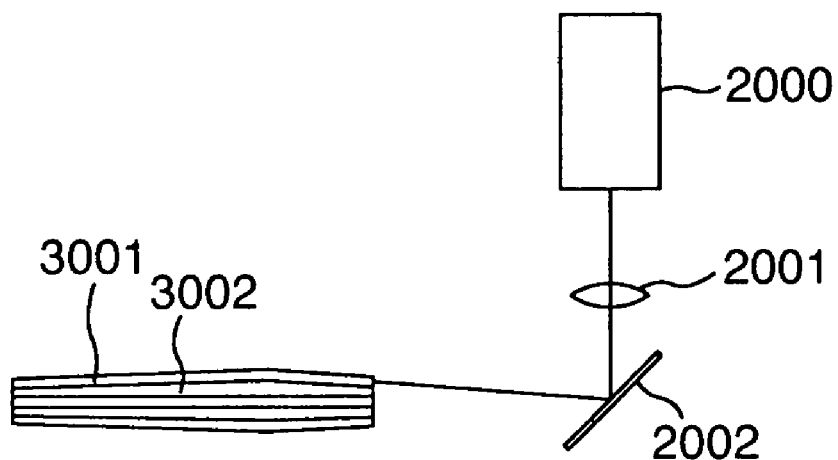
FIG. 68 is a diagram for illustrating the configuration of another embodiment of the multi light-source distribution unit according to the present invention.

FIG. 68 is a diagram for illustrating the configuration of another embodiment of the multi light-source distribution unit 11f. A laser light emitted from a laser light-source 2000 is caused to pass through a lens 2001, and is scanned by a beam scanning unit 2002 such as a galvanometer mirror and a polygon mirror, then being launched into end surfaces of optical fibers 3001, 3002, . . . the end surfaces of which are located at a focal point position of the lens 2001 in an arc-like configuration. The other end surfaces of the optical fibers 3001, 3002, . . . are located with a fixed spacing. This allows the laser lights to be split into a large number of light-fluxes, thereby making it possible to implement the configuration in the present embodiment.

Figure 69:
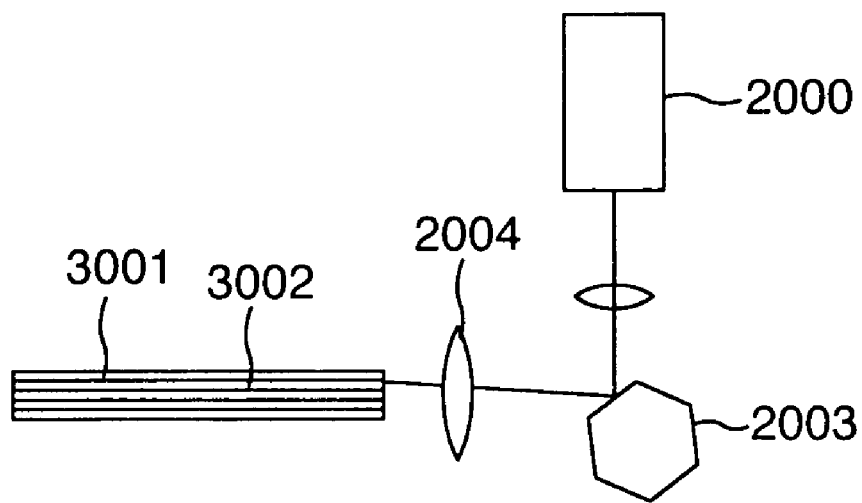
FIG. 69 is a diagram for illustrating the configuration of another embodiment of the multi light-source distribution unit according to the present invention.

FIG. 69 is a diagram for illustrating the configuration of another embodiment of the multi light-source distribution unit 11f. The laser light emitted from the laser light-source 2000 is scanned by a beam scanning unit 2003 such as the galvanometer mirror and the polygon mirror, and is caused to pass through a lens 2004, then being launched into the end surfaces of the optical fibers 3001, 3002, . . . that are arranged in a line. The respective split laser lights can be extracted from the other end surfaces of the optical fibers, which makes it possible to implement the configuration in the present embodiment.

Figure 58:
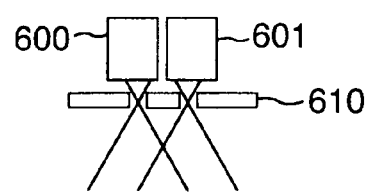
FIG. 58 is a diagram for illustrating the configuration of an embodiment of a multi-detection unit according to the present invention.
Figure 59:
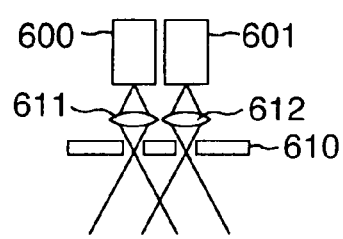
FIG. 59 is a diagram for illustrating the configuration of another embodiment of the multi-detection unit according to the present invention.
Figure 60:
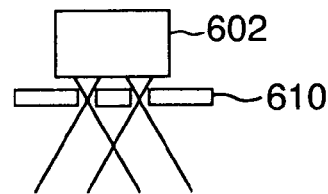
FIG. 60 is a diagram for illustrating the configuration of another embodiment of the multi-detection unit according to the present invention.
Figure 61:
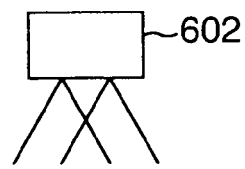
FIG. 61 is a diagram for illustrating the configuration of another embodiment of the multi-detection unit according to the present invention.
Figure 62:
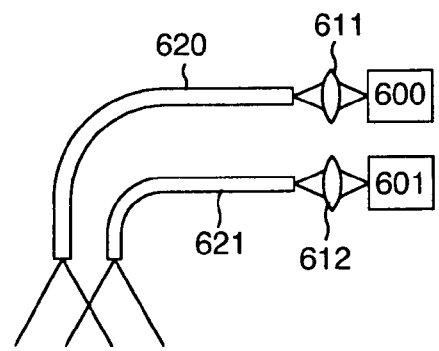
FIG. 62 is a diagram for illustrating the configuration of another embodiment of the multi-detection unit according to the present invention.
Figure 63:
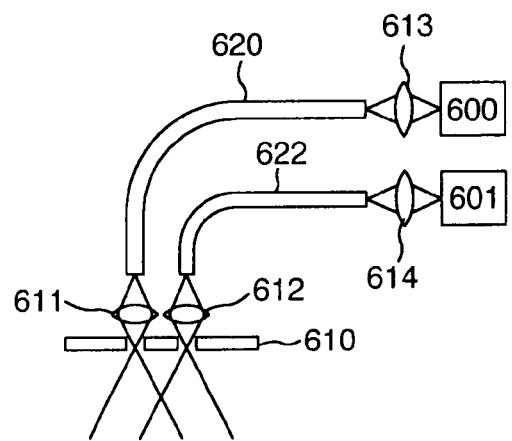
FIG. 63 is a diagram for illustrating the configuration of another embodiment of the multi-detection unit according to the present invention.

Next, referring to FIGS. 58 to 63, the explanation will be given below concerning the configurations of embodiments of the multi-detection unit 17f. Like the present example, images of the excitation spots, the size of which is 2 µm in diameter and between which the spacing is 20 µm, are image-formed with an appropriate magnification. A pitch of detectors determines the magnification. The detectors 600, 601, . . . , such as photomultiplier tubes and photo-diodes, are arranged in agreement with the image-formed positions (FIGS. 58, 59). Otherwise, the detection is executed using a censor 602 such as a photodiode line censor, a multi-anode type photomultiplier tube, and a CCD line censor (FIGS. 60, 61). In the case of the censor 602, a spacing between the individual detectors can be made narrower in comparison with the spacing in the methods in FIG. 58 and so on. For example, in the multi-anode type photomultiplier tube, the optical system is adjusted so that a spacing between the individual anodes is substantially equal to 1 mm and 50 times image-forming magnification is accomplished. Incidentally, through the use of pinholes 610 in FIGS. 58, 59, and 60, the multi-detection unit becomes a confocal point detecting system, thereby enhancing a position resolution and a depth resolution and improving the accuracy of the fluorescent light measurement. In the case of using the photodiode line censor and the CCD line censor, it is also allowable to cause the images to be image-formed at arbitrary positions and to detect signal intensities of the pixels at the image-formed positions. It is also possible to obtain the same effect as that of the pinholes by precluding signals from the pixels at portions other than the excitation light spots. It is also possible to execute the detection through optical fibers 620, 621 (FIGS. 62, 63).

Figure 64:
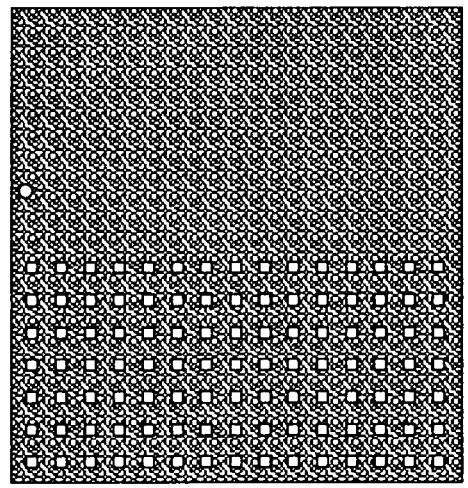
FIG. 64 is a diagram for illustrating an example of images detected.

FIG. 64 is a diagram for illustrating an example of the images detected using the present apparatus. The drawing illustrates the fluorescent light spot images captured on the slide glass. The spots coupled with the fluorescent marker-attached DNAs by the above-described method are formed on the slide glass. The size of the respective spots are about 200 µm, and the respective spots are formed on a lattice with a spacing of about 0.4 mm. The entire area over which the spots are formed is about 12 mm long and wide, and FIG. 64 indicates a portion thereof. In the drawing, the respective spots are increased in their specimen concentration in sequence from the above. As a result, the fluorescent light intensity has been detected in such a manner as to be increased in sequence from the above to the below.

Next, the explanation will be given below concerning the data detection and an image reconstruction (i.e., an operation of the data processing unit). In order to detect the signals over the area of 12 mm square in the unit of 2 μm, the area of 12 mm square is divided into 6000×6000 areas. Let these areas be represented by a reference notation: area (i, j), where i (=0–5999) denotes the positions in the x direction and j (=0–5999) denotes the positions in the y direction. The detection of the fluorescent light intensities based on the scanning by the irradiation spots is executed in the same way as was explained in FIG. 65. Explaining the scanning performed by the respective irradiation spots (S0, S1, . . . , S63), with respect to the scanning by the irradiation spot S0, area (0, 0) is first irradiated with the irradiation spot S0 and then, following the scanning in the y direction, the irradiation spot scans the areas from area (0, 1) to area (0, 5999). With respect to the scanning by the irradiation spot S1 as well, area (10, 0) is first irradiated with the irradiation spot S1 and then, following the scanning in the y direction, the irradiation spot scans the areas from area (10, 1) to area (10, 5999). The other irradiation spots S3 to S63 perform the scanning in much the same way. With respect to the scanning by the irradiation spot S63 as well, area (630, 0) is first irradiated with the irradiation spot S63 and then, following the scanning in the y direction, the irradiation spot scans the areas from area (630, 1) to area (630, 5999).

At that time, the signals from the optical detector corresponding to each spot are sampled every time each spot passes through the areas, then being A/D-converted. The signals are expressed as sig (k, j), where k corresponds to a position number (0-63) of the spots and j takes the values of 0 to 5999 at the positions in the y direction. Namely, the signals from the spot S1 are expressed as sig (1, j), j=0-5999. These signals are stored into image storing memories corresponding to the areas of area (i, j). Letting the image storing memories be represented by image (i, j) where i (=0-5999) and j (=0-5999) denote the positions in the x, y directions, respectively, the signals obtained by the above-described scanning at one time are stored into image(k×10+X,j)=sig(k,j)(X=0, k=0-63, j=0-5999). Incidentally, X denotes an X position of the spot S0 (In this case, X=0).

Then, as illustrated in FIG. 65, the Y position is returned back to 0, and the X position is displaced by the amount of +2 μm (X=1), then executing the detection in the same way. The signals obtained are stored into image(k×10+1,j)=sig(k,j) (k=0-63, j=0-5999). Repeating this operation ten times causes areas indicated by i=0-639, j=0-5999 in image (i, j) to be replaced by the measured signals.

Next, the X position is displaced by +1260 μm (a position of X=640), then, similarly, causing the above-described operation to be performed and storing the obtained signals into image(k×10+X,j)=sig(k,j)(X=640-649, k=0-63, j=0-5999). This operation causes areas indicated by i=640-1279, j=0-5999 in image (i, j) to be replaced by the measured signals. Moreover, the X position is displaced by +1260 μm (a position of X=1280), then repeating the above-described measurement. These are repeated, thereby displaying the X position up to a position of X=5760, and causing the scanning to be performed 1 times further. This measures all the areas indicated by i=0-6399, j=0-5999 in image (i, j) (Although this area is wider than area (i, j), it is all right to extract a needed area alone). This image (i, j) is then converted into a picture, which is displayed on the monitor or the like.

In the present embodiment, there are provided the excitation spots and the optical detecting unit corresponding to each spot. There occurs no problem if the intensities of all the excitation spots and a sensitivity characteristic of the optical detecting unit coincide with each other. If not, there appears a stripe-shaped pattern in the obtained picture. In such a case, there is a need of a mechanism for correcting the sensitivity characteristic for each spot. Thus, in FIG. 51, there is provided an intensity correction value storing unit 22f. In order to make the correction, data for the amendment is created first. Preparing a specimen having equal fluorescent light intensities (or locating light-sources that emit lights equally at the respective spot positions), the intensities at that time are measured for each spot. In addition, the intensities at the time when the lights are light-shielded are also measured for each spot. In this way, back (k), i.e., a background value on the per-spot measurement basis, and corr (k) are stored into the intensity correction value storing unit 22f. Here, corr (k)(k is the position number (0-63) of the spots) are the reciprocal values of the signal intensity values at the time when a light intensity becoming a reference value is detected (the signal intensity values obtained by subtracting the background value). By outputting signal values sig (k, j) corrected as $$sig(k,j)=(sig(k,j)-back(k))corr(k)$$

toward the measured signals sig (k, j), it becomes possible to correct a variation in the sensitivity among the spots.

In contrast to the circumstances that the ordinary apparatus uses only 1 fluorescent-light excitation irradiation spot, the present invention allows the substrate to be simultaneously irradiated with the plurality of (64, for example) fluorescent-light excitation irradiation spots. This condition results in the following effects:

When detecting the entire area in a fixed time-period, it is possible to lengthen the irradiating time per irradiation spot (64 times in the present embodiment). This enhances the fluorescent-light detecting sensitivity. Also, lengthening the irradiating time per irradiation spot also makes it possible to slow the displacement speed of the stage. This enhances the mechanical stability and durability as well. Also, equating the irradiating time per point makes it possible to shorten a time needed to measure the whole of a predetermined region on the substrate. This allows the high-speed characteristic to be implemented. In particular, when enhancing the detection resolution, namely, when making smaller the size of the irradiation spots on the substrate, if a target that has been measured conventionally with a resolution of, for example, 10 μm is measured with a resolution of 1 to 2 μm, it is required to measure in sequence the irradiation spot regions that are 100 to 25 times more in number. On the other hand, just like the present invention, by simultaneously irradiating the substrate with the plurality of (64) fluorescent-light excitation irradiation spots so as to execute the fluorescent light detection, it becomes possible to accomplish the high-resolution and high-speed characteristics.

Incidentally, when performing the irradiation with the split laser lights, the intensity of the individual split laser lights becomes weaker by the amount of being split. The use of a larger output laser apparatus, however, allows this problem to be solved easily.

According to the present invention, it becomes possible to measure the DNA probe array and so on with a high-resolution, at a high-speed, and with a high-sensitivity.

Figure 70:
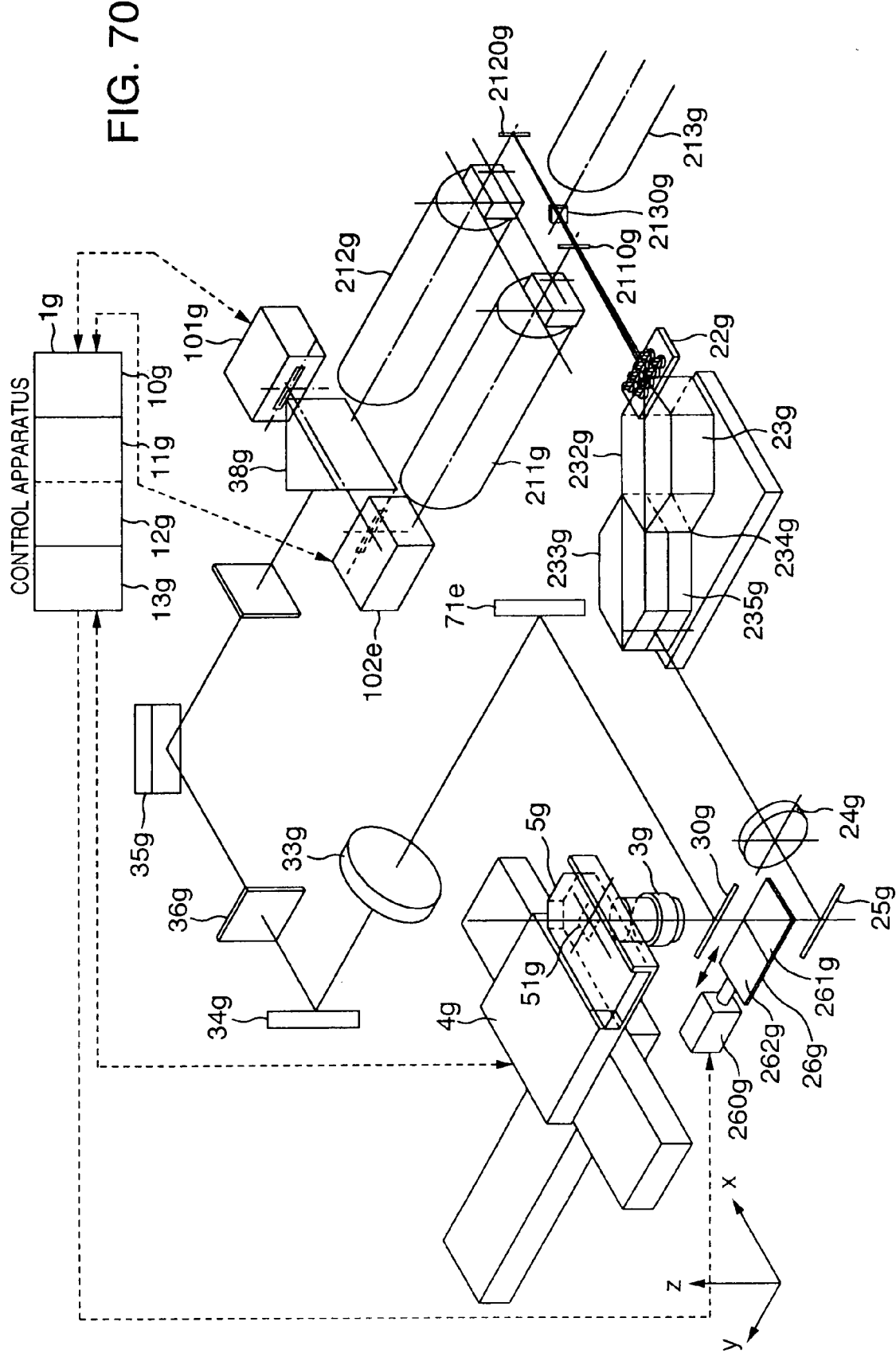
FIG. 70 is a perspective view for illustrating the schematic configuration of the DNA chip inspecting apparatus according to the present invention.

FIG. 70 is another embodiment-illustrating diagram in the present invention. Laser light-sources 211g, 212g, 213g . . .

emit parallel round beams that are converted from diffused lights emitted from semiconductor lasers having a wavelength of 635 nm. The K light beams emitted from the respective laser light-sources are launched into multi-beam splitters 22g with a pitch P. The multi-beam splitters 22g are arranged with a pitch P by the number of K, and split each of the incident beams into 2 beams, thereby forming 2K beams with a pitch P/2 and in parallel to each other. These beams have been formed into elliptically polarized lights, linearly polarized lights, or circularly polarized lights, the elliptically polarized lights having the longer axis in the directions that forms ±45 degrees toward y, z axes of the illustrated coordinate.

The 2K beams are arranged with the pitch P/2, then being launched into a multi lens 231g. The multi lens 231g is pasted on a prism 232g. The beams that have passed through the multi lens pass through the prism 232g, then being launched into multi pinholes positioned at the boundary with a prism 233g.

At both of the bases of the prisms 232g, 233g, trapezoid-shaped glasses that differ from each other slightly in thickness are bonded to each other. The bonded plane is formed as a polarization beam split plane. As a consequence, the beams having passed through the prism 232g are converged into the respective pinholes of a pinhole array 234g having the 4K pinholes with a pitch P/4. The pinhole array plays a role of eliminating a stray light so as to irradiate the DNA chip with the multi spots having a less noise, the stray light existing in a portion other than the pinhole unit and becoming the noise.

At the time of passing through the above-described prism 232g, the lights having passed through the polarization beam split plane become P-polarized lights (linearly polarized lights perpendicular to the z axis), and the lights reflected by the beam split plane become S-polarized lights (linearly polarized lights in the z axis). On account of this, the half of the lights having passed through the multi spots are the P-polarized lights, and the remaining half are the S-polarized lights.

Directly behind the pinhole array, there is located a half wave plate or a quarter wave plate. The half wave plate has an optical axis inclined at 22.5 degrees toward the above-described P-polarized and the S-polarized lights. Also, the quarter wave plate has an optical axis inclined at 45 degrees toward the lights. The P-polarized and the S-polarized lights that have passed through such a wavelength plate after passing through the pinholes become linearly polarized lights inclined at ±45 degrees toward the z axis in the case of the half wave plate, and become right-handed and left-handed circularly polarized lights in the case of the quarter wave plate.

The lights having passed through the above-described wave plate 235g are launched into the above-described trapezoid-pasted prism 233g (Additionally, the difference in thickness between the trapezoid-shaped prisms is one-half of the thickness of the above-described trapezoid-pasted prism 232g). The pasted plane, i.e., the trapezoid-shaped base of the prism, is formed as the polarization beam split plane. As a consequence, the 4K lights having passed through the pinhole array and the wavelength plate are increased by 2 times in number even further, eventually having a pitch of P/8 and becoming 8K in number. On account of this, the lights are emitted from the prism 233g as if 8K point light sources (secondary point light sources) existed at the position of the pinhole array 234g.

The lights from the 8K secondary point light sources formed in this way pass through a lens 24g, a mirror 25g, a light amount adjuster 26g, a wavelength selection beam splitter 30g, and a high NA objective lens 3g, then image-forming images of the 8K point light sources onto a detection plane 51g of a DNA chip 5g. Incidentally, the light amount adjuster 26g is provided in order to adjust a light amount of the fluorescent-light detection excitation lights depending on to what extent the fluorescent material exists on the detection plane 51g. Namely, if the concentration of the fluorescent material is high all over the entire DNA chip or fluorescent light detection sample, a driving source 260g is driven so that a ND filter 262g of, for example, 10% is inserted into the excitation light optical path. However, changing the intensities of all the excitation light beams in this way, in some cases, results in narrowing the dynamic range of the detection. Consequently, in such a case, it is possible to adjust the intensities of the individual excitation light multi spots using a light modulator array not illustrated.

Also, when it is required to execute the detection in a dynamic range of, for example, $^2N$, the following detecting method is also possible: Setting a ND filter 261g to be 100% (i.e., there exists no ND filter) and setting the ND filter 262g to be a transmittance of $100 \times 2^{N/2}$%, the ND filters are exchanged so as to execute a 2-picture detection toward the entire picture. Then, both of the detected pictures are superimposed, thereby detecting the fluorescent light images in the dynamic range of 2N. In this way, the detection of the 2 pictures necessitates a time twice as long as the time in the ordinary method. The present invention using the multi spots, however, makes it possible to execute the detection at a speed that is more than 5 times higher as compared with the speed in the conventional methods.

The 8K point light source images that have illuminated the detection plane of the DNA chip illuminate and excite a target DNA having the fluorescent material at a tip hybridized with a probe DNA.

Figure 71:
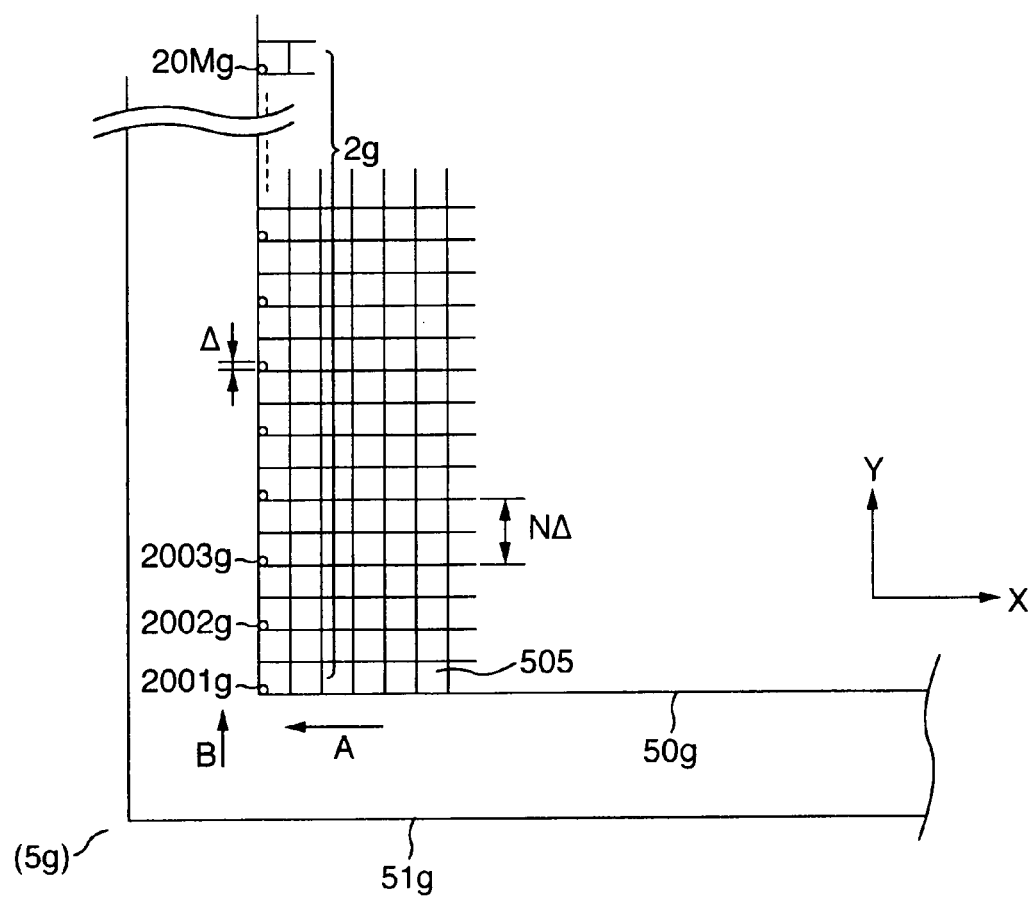
FIG. 71 is a plane view for indicating the relationship between cells of the DNA chip and the excitation lights.

FIG. 71 is a diagram for indicating the relationship between the multi spots and the details of an area 50g where the target DNA exists on the glass 51g of the DNA chip 5. A numeral 505 denotes a cell. The cells are arranged in the x, y directions with a fixed pitch. In each cell, a desired DNA fragment, which is also referred to as the probe DNA, is attached to the glass for each address in the arrangement of the cells. This probe DNA is a DNA that usually includes the same nucleotide sequence in each cell, and a different DNA is usually probed in a different cell. A sample solution of the target DNA obtained by attaching the fluorescent material to ends of plural types of DNA fragments formed by collecting, refining and amplifying a target to be inspected, i.e., a specimen of a creature, is poured onto the DNA chip prepared in the above-described manner, thereby causing the hybridization to occur. Namely, a target DNA corresponding to the nucleotide sequence of the probe DNA in each cell is coupled with the probe DNA, namely, is hybridized therewith. The DNA chip in FIG. 71 has been formed in the above-explained manner.

With reference to the cells 505, the multi spots 2001g, 2002g, 2003g, . . . , 20Mg, i.e., the pumping lights, are arranged with a pitch that is an integer multiple of the cell pitch. In the case of FIG. 71, this integer is equal to 2. The beam diameter of the multi spots is equal to substantially Δ, and the pitch between the multi spots is equal to NΔ. In the case of FIG. 71, N=10 and the detection is executed by dividing one cell into 5×5 pixels. An object of such a division is as follows: When a foreign substance or the like is attached in a cell, the foreign substance generates a strong fluorescent light, thereby causing an error in the detected data. Accordingly, judging that a fluorescent light exhibiting a detection intensity larger than the strong fluorescent light detection intensity is generated by the foreign substance, an average fluorescent light intensity within the cell is determined by excluding the pixels where the foreign substance has been attached.

Figure 72:
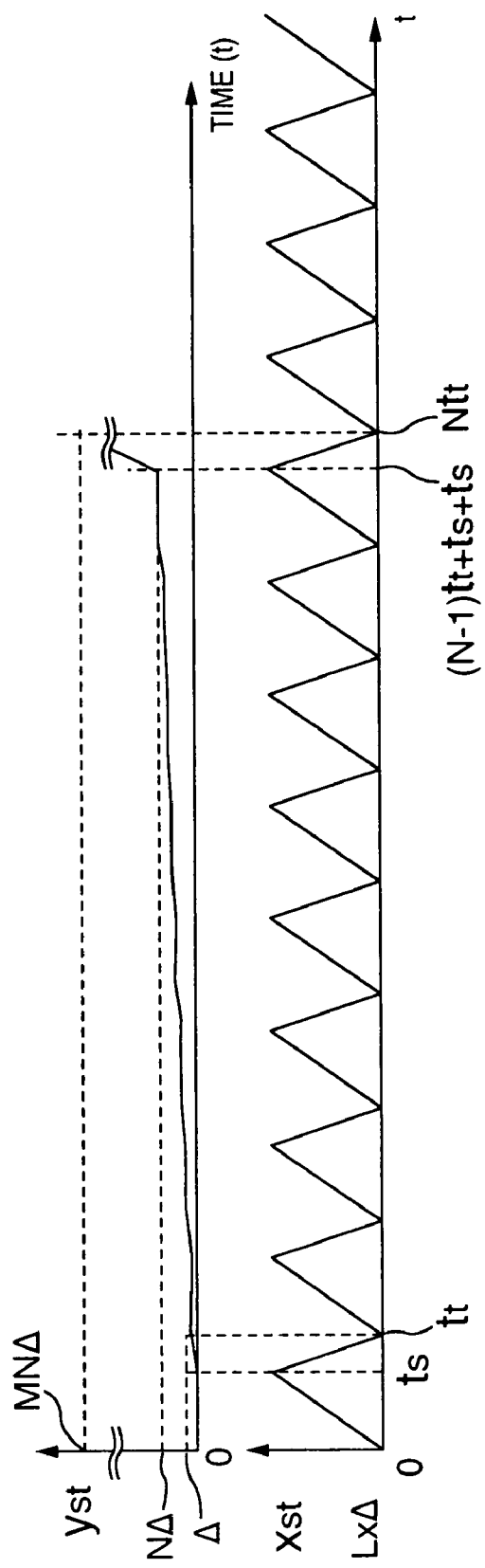
FIG. 72 is a diagram for explaining the scanning of the DNA chip in the x, y directions according to the present invention.

The DNA chip is scanned in the x direction as is indicated by A in FIG. 71, and when the multi spots scan the cells positioned at the right end, the multi spots are displaced by the amount of one pixel A in the y direction, and the scanning is executed in the x direction again. This is repeated, and when the scanning of N pixels (in the drawing, 10 pixels) is over, the multi spots are displaced by the amount of MNΔ in the y direction, and the above-described operation is repeated, thereby scanning all the cells. FIG. 72 is a diagram for illustrating the above-described operation. Letting the transverse axis represent time, the longitudinal axis in an upper graph indicates the displacement quantity of the y stage, and the longitudinal axis in a lower graph indicates the displacement quantity of the x stage. On the x stage, the scanning for the detection has been executed during a time $t_s$, and the x stage is returned back to the initial position during a time $t_r-t_s$. The detection has been executed in the forward-step path alone. When the accuracy of the stage is sufficiently high, the detection is executable in the backward-step path as well.

As illustrated in FIG. 70, the simultaneous detection of the fluorescent lights by the amount of the M pixels is executed in the following way: The fluorescent lights generated by the irradiation with the excitation multi-spot lights are received by the objective lens 3g. Out of the transmittance fluorescent lights having passed through the objective lens, the fluorescent lights at the wavelength in proximity to 670 nm are reflected by the wavelength selection beam splitter 30g. Then, the reflected fluorescent lights are guided into a detecting optical system. Namely, the reflected fluorescent lights pass through a mirror or a wavelength selection beam splitter, i.e., 32g, 34g, 35g, and 38g, and pass through an image-forming lens 33g, then being image-formed at light-receiving apertures of multi-channel photomultiplier tubes 101g, 102g. At the respective light-receiving apertures, there is provided a light-shielding plate where pinholes are bored, the diameter of the pinholes being substantially equal to that of the images of the excitation multi-spot lights. Only the fluorescent lights that have passed through the pinholes are detected, thereby executing the confocal point detection.

Figure 73:
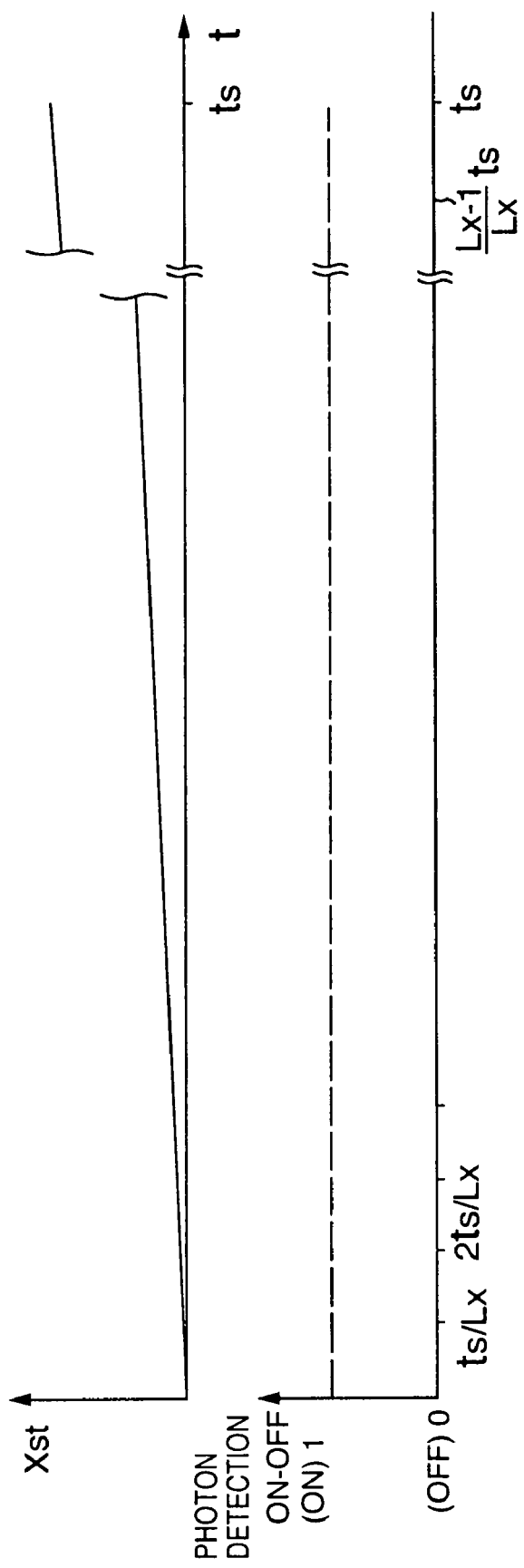
FIG. 73 is a diagram for indicating the relationship between the scanning of the DNA chip in the x direction and photon detection according to the present invention.

An upper graph in FIG. 73 is a graph obtained by enlarging the time axis of the lower graph in FIG. 72. In the drawing, the time $t_s$, which is needed to execute one scanning, is seen in more detail. In a lower graph in FIG. 73, although the transverse axis, i.e., the time axis, is identical to the transverse axis of the upper graph in FIG. 73, the longitudinal axis indicates a timing of a time of the photon counting performed by a weak light detector such as the photomultiplier tube. This graph means that the photon counting is performed during a time for which the signal level is 1 and the photon counting is not performed during a time for which the signal level is 0. During the one-sectioned time for which the signal level is 1, the signal by the amount of one pixel is detected. After the signal level becomes 0, when the signal level 1 starts next, the next pixel is detected. Since there exist $L_x$ pixels in one scanning in the x direction, the detecting time per pixel becomes equal to $t_s/L_x$ or less. The time needed to perform the photon counting on the per-pixel basis is required to correspond to the position of the cell in the DNA chip. Consequently, the signal for the starting time of the photon counting is created based on a signal from the length-measuring device for measuring the x stage's position.

If the finishing point-in-time of the per-pixel photon counting is determined in accordance with the information from the stage's position length-measuring device, when the stage is not displaced uniformly, the per-pixel photon counting time is varied for each pixel. This requires that the finishing time be a time that has elapsed by a fixed time after the starting time. For the purpose of this, pulses of a high-frequency (frequency vr) pulse generator is counted. The counting is started from the starting of the photon counting, and the photon counting is finished at the time when the pulse number counted reaches a fixed pulse number Nr. Namely, with reference to whatever pixel, the photon counting is executed during a time of Nr/vr. A control apparatus 1g in FIG. 70 is a system for controlling the above-described operation. A reference numeral 12g denotes a PC (personal computer), which performs the control of all the operations. A PC 13g generates a controlling and driving signal of the above-described stage 4g, and fetches the position information of the stage 4g from the length-measuring device.

Figure 74:
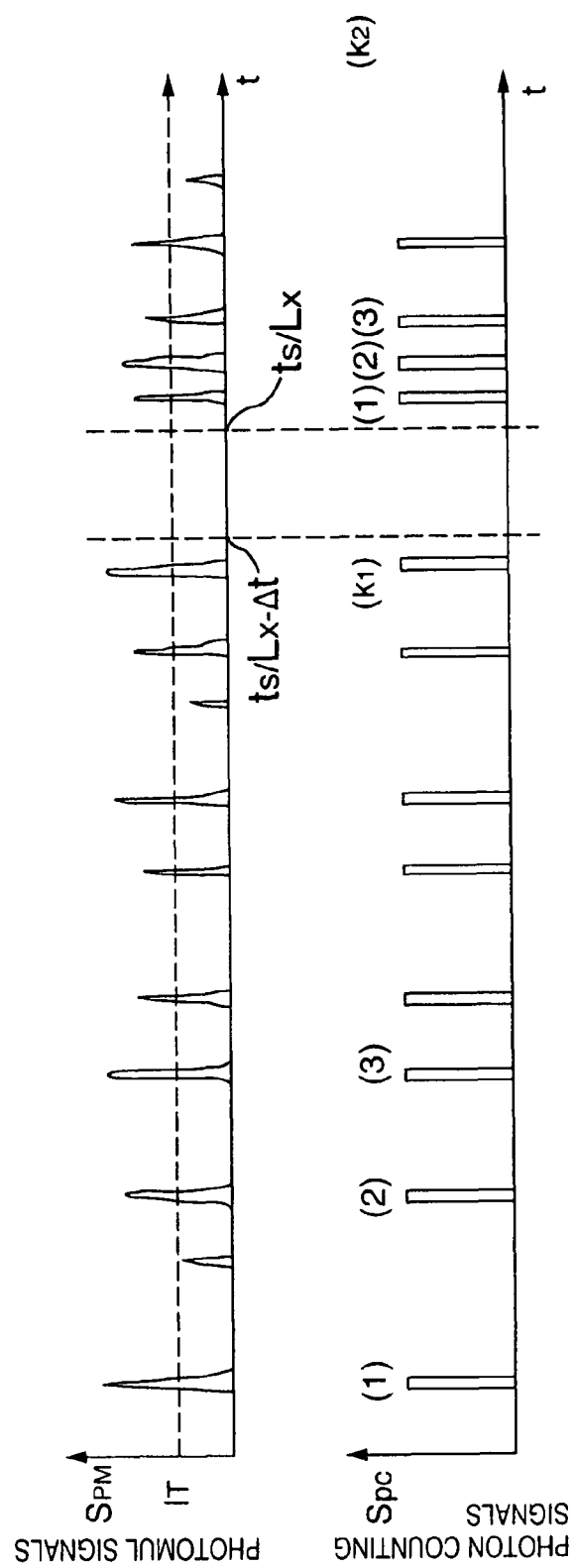
FIG. 74 is a diagram for illustrating photon counting signals of weak lights.

In the above-described manner, the fluorescent lights from the 64 pixels in the x direction are detected simultaneously and, through the scanning by the stage, in sequence. Photon counting signals $S_{PM}$ to be obtained from each pixel are detected in the manner as is illustrated in FIG. 74. Namely, focusing an attention on one photomultiplier tube out of the multi-channel photomultiplier tubes, in the case of weak detected fluorescent lights, photomul signals are obtained as photon detection pulse signals the pulse time-width of which is equal to about 30 ns with a low frequency as are illustrated in an upper graph in FIG. 74. Then, pulse signals with a fixed width are generated from the rising edges of the photomul signals. Otherwise, in the case where the photomul signals exceed a fixed signal level $I_T$ as are illustrated in the upper graph in FIG. 74, the photomul signals are converted by a comparator circuit into fixed level signals just like the signals $S_{PC}$ illustrated in a lower graph in FIG. 74. The pulse-shaped signals formed in this manner are counted using a counter. This allows the detected photon number to be determined within the detecting time $t_s/L_x-\Delta t=Nr/vr$.

FIGS. 75A to 75D illustrate the case where the detected fluorescent light intensities are high. The drawings illustrate the photomul detection signals $S_{PM}$ and the signals $S_{PC}$ after being compared. The photon pulses are detected with a high frequency and accordingly, in some places, 2 or more of the pulses have been detected in a state of being superimposed on each other. On account of this, among the signals after being compared, there appear signals having larger width. $S_{PC}'$ is a diagram resulting from enlarging a time of the signals $S_{PC}$ between a point-in-time A and a point-in-time B. If the detection signals have been detected in the state of being superimposed between a signal and a signal subsequent thereto, the pulse-widths of the signals after being compared are increased. As a result, calculating simply the pulse number of the signals after being compared results in an increase in the error. Accordingly, as illustrated in a graph in FIG. 75D, constant high-frequency pulse signals are counted with $S_{PC}'$ employed as the gate. The use of the counted signals $S_{PWC}$ thus obtained makes it possible to determine the photon number more precisely than counting the pulses of the $S_{PC}$ signals. Moreover, by correcting the counted value of the $S_{PWC}$ signals with a downward-convex univalent function $F(S_{PWC})$, it becomes possible to execute even more precise photon counting.

The above-described method, however, is insufficient to implement the even broader dynamic range requested in the DNA inspection. Namely, in the DNA inspection, the dynamic range of several photon pulses to one hundred and tens of thousands of photon pulses is requested within the time needed to detect one pixel. Nevertheless, since the width of the photon detection pulses is equal to tens of ns, when trying to implement the entire dynamic range by the photon counting, tens of ns×one hundred and tens of thousands=several m sec become required as the per-pixel detecting time.

Accordingly, even if the number of the multi-spot excitation lights is equal to 64, when the number of the pixels is 6000×6000, it turns out that it takes 30 minutes or so to execute the detection.

Figure 76:
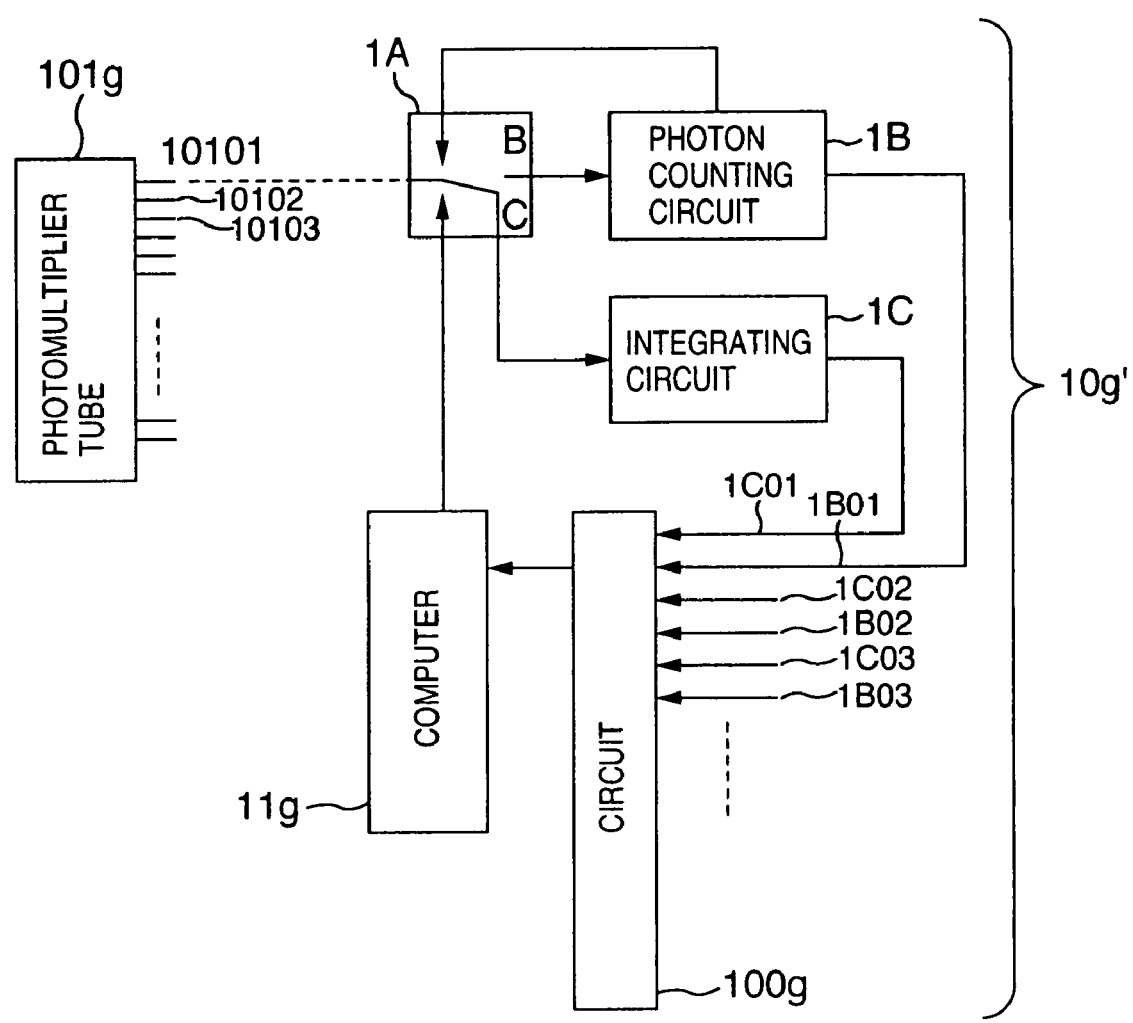
FIG. 76 is a block diagram for illustrating a circuit configuration for detecting a broad dynamic range according to the present invention.
Figure 77A:
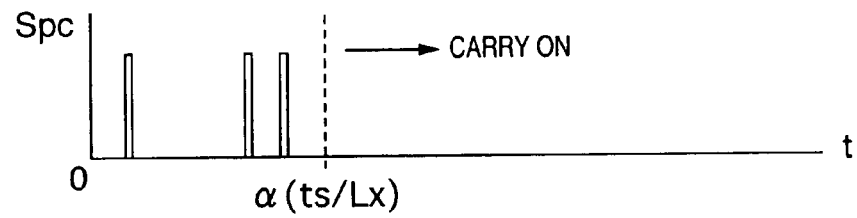
FIGS. 77A to 77E are diagrams for indicating a method of differentiating between the weak detected lights and the strong detected lights according to the present invention.
Figure 77B:
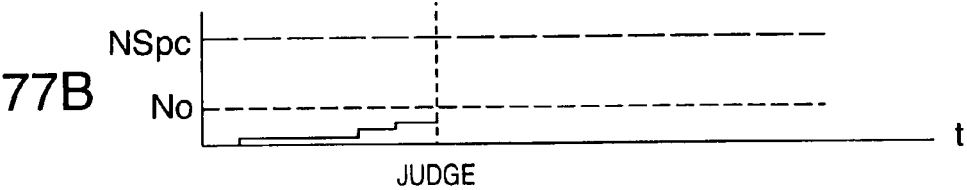

FIG. 76 illustrates an embodiment for solving this problem. The output signal of the multi-channel photomultiplier tube 101g is inputted into an analogue switch 1A. A PC 10g connects an initial condition of the analogue switch with B, i.e., a photon counting circuit 1B. This means that, when executing the fluorescent light detection on the per-pixel basis, the photon counting is executed first. FIGS. 77A, 77B, which illustrate the time-elapsing change of the photon counting signals, correspond to the case where the fluorescent lights are exceedingly weak and the fluorescent light intensities are detected by the photon counting detection.

FIG. 77A illustrates the pulse signals $S_{PC}$ formed by binarizing the photon pulse signals with the use of the comparator, the photon pulse signals having been detected by the photomultiplier tubes. FIG. 77B illustrates a counted signal $NS_{PC}$ obtained by counting the pulse number of the pulse signals in FIG. 77A. If the count signal $NS_{PC}$ does not exceed a determined threshold value No at a point-in-time at which a time a $(t_s/L_x)$ has elapsed after the starting of the counting, the analogue switch continues the photon counting in the present state that will remain unchanged, then executing the photon counting during the per-pixel fluorescent light detecting time $t_s/L_x - \Delta t$. With respect to α in the time $\alpha(t_s/L_x)$ at which this judgement should be made after the starting of the counting, it is all right to assume α to be substantially 0.01 to 0.3. Namely, this time is satisfying enough if it is of an order of a time during which the photon counting pulses are at the maximum and approximately 10 or more pulses are detected. The above-described phrase "at the maximum" means the case where the pulse signals have been generated at the highest ultra-density within this time.

Figure 77C:
Figure 77D:
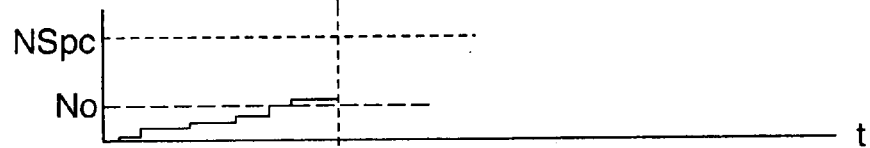
Figure 77E:
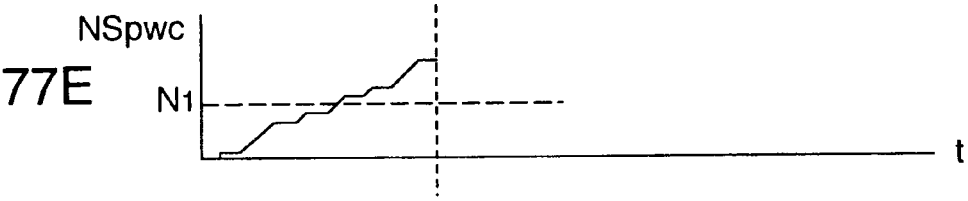

FIGS. 77C to 77E illustrate the case where the fluorescent light intensities become higher and executing the photon counting causes inconveniences to occur, namely, the case where 2 or more of the photon counting pulses are superimposed on each other at the same time or partly. In this case, the after-comparator pulse signals $S_{PC}$, when formed by comparating the partly superimposed pulses, are increased in their widths as illustrated in FIG. 77C. FIG. 77D illustrates a counted signal $NS_{PC}$ of the pulse signals in FIG. 77C. The counted signal $NS_{PC}$ exceeds the threshold value $N_0$ at the point-in-time $\alpha(t_s/L_x)$, which shows that the fluorescent light detection by the photon counting is not suitable for the fluorescent light intensities at the point-in-time. Thus, at this point-in-time, the analogue switch in FIG. 76C is connected to C so as to integrate the photomul signals in an analogue manner by an integrating circuit 1C. In this way, by judging, on the per-pixel basis, whether the fluorescent light detection should be executed by the photon counting or the analogue integration, the detection is executed in such a manner that the optimum method is selected for each detection.

Figure 75:
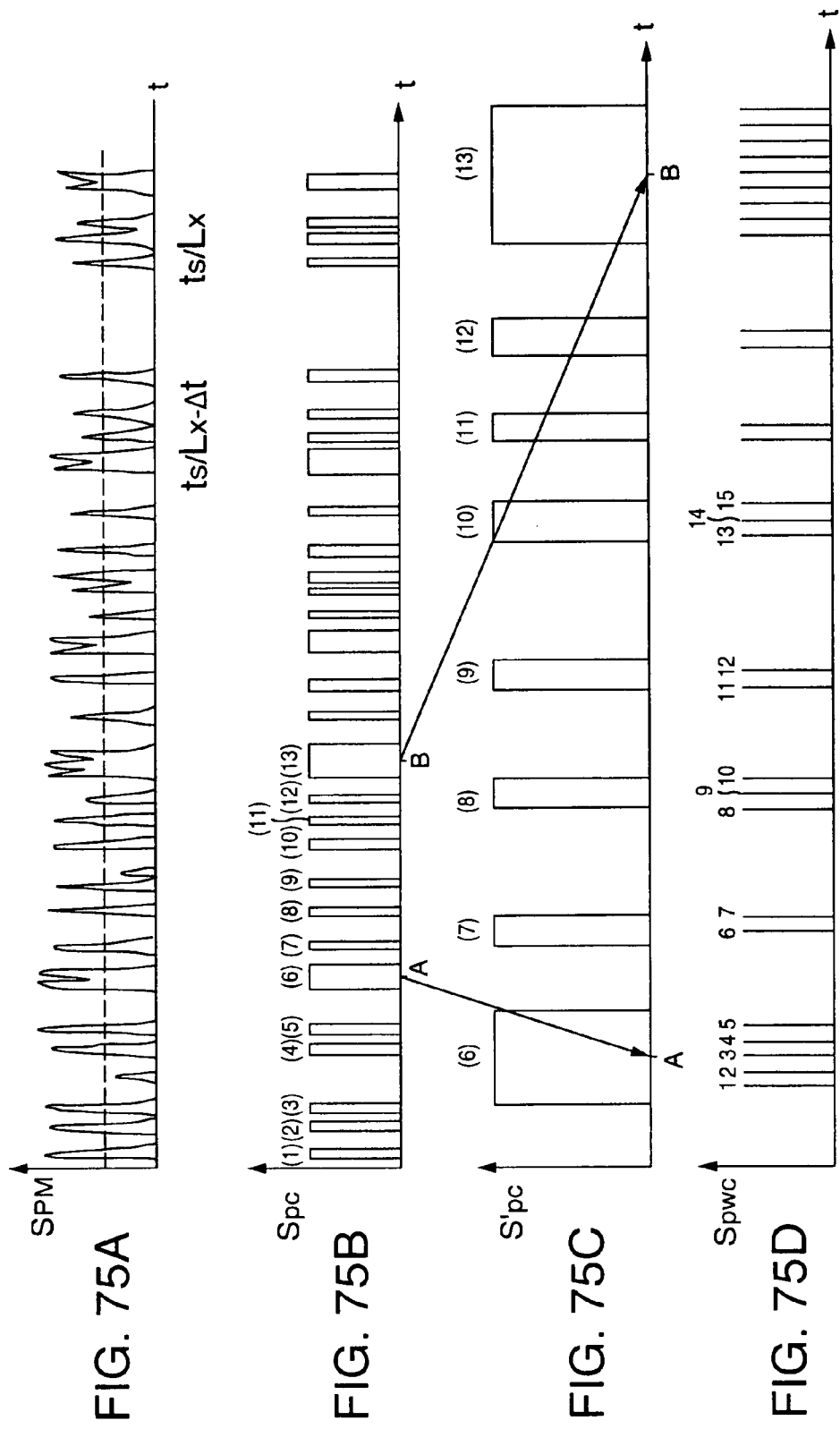
FIGS. 75A to 75D are diagrams for illustrating photon pulse signals in the case of strong detected lights.

Incidentally, although not illustrated, if the fluorescent light intensities become higher than those in the state in FIG. 77C, the pulses in FIG. 77C are connected with each other and as a result, the pulse-counted value become equal to several or 0. At this time, as illustrated in FIG. 75D, employing the signals $S_{PWC}$, for counting the signals $S_{PC}$ with the use of the rectangle-shaped high-frequency pulses with the constant frequency, a pulse-counted signal $NS_{PWC}$ thereof is given as is illustrated in FIG. 77E. The use of the signal $NS_{PWC}$ makes it possible to judge that the value of the signal exceeds a threshold value $N_1$. Then, switching the analogue switch to C allows the analogue detection to be executed without a mistake even in the case of the detection of the even higher fluorescent light intensities.

Figure 78A:
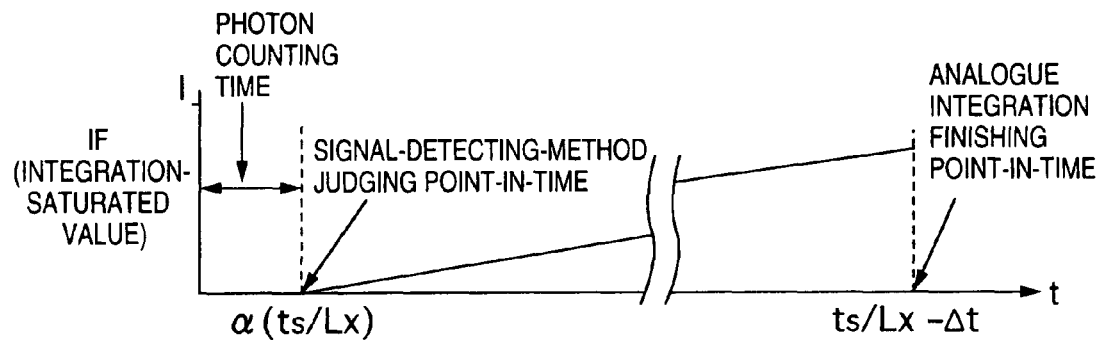
FIGS. 78A, 78B are diagrams for indicating a method of detecting even stronger detected lights according to the present invention.

Once the switching to the analogue detection has been performed, the circuit 1C starts the analogue integration with the switching point-in-time employed as the starting point-in-time. As illustrated in FIG. 78A, setting a target pixel detection starting point-in-time to be the starting point-in-time (this point-in-time is assumed to be 0), the circuit 1C starts the integration from the point-in-time $\alpha(t_s/L_x)$. Then, as is the case with the photon counting, the circuit 1C continues the integration until the point-in-time $t_s/L_x - \Delta t$, and A/D-converts the integrated value at this point-in-time. The A/D-converted digital information IC01 is transferred to a circuit 100g. In the case where the fluorescent light intensities are weak, the photon counting is continued, and the photon counting signals ranging from the point-in-time 0 to the point-in-time $t_s/L_x - \Delta t$ are counted. The counted digital information IB01 is also transferred to the circuit 100g. The results of the photon counting digital information and the analogue integration digital information, which have been transferred to the circuit 100g in the parallel manner as described above from the respective channels of the multi-channel photomultiplier tube 101g, are transferred to the PC 11g, i.e., the personal computer. As having been described previously, it was recognized at the point-in-time $\alpha (t_s/L_x)$ whether the detection executed in each channel has been executed by the photon counting or the analogue integration. Consequently, the PC 11g selects and employs the method suitable for the detection for each channel. Namely, the selection signals therefor are simultaneously transferred to the information IC01, IC02, . . . in FIG. 76.

Incidentally, in the above-described embodiment, it was judged at the point-in-time $\alpha(t_s/L_x)$ which method should be selected of the photon counting and the analogue integration. However, it is also allowable to execute the detection from the beginning by both of the methods simultaneously and to perform the selection after the time $t_s/L_x - \Delta t$ has elapsed.

FIG. 78A indicates a variation in the integration signal when the analogue integration detection is executed. Between the point-in-time a $(t_s/L_x)$ at which the analogue integration detection was started and the point-in-time $t_s/L_x - \Delta t$, the integrated value has been increasing with an inclination proportional to the magnitudes of the detected fluorescent light intensities. Then, the integrated value at the point-in-time $t_s/L_x - \Delta t$ undergoes the sample holding, then being A/D-converted. The analogue detection as described above makes it possible to capture the variation in the signal intensities over a dynamic range of approximately 2 order.

Next, referring to FIG. 78B, the explanation will be given below concerning a method of making the detection executable in the range of the detection of the even higher fluorescent light intensities. In this case, since the integrated value had been saturated before the analogue integration detection reached the point-in-time $t_s/L_x - \Delta t$, the detection at this point-in-time is impossible: However, using the high-frequency pulse signals $S_{hc}$ used in FIG. 75D, by counting $(t_F - \alpha(t_s/L_x))$, i.e., a time ranging from the point-in-time $\alpha(t_s/L_x)$ at which the integration was started to a point-in-time $t_F$ at which the integration was saturated, the detected intensity I is determined by the following equation since the integration-saturated value $I_F$ had been known in advance:

$$I = I_F \cdot ((1-\alpha)t_s/L_x - \Delta t)/(t_F - \alpha(t_s/L_x))$$

In this way, measuring the time from the integration-starting point-in-time to the integration-saturated point-in-time allows the dynamic range to be enlarged by approximately 1 order further.

In order to count the saturated point-in-time as described above, it is well enough to add the following function to the analogue integrating circuit illustrated in FIG. 76. Namely, setting the integration signal of the integrating circuit 1C to be the 1st input and setting a signal level equivalent to the predetermined integration-saturated value to be the 2nd input, these two inputs are inputted into the comparator circuit. Then, from variations in the outputted signals resulting from the inputs, it can be assumed that the counting has been finished. This allows the saturated point-in-time to be counted.

As having been explained so far, the fluorescent lights detected by the multi-channel photo-multiplier tubes 101g, 102g are detected in the 64 channels in parallel, and are inputted into the circuit 100g in parallel and are converted into the time-sequential signals, then being transferred to the PC 11g. By scanning the x stage in FIG. 70, as illustrated in FIG. 71, the 64 pixels arranged in the y direction are detected simultaneously and, in the x direction, in sequence. Although not illustrated, the optical length-measuring device is attached to each of the xy stage 4g in FIG. 70, and the length-measuring device measures the displacement quantities of the xy stage. The dimensions $\Delta x$, $\Delta y$ of the fluorescent light detected pixels on the DNA chip are each assumed to be, for example, 2 µm. The measurement of each pixel is started from a point-in-time at which the length-measuring device of the x stage measures the displacement of 2 µm.

Hereinafter, the explanation will be given concerning a concrete embodiment of the multi-spot fluorescent light detection or the multi-spot DNA inspection according to the present invention. The scanning operation is performed in the x direction, and the shifting operation by the amount of 1 pixel on the basis of one scanning in the x direction is performed in the y direction, and the x positions are shifted by a large amount every 10 scannings. This is repeated, thereby executing the detection or the inspection in the 2-dimensional manner.

When a stage's position length-measuring signal of the measurement starting is detected by the scanning in the x direction, the photon counting is started first. It is assumed that $L_x$, i.e., the detected pixel number in the x direction, is equal to 6400, and the pixel pitch is equal to 2 µm, and $t_s$, i.e., the time needed to scan this 2 µm, is equal to 60 µsec. The width of the pulses generated after the photomultiplier tube has received 1 photon is equal to substantially 30 n sec. Consequently, when executing the photon counting during 40 µsec out of the time of 60 µsec during which the spot has passed through one pixel, it becomes possible to count hundreds to thousands of photons using the photon counting method. Toward the lights the intensities of which are higher than this, the pulse signals are connected with each other and accordingly the analogue integration detection is executed. The dynamic range of this analogue detection is equal to approximately 100. Consequently, by using the photon counting and the analogue integration together in a manner of being switched to each other by the above-described method, it becomes possible to obtain the dynamic range of approximately 10000.

Figure 78B:
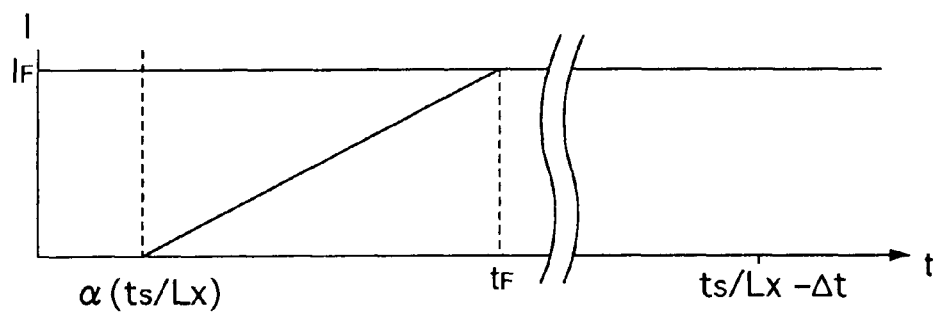

Moreover, by using together the method explained in FIG. 78B by which the detected intensity is determined from the point-in-time at which the analogue integration was saturated, it becomes possible to enlarge the dynamic range by 1 order further. As a consequence, it becomes possible to execute the fluorescent light detection in a short time over a broad dynamic range of $2^{16}$, i.e., 65536, namely, from the weak detected lights of several photons in 40 µsec up to the strong detected lights attaining to 100000 photons.

When the above-explained fluorescent light intensities include 3 areas, i.e., the photon counting area, the analogue integration area, and an analogue integration-saturated time detecting area, in order to cause the respective boundaries therebetween to be connected with each other smoothly, the calibration is performed in advance using strong detected lights corresponding to the boundary regions.

Although, in the above-described embodiment in FIG. 76, the detection is executed by time-dividing the photon counting and the analogue integration, it is also possible to use both of them all the time and to select the signal to be employed in correspondence with the intensities of the detected fluorescent lights.

The above-described switching between the detecting methods is not limited to the fluorescent light detection, but is generally effective in the case where the per-pixel detecting time Tp is restricted to a short time. Namely, when Nr, i.e., the ratio between Tp and the time-width $\Delta t$ of the photon detection pulses, is smaller as compared with the requested detection dynamic range Nd, namely, when $$Tp/\Delta t = Nr < Nd$$

holds, the detection becomes executable in the broad range extending from the weak photon counting area up to the strong lights the photon counting of which is impossible.

The scanning by the amount of 6000 pixels is performed in the x direction at a speed of 60 µsec/1 pixel and at this time, in the y direction, 64 pixels are detected simultaneously with 10 pixels skipped. Accordingly, at a point-in-time at which the one scanning is over in spending 360 msec, 384000 pixels have been detected in the above-described broad dynamic range. When the one scanning is over, the stage is displaced in the y direction by the amount of 1 pixel, i.e., 2 µm, then detecting the adjacent pixel line similarly. This operation is repeated 10 times, thereby executing the detection of 640× 6000 pixels. Even if accelerating and decelerating times needed to return the stage are added, the detection of the pixels in the above-described number is finished in spending 4 to 5 seconds.

Next, the stage is displaced largely in the y direction by the amount of 640 pixels, i.e., 2 µm×640=1.28 mm, then repeating the above-described operation. Repeating this large displacement 10 times allows 6400×6000 pixels to be detected in spending substantially 40 to 50 seconds. Namely, it becomes possible to accomplish the fluorescent light detection or the weak light detection of the images of 6000×6000 pixels the minimum detection intensity of which is of several photons with a resolution of 2 µm, in the dynamic range of $2^{16}$, and within 1 minute.

The above-described embodiment is of the case where the detecting time requested for each pixel is short. However, in the case where the per-pixel detecting time is larger by 1 order or more and the dynamic range of $2^{16}$ is required similarly, the method illustrated in FIG. 78B where the integration-saturated time is determined becomes unnecessary. Also, if the width of the photon detection pulses from the photomultiplier tube can be shortened even further, the photon counting alone or the combination of the photon counting and the analogue integration detection makes the detection possible.

When trying to apply the DNA inspection, in particular, the DNA inspection using the DNA chip, to a usage such as group checkup where a large number of samples are dealt with, it becomes important to implement an inspecting apparatus having the characteristics of a high-sensitivity, a high-resolution, a broad dynamic range, and a high-speed. This implementation has been made possible by the following method: Using the multi-spot excitation lights or the sheet-shaped excitation beams explained in the previously-mentioned embodiments, the fluorescent lights from a plurality of pixels are detected simultaneously, and the relative positions between the excitation lights and a sample are changed by the scanning so as to detect the fluorescent lights in sequence.

Detecting the 64 (M=64) pixels simultaneously has allowed the 6000×6000 pixels to be detected in spending a time less than (300 μsec/pixel), namely, the average pixel detecting time has become shorter than (300 μsec/M). As a result, it has become possible to execute the detection in a time less than 3 minutes per sample. This result can respond to and satisfy the needs of the high-speed inspection because, conventionally, it took 10 minutes or more to detect the fluorescent light images of the pixels in the above-described number. Furthermore, by using the photon counting and the analogue integration together, it becomes possible to execute the detection in a time less than (50 μsec/pixel), thereby eventually allowing the detection to be executed within 1 minute.

Moreover, in the above-described fluorescent light detection using the multi spots, the diameter of the multi spots on the sample is made smaller, thereby performing the irradiation with the multi-spot excitation lights or the sheet-shaped excitation lights. Here, the multi-spot excitation lights include a large number of M microscopic spots the diameter of which is smaller than 3 μm and larger than 0.3 μm, and the sheet-shaped excitation lights have a focus-achieving width that is smaller than 3 μm and larger than 0.3 μm. The fluorescent lights generated by the irradiation from the respective multi spots or the respective sheet-shaped irradiation locations are separated from the excitation lights, then detecting the fluorescent light images emitted from the sample with the use of a plurality of weak light detecting components. Signals obtained from the respective detecting components are stored individually. Then, the relative positions between the multi-spot excitation lights or the sheet-shaped excitation lights and the sample are changed, thus storing the above-described signals in sequence. This allows the signals to be stored and collected over a desired range on the sample. Then, the fluorescent light picture is constructed from the collected data, thereby making it possible to inspect the DNA. The use of the method as described above enhances the resolutions of the detected images. Utilizing the enhanced resolutions makes it possible to detect a to-be-inspected DNA in a cell as the fluorescent light images and to execute the DNA inspection of the cell in the following way: For example, employing, as a sample, a desired target DNA to which a fluorescent light material has been added, the fluorescent light material-added target DNA is hybridized with the corresponding DNA among 1-chain DNAs in the cell.

Figure 79:
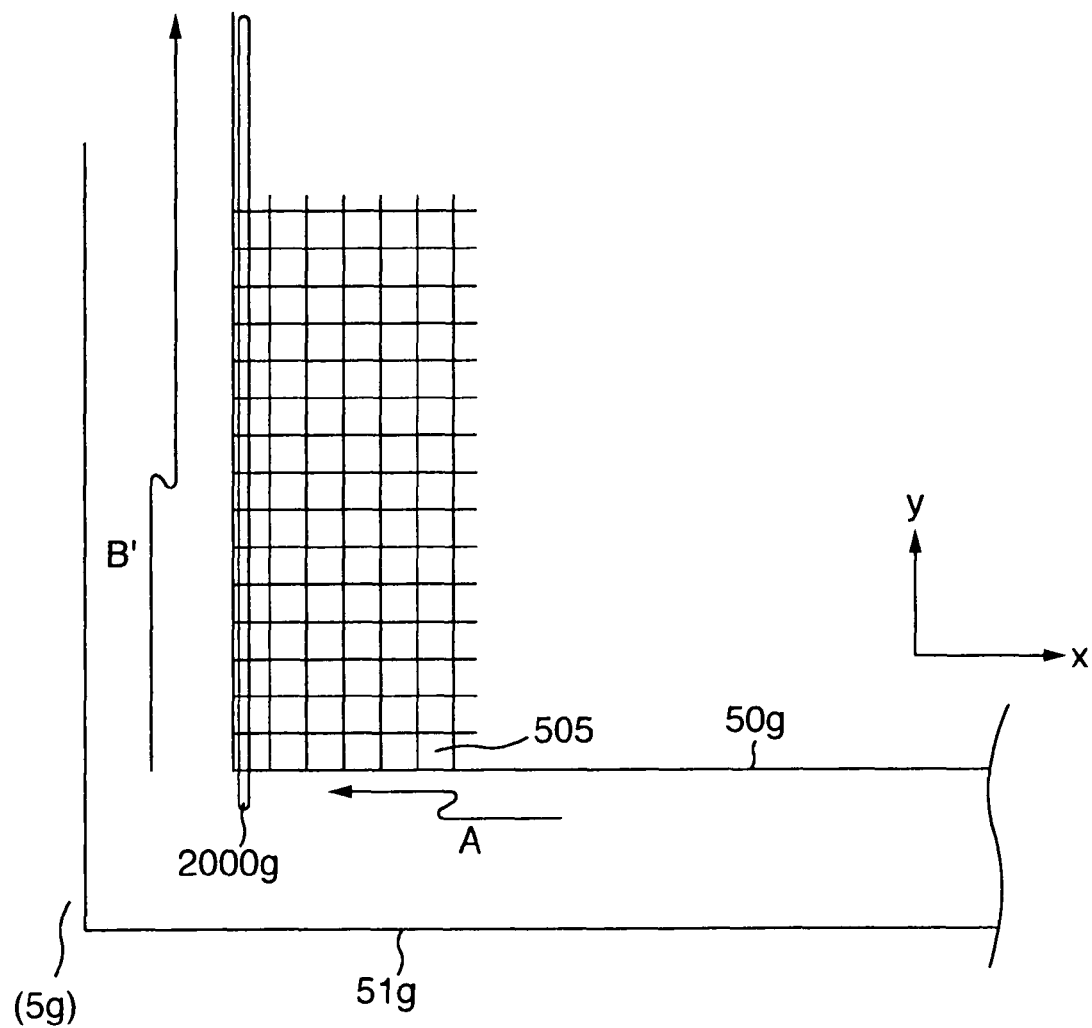
FIG. 79 is a plane view of the cells of the DNA chip for illustrating the case where there are employed the sheet-shaped excitation lights according to the present invention.

FIG. 79 is an embodiment-illustrating diagram of the fluorescent light detection in the present invention and, in particular, of the fluorescent light detection that is effective in the DNA inspection. The same reference numeral as that in FIG. 71 denotes the same component. Instead of the multi-spot excitation lights illustrated in FIG. 71 the irradiation of which is performed with the spacing of 10 pixels, sheet-shaped excitation lights 2000 are employed. As is the case with the optical system in FIG. 70, fluorescent lights obtained by the irradiation with the excitation lights are separated from the excitation lights, then being detected by the 1-dimensional photomultiplier tube array or the 1-dimensional ultra-high sensitivity censor. The excitations by the sheet-shaped excitation beams are executed simultaneously over mutually adjacent, for example, 50 pixels in a 1-dimensional direction, then being detected simultaneously by the 1-dimensional high sensitivity censor. The scanning by the amount of, for example, 500 pixels is performed in the x direction perpendicular to the sheet-shaped beams that is longer in the y direction, thereby obtaining fluorescent light images by the amount of 50×500 pixels. Next, the sheet-shaped beams are displaced by the amount of 50 pixels in the y direction, then executing the above-described one scanning. Repeating this operation 1 times finally obtains the fluorescent light picture of 500×500 pixels. In the present embodiment, the background noise becomes slightly larger in comparison with the above-described embodiments where there is performed the irradiation with the isolated spot light or the spot lights separated with each other with the spacing therebetween. Nevertheless, in comparison with the cases where the irradiation is performed largely in the 2-dimensional plane-like manner, it is possible to execute the fluorescent light detection with a less noise. The signals obtained from the 1-dimensional photomultiplier tube array or the 1-dimensional ultra-high sensitivity censor are weak lights, and accordingly the photon counting is executed.

Figure 80:
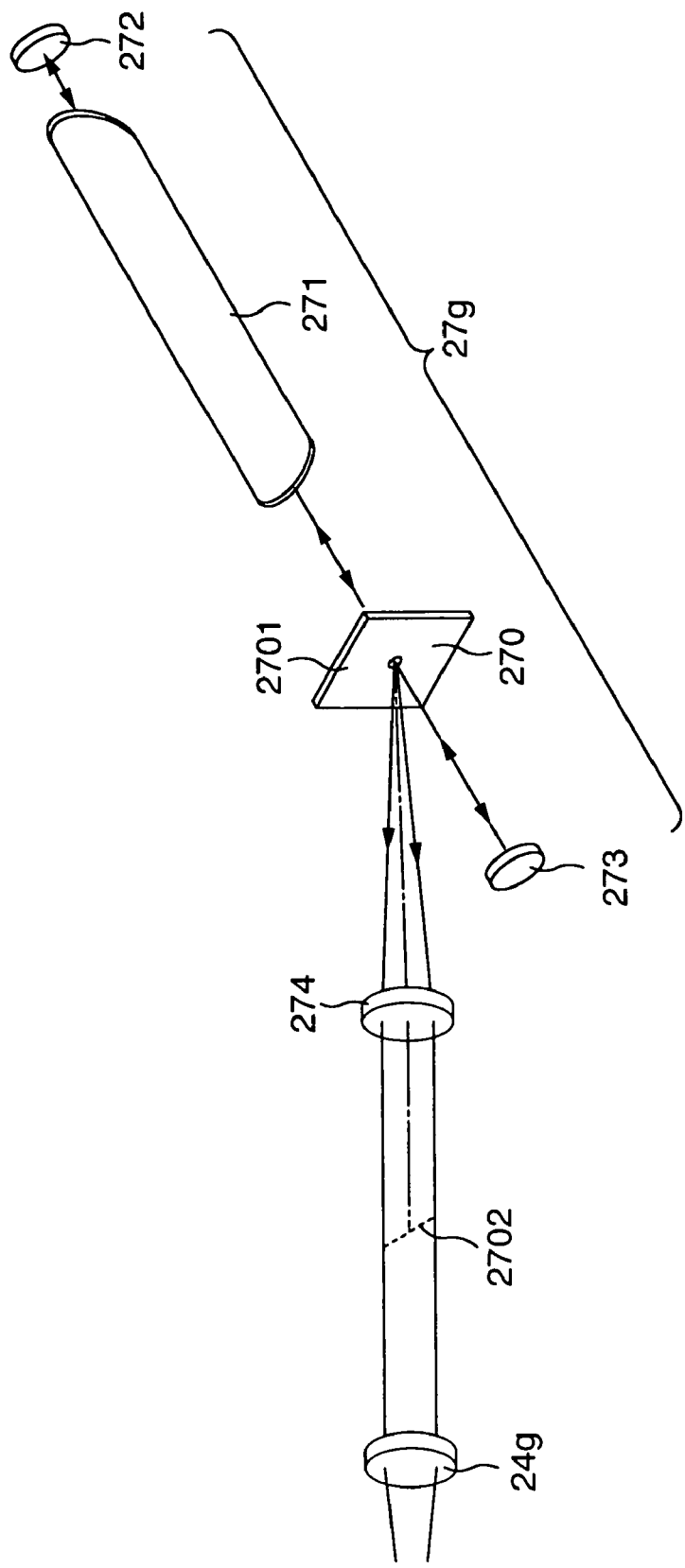
FIG. 80 is a perspective view of a portion of an optical system for illustrating an embodiment where the multi spots according to the present invention are formed by a hologram within a laser resonator.

FIG. 80 illustrates an embodiment for indicating a method of generating the multi-spot excitation lights used for the fluorescent light detection or the DNA inspection using the fluorescent light detection. In a laser 27g, there are provided windows at Brewster angle at both ends of a laser tube 271 filled with a laser medium. Laser lights emitted out therefrom are returned back by 100% reflection mirrors 272, 273. The energy of the laser light that is reciprocating between the resonator mirrors is usually more than 10 times as high as the beam energy extracted out of the laser resonator through the emitting window from the optical energy within the resonator. In the case of inserting a multi-spot or sheet-shaped beam generating hologram plate 270 into the laser resonator, since a hologram 2701 has been formed in advance so that the multi spots or the sheet-shaped beams are generated, as illustrated in the drawing, multi spots 2702 are reproduced through a lens 274. Incidentally, the laser light with which the hologram has been irradiated forms the multi-spot images at a diffraction efficiency of substantially 10%. The remaining light passes through the hologram without being varied as a 0th light, then reciprocating within the laser resonator. These multi spots are completely identical to the multi-spot lights at the time of immediately after having passed through the mask-like circular aperture array explained in FIG. 70. This condition makes it possible to irradiate a detection target with the multi spots with the use of the lens 24g in accordance with the configuration in FIG. 70. As a result, it is possible to obtain the multi-spot lights or the sheet-shaped beams the intensities of which are almost 10 times higher as compared with those in the conventional case where the hologram is located in a laser-emitting optical path. Consequently, it becomes possible to execute the high-speed and high-sensitivity fluorescent light detection and DNA inspection.

In the above-described embodiment, the explanation has been given concerning the case of the excitation lights having 1 wavelength. The present invention, however, also exhibits the effects in the case of using the excitation lights having 2 wavelengths or 3 or more wavelengths. In this case, conventionally, when trying to execute the detection using the plurality of wavelengths, it has taken an exceedingly long time to do so. On the other hand, the execution of the photon counting detection using the multi-spot lights according to the present invention makes it possible to execute the detection with a high-sensitivity and at a high-speed.

What is claimed is:

1. A DNA inspecting apparatus including an excitation light irradiating system for irradiating a DNA chip with excitation lights from an excitation light light-source and a fluorescent light detecting system for detecting fluorescent lights generated from a fluorescent material on said DNA chip, comprising:
   a multi-spot excitation lights-generating optical system for causing a plurality of M excitation lights to be simultaneously generated on said DNA chip as multi-spot excitation lights, said multi-spot excitation lights having a spot diameter d that is equal to or smaller than a dimension D of a large number of L cells existing on said DNA chip,
   an objective lens for causing said fluorescent material to be simultaneously irradiated with said multi-spot excitation lights in said dimension d, said fluorescent material being added to a DNA fragment on said DNA chip,
   a beam splitter for guiding said obtained fluorescent lights to a fluorescent light detecting optical path through said objective lens,
   fluorescent light detector to separate and detect said fluorescent lights generated by said multi-spot excitation lights, and
   a control system which arranges said plurality of M excitation lights onto said DNA chip on a straight line with a spacing of substantially kd with reference to said spot diameter d and an integer k, and repeats an operation in sequence k times, said operation being an operation where, after said irradiation with said plurality of M excitation lights has been performed during said time $\Delta t$, said array is displaced in a direction of said array by substantially d and said irradiation is performed again during said time $\Delta t$, and thereby executes said inspection toward kM spot positions in said array direction, and displaces said DNA chip and said objective lens relatively at least in a direction perpendicular to said array direction, and thereby inspects said desired 2-dimensional area on said DNA chip.

2. The DNA inspecting apparatus as claimed in claim 1, wherein said multi-spot excitation lights-generating optical system generates said plurality of M excitation light spots simultaneously, said plurality of M excitation light spots being arranged in a 1-dimensional or 2-dimensional manner with a fixed pitch on a straight line.

3. The DNA inspecting apparatus as claimed in claim 1, wherein said plurality of M excitation lights is formed by a microlens array.

4. The DNA inspecting apparatus as claimed in claim 1, wherein said plurality of M excitation lights is formed by a hologram.

* * * * *